US012681015B2

(12) United States Patent
Dalli et al.

(10) Patent No.: US 12,681,015 B2
(45) Date of Patent: Jul. 14, 2026

(54) METHODS FOR PREDICTING PATIENT RESPONSE TO DMARDS

(71) Applicant: Queen Mary University of London, London (GB)

(72) Inventors: Jesmond Dalli, London (GB); Romain Alexandre Colas, London (GB); Costantino Pitzalis, London (GB); Esteban Alberto Gomez Cifuentes, London (GB); Conrad Bessant, London (GB)

(73) Assignee: Queen Mary University of London, London (GB)

( * ) Notice: Subject to any disclaimer, the term of this patent is extended or adjusted under 35 U.S.C. 154(b) by 1063 days.

(21) Appl. No.: 17/761,046

(22) PCT Filed: Sep. 17, 2020

(86) PCT No.: PCT/GB2020/052260
§ 371 (c)(1),
(2) Date: Mar. 16, 2022

(87) PCT Pub. No.: WO2021/053343
PCT Pub. Date: Mar. 25, 2021

(65) Prior Publication Data
US 2022/0349886 A1 Nov. 3, 2022

(30) Foreign Application Priority Data
Sep. 17, 2019 (GB) ...................................... 1913383

(51) Int. Cl.
*G01N 33/564* (2006.01)
*G01N 33/92* (2006.01)
(Continued)

(52) U.S. Cl.
CPC ........... *G01N 33/564* (2013.01); *G01N 33/92* (2013.01); *G16H 20/10* (2018.01); *G16H 50/30* (2018.01);
(Continued)

(58) Field of Classification Search
CPC .. G01N 33/564; G01N 33/92; G01N 2570/00; G01N 2800/102; G01N 2800/52; G16H 20/10; G16H 50/30
See application file for complete search history.

(56) References Cited

U.S. PATENT DOCUMENTS

2018/0214489 A1* 8/2018 Riordan .............. G01N 33/5005
2018/0271818 A1 9/2018 Bannenberg et al.
(Continued)

FOREIGN PATENT DOCUMENTS

WO WO 2017/210604 A1 12/2017
WO WO 2018197650 A1 11/2019

OTHER PUBLICATIONS

Steuer AE, et al. "Comparison of conventional liquid chromatography-tandem mass spectrometry versus microflow liquid chromatography-tandem mass spectrometry [. . . ]". J Chromatogr A. Feb. 13, 2015;1381:87-100. doi: 10.1016/j.chroma.2014.12.084. Epub Jan. 8, 2015. PMID: 25596763. (Year: 2015).*
(Continued)

*Primary Examiner* — Larry D Riggs, II
*Assistant Examiner* — Emilie A Smith
(74) *Attorney, Agent, or Firm* — Grimes & Yvon LLP

(57) ABSTRACT

The present invention provides a method for predicting whether a patient having, suspected of having, or at risk of developing an inflammatory condition will respond to treatment with a disease-modifying antirheumatic drug (DMARD) comprising measuring the level of at least one specialized pro-resolving mediator (SPM) in a DMARD
(Continued)

naïve patient sample and classifying the patient as a predicted DMARD responder or a predicted DMARD nonresponder. The present invention also provides a method of assessing the efficacy of a disease-modifying antirheumatic drug (DMARD) for use in the treatment of an inflammatory condition in a patient. The present invention also provides a method of predicting which rheumatoid arthritis pathotype a patient having, suspected of having, or at risk of developing rheumatoid arthritis will develop.

22 Claims, 30 Drawing Sheets

(51) Int. Cl.
*G16H 20/10* (2018.01)
*G16H 50/30* (2018.01)
(52) U.S. Cl.
CPC ... *G01N 2570/00* (2013.01); *G01N 2800/102* (2013.01); *G01N 2800/52* (2013.01)

(56) References Cited

U.S. PATENT DOCUMENTS

2018/0284118 A1* 10/2018 Darrah .................... A61P 29/00
2021/0382068 A1* 12/2021 Keskin ............... A61K 39/0011

OTHER PUBLICATIONS

Motwani, Madhur Parmanand; (2017) Immunomodulatory effect of specialised pro-resolving mediators in humans. Doctoral thesis (Ph.D), UCL (University College London), 234 pages. (Year: 2017).*
Arnardottir et al., Resolvin D3 Is Dysregulated in Arthritis and Reduces Arthritic Inflammation; J. Immunol. 197:2362-2368; 2016.
Barden et al., Specialised pro-resolving mediators of inflammation in inflammatory arthritis; Prostaglandins Leukot. Essent. Fat. Acids 107:24-29; 2016.
Humby et al., Synovial cellular and molecular signatures stratify clinical response to csDMARD therapy and predict radiographic progress . . . ; Ann. Rheum. Dis. 78:761-772; 2018.
Humby et al., Response to: Synovial cellular and molecular signatures stratify clinical response to csDMARD therapy . . . ; Ann. Rheum. Dis. 79:e141; 2020, 2 pages.
Lewis et al., Molecular Portraits of Early Rheumatoid Arthritis Identify Clinical and Treatment Response Phenotypes; Cell Reports 28:2455-2470; 2019.
Parveen et al., Serum Lipid Alterations in Early Rheumatoid Arthritis Patients on Disease Modifying Anti Rheumatoid Therapy; Ind. J. Clin. Biochem. 32:26-32; 2017.
Perretti et al., Actions of SPM in regulating host responses in arthritis; Mol. Aspects Med. 58:57-64; 2017.

* cited by examiner

ALOX15 activity

ALOX12 activity

ALOX5 activity

C

Figure 5:
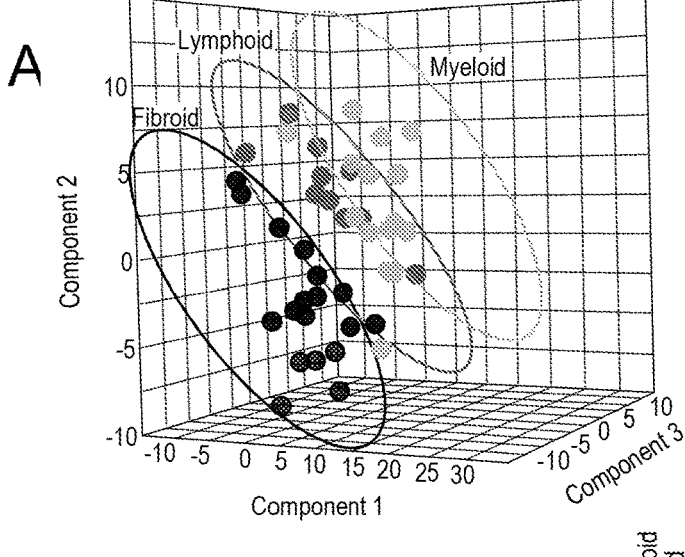
Figure 5:
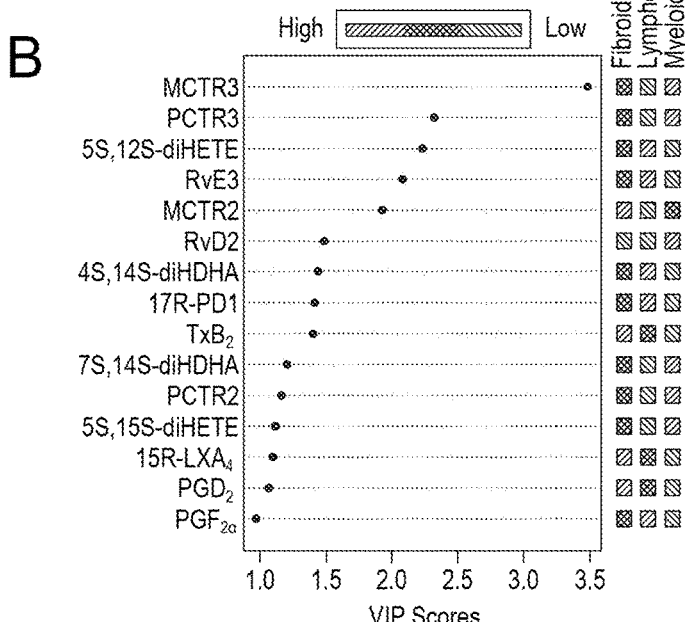
Figure 5:
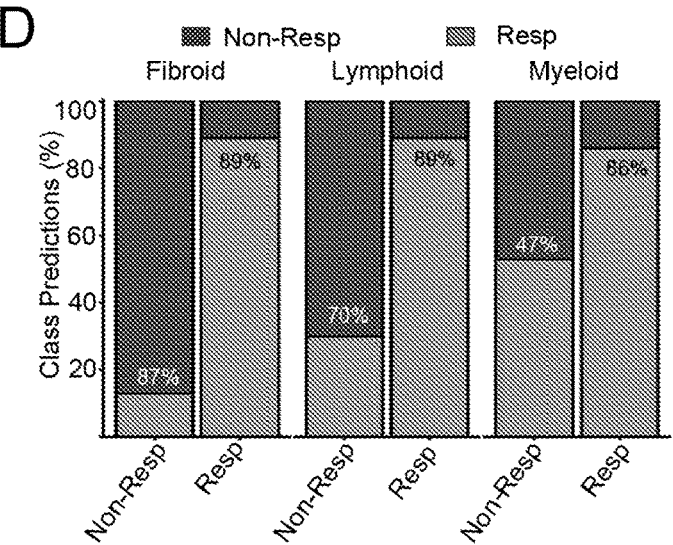
Figure 5:
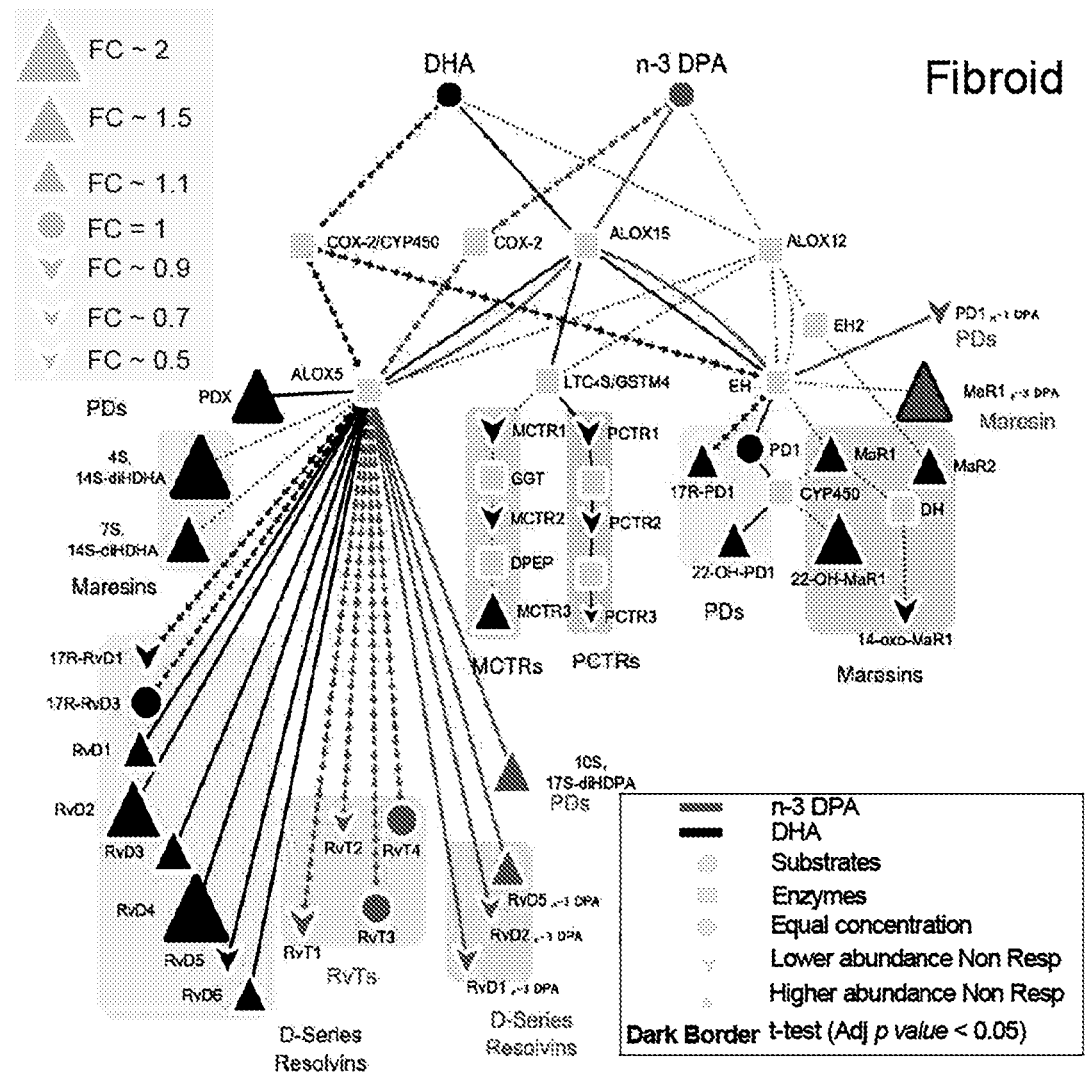
Figure 5:
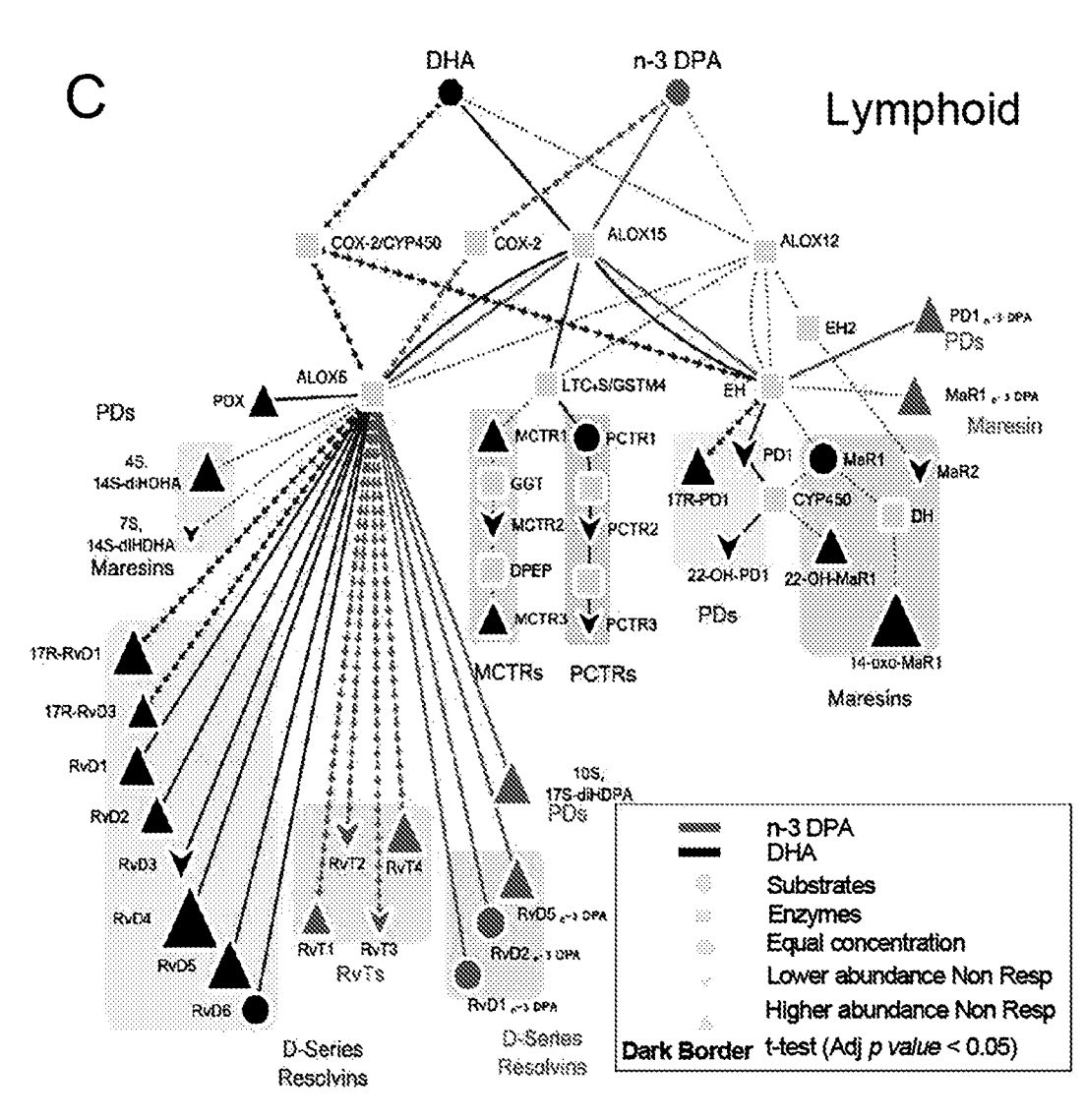

Fig. 5
(continued)

C

A

B

D

Score Plot

E

Fig. 11

METHODS FOR PREDICTING PATIENT RESPONSE TO DMARDS

The present application relates to a method for assessing the efficacy of a disease-modifying antirheumatic drug (DMARD) for use in the treatment of an inflammatory condition. The application also relates to a method for predicting which rheumatoid arthritis pathotype a patient having, suspected of having, or at risk of developing rheumatoid arthritis will develop. The application also relates to a method of predicting whether a patient having, suspected of having, or at risk of developing an inflammatory condition will respond to treatment with a DMARD.

It is widely believed that a precision medicines approach is likely to be more effective in the treatment of patients with chronic inflammatory disorders, including those with rheumatoid arthritis (RA), than the current process where patients are treated in a prescriptive manner using a one size fits all approach. Unfortunately, the lack of robust biomarkers to determine treatment responsiveness in many chronic inflammatory conditions, including rheumatoid arthritis, has hindered the development of this approach in clinical settings.

Results described herein demonstrate that plasma lipid mediator concentrations prior to the initiation of treatment are different in patients that respond to DMARDs when compared with those that do not. Using machine learning methodologies, the inventors found that the concentrations of a group of mediators known as specialized pro-resolving mediators (SPMs) were predictive of treatment responsiveness in two RA cohorts, with prediction accuracy for response to treatment of up to ~95%. Furthermore, plasma SPM concentrations prior to DMARD treatment initiation were also found to reflect the distinct joint disease pathotypes. Of note, while the patients enrolled in this study were DMARD naïve, most of the patients in both cohorts were on a wide range of other medications for a number of co-morbidities. Therefore, the identification of a specific lipid mediator signature that is predictive of DMARD responsiveness suggest that changes in these lipid mediators are specific for this group of therapeutics. Given that SPM regulate host innate and adaptive immune responses and that SPM production is reflective of leukocyte activation status (Dalli, J. & Serhan, C. N. "*Specific lipid mediator signatures of human phagocytes: microparticles stimulate macrophage efferocytosis and pro-resolving mediators.*" Blood 120, e60-72 (2012), Gao, Y., et al. "*Female-Specific Downregulation of Tissue Polymorphonuclear Neutrophils Drives Impaired Regulatory T Cell and Amplified Effector T Cell Responses in Autoimmune Dry Eye Disease.*" J Immunol 195, 3086-3099 (2015), and Serhan, C. N. & Levy, B. D. "*Resolvins in inflammation: emergence of the pro-resolving superfamily of mediators.*" J Clin Invest 128, 2657-2669 (2018), the contents of all of which are incorporated herein by reference), the present findings indicate that peripheral blood SPM concentrations may be used as functional biomarkers for patient stratification and predicting treatment responsiveness to DMARDs.

The biosynthesis of SPM involves the stereoselective conversion of essential fatty acids by distinct enzymes, with the successful formation of the bioactive product relying on the expression and activity of the enzyme as well as their appropriate subcellular localization. Chiral chromatographic analysis of plasma 6-months post treatment demonstrated a predominance of the S-isomers of the monohydroxylated fatty acids. While this observation does not exclude the contribution of enzymes such as cytochrome P450 enzymes in the formation of the monohydroxylated fatty acids measured, it suggests that ALOX activity is sustained in DMARD-non-responders despite peripheral blood SPM concentrations being overall reduced in this patient group. Thus, suggesting that the SPM biosynthetic pathways become uncoupled post DMARD treatment initiation.

SUMMARY OF THE INVENTION

According to a first aspect, the invention provides a method of assessing the efficacy of a disease-modifying antirheumatic drug (DMARD) for use in the treatment of an inflammatory condition in a patient, which comprises measuring the levels of at least one specialized pro-resolving mediator (SPM) in samples obtained from the patient before and after administration of the DMARD, wherein an increase in the level of the at least one SPM after administration of the DMARD is indicative of efficacy of the DMARD.

According to a second aspect, the invention provides a method for predicting which rheumatoid arthritis pathotype a patient having, suspected of having, or at risk of developing rheumatoid arthritis will develop comprising measuring the level of at least one specialized pro-resolving mediator (SPM) in a disease-modifying antirheumatic drug (DMARD) naïve patient sample and classifying the rheumatoid arthritis pathotype a patient will develop as Lymphomyeloid, Diffuse-myeloid and Pauci-immune-fibroid.

According to a third aspect, the invention provides a method for predicting whether a patient having, suspected of having, or at risk of developing an inflammatory condition will respond to treatment with a disease-modifying antirheumatic drug (DMARD) comprising measuring the level of at least one specialized pro-resolving mediator (SPM) in a DMARD naïve patient sample and classifying the patient as a predicted DMARD responder or a predicted DMARD non-responder.

Figure 1:
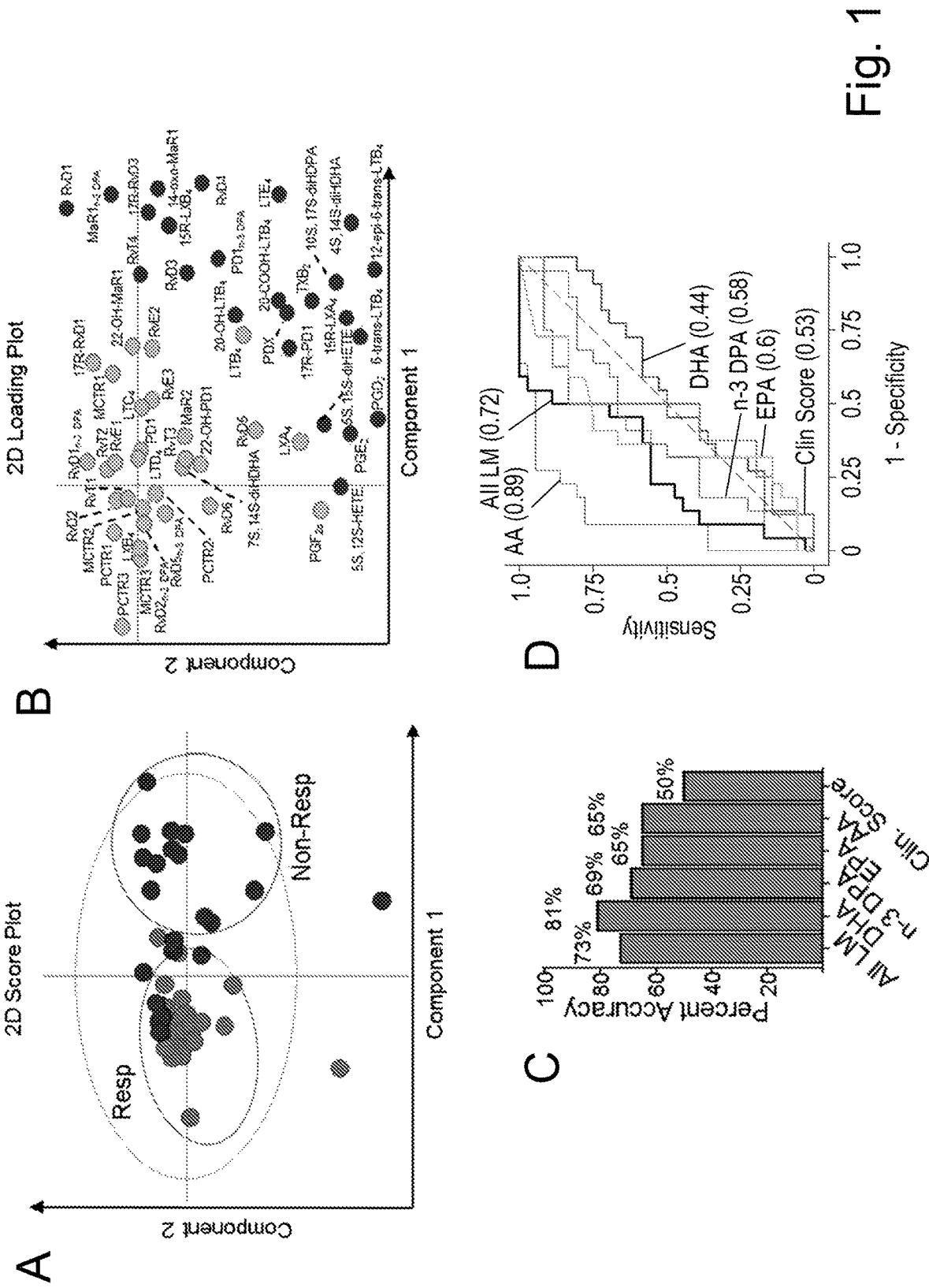
Figure 1:
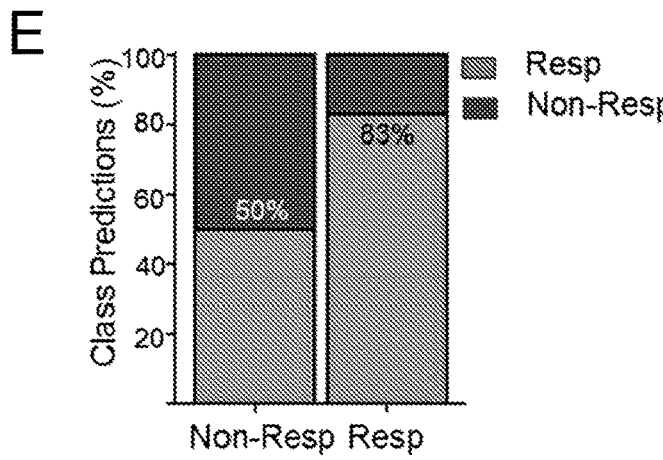
Figure 1:
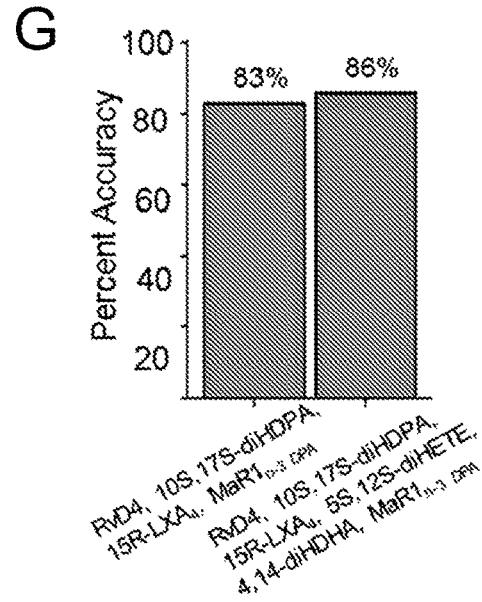
Figure 1:
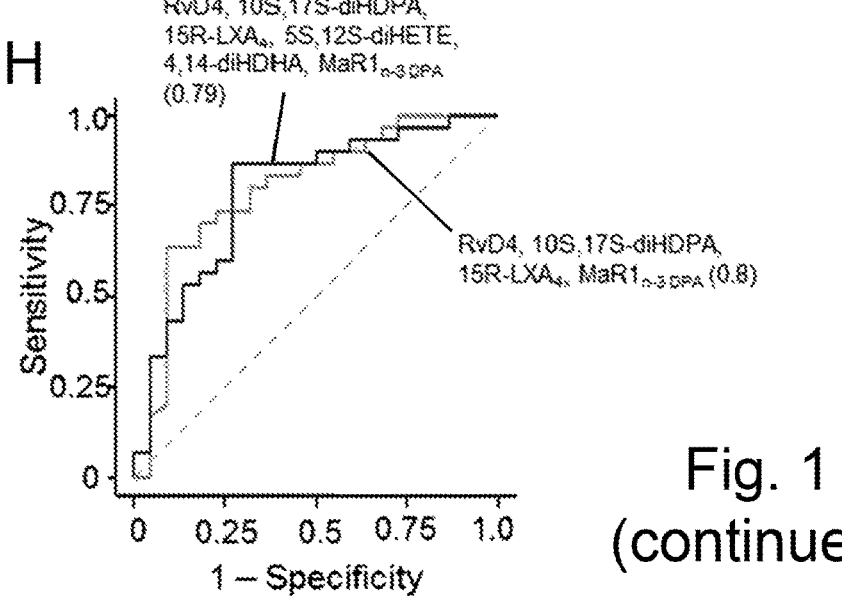
Figure 1:
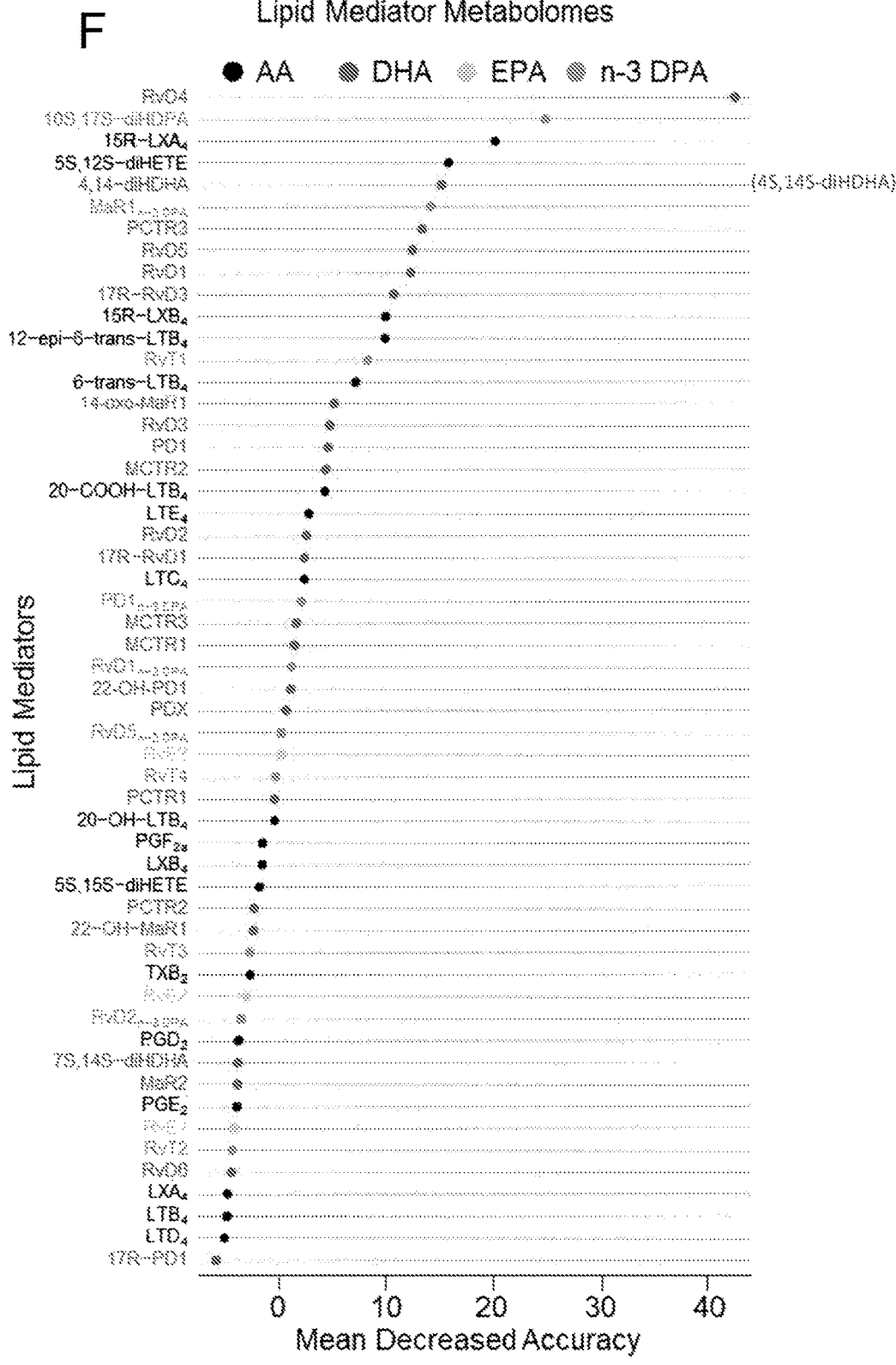

Reference is made to a number of Figures as follows:

FIG. 1— Baseline plasma lipid mediator profiles are predictive of treatment responsiveness in DMARD naive RA patents.

Plasma was collected from RA patients prior to the initiation of treatment with DMARDs and lipid mediator concentrations established using LC-MS/MS based lipid mediator profiling (see methods for details). (A,B) OPLS-DA analysis of peripheral blood lipid mediator concentrations for DMARD responders (Resp) and DMARD Non-Responders (Non-Resp). (A) 2-dimensional score plot with the gray circle representing the 95% confidence regions. (B) 2-dimensional loading plots. Lipid mediators with VIP score greater than 1 are highlighted in blue and upregulated in Non-Resp. Results are representative of n=30 Resp and n=22 Non-Resp. (C) % accuracy score of prediction models based on the combination of all lipid mediators identified and quantified (AL LM) or individual fatty acid metabolomes as indicated. Clin. Score=clinical score (see methods for parameters included). (D) ROC curves and AUC values for predictive models. (E) Classification predictions for each class (sensitivity and specificity) of the n-3 DPA model. Green indicates the samples that were predicted as Resp while blue indicates those patients predicted Non-Resp. Percentages indicate true positives (Resp class) and true negatives (Non-Resp class). (F). Relevance of lipid mediators in the prediction performance of the "ALL LM" model based on decreasing accuracy. (G) % accuracy score of models using the indicated SPM. (H) ROC curves and AUC values for predictive models based on the indicated SPM. All the models were created using the random forest methodology ("randomForest" package from R).

Figure 2:
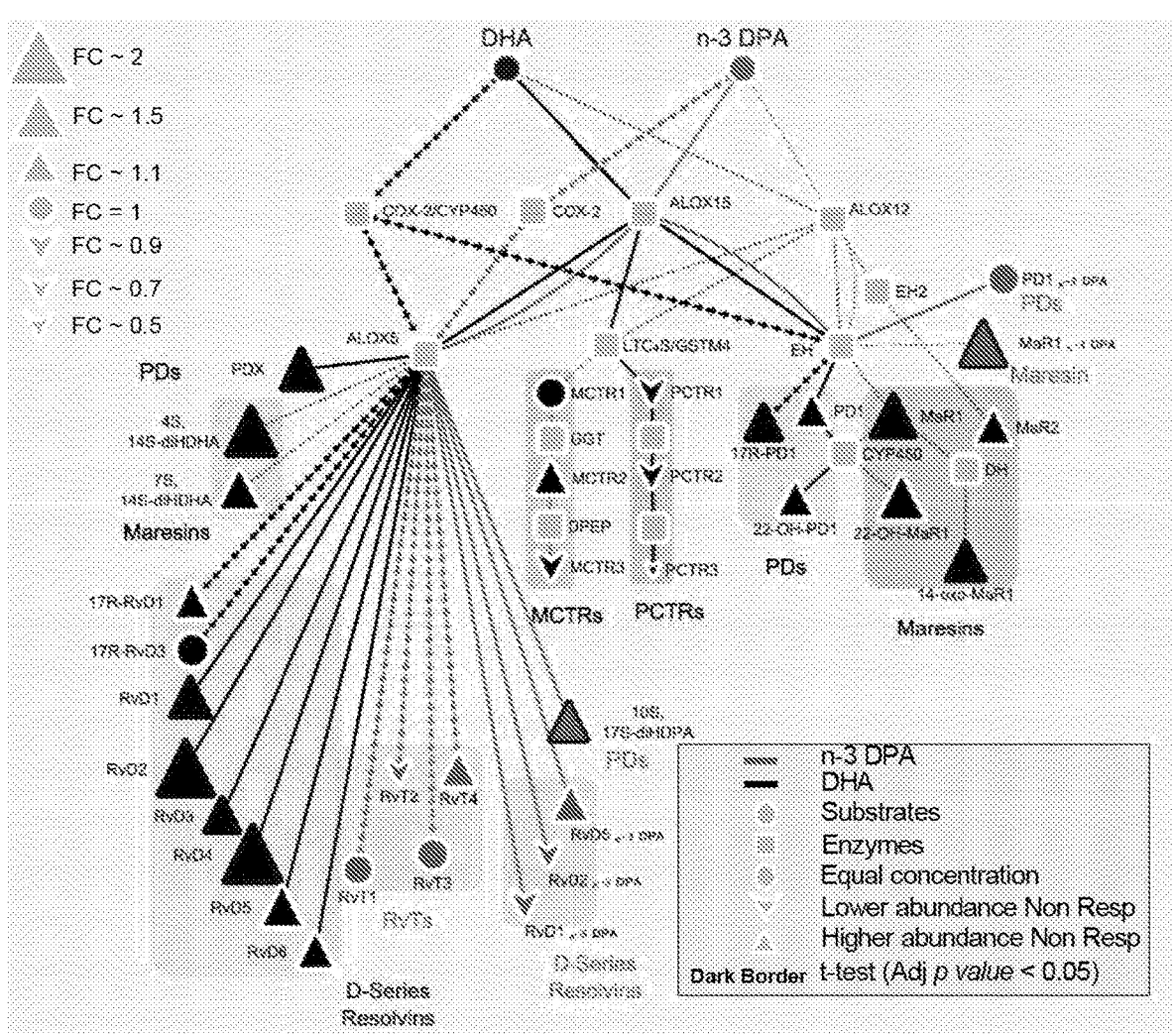
Figure 2:
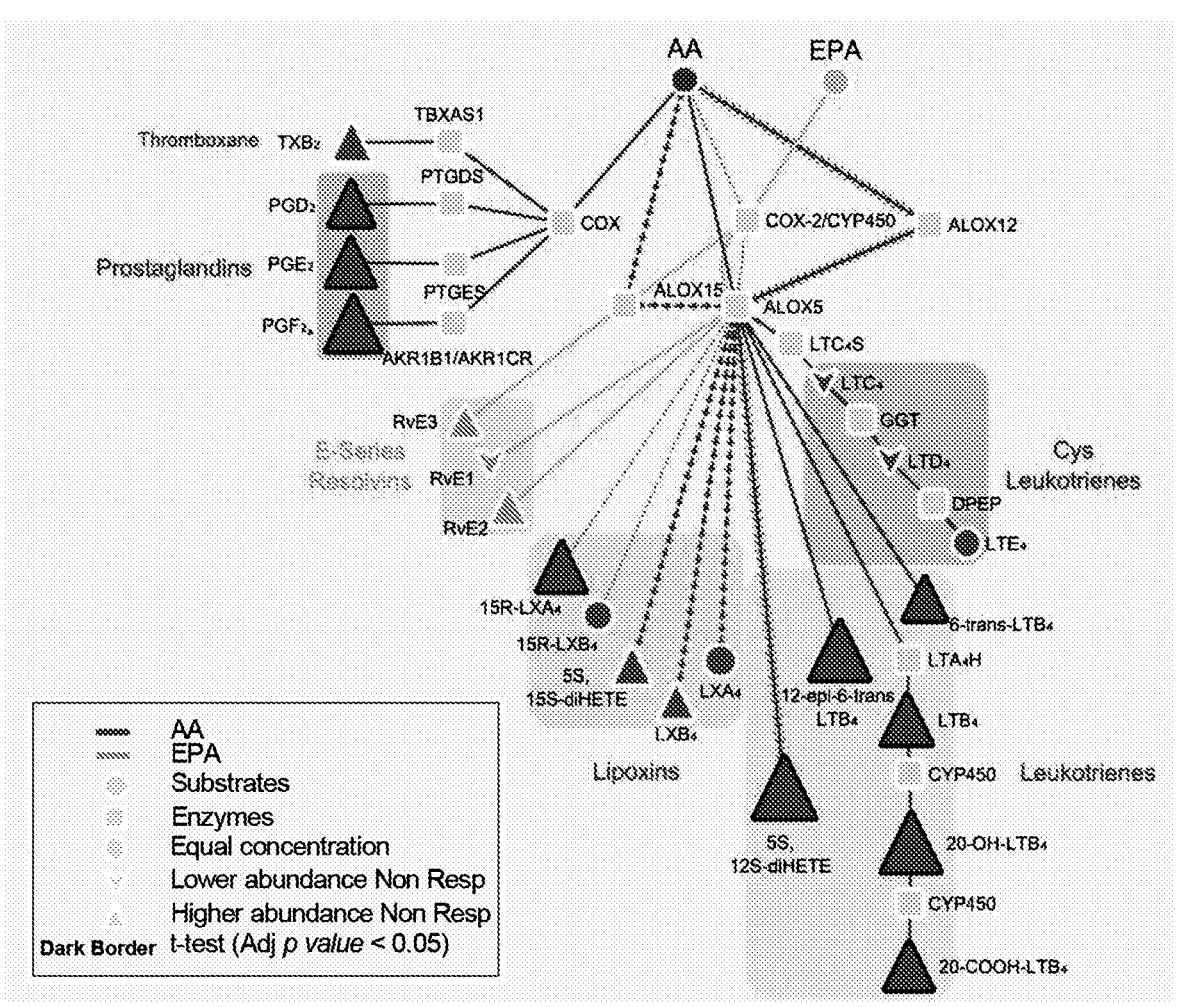

FIG. 2—Upregulation of baseline peripheral blood lipid mediator concentrations in DMARD-non-responders when compared with DMARD-responders.

Peripheral blood was collected in patients DMARD-responders (Resp) and DMARD-non-responders (Non-Resp) prior to DMARD treatment initiation. Peripheral blood lipid mediator profiles were established in accordance with published criteria including matching retention time and MS/MS fragmentation spectra. Pathway analysis for the differential expression of mediators from the (top panel) DHA and n-3 DPA, and (bottom panel) EPA and AA bioactive metabolomes in Non-Resp when compared to Resp. Statistical differences between the normalised concentrations (expressed as the fold change) of the lipid mediators from the Non-Resp and Resp groups were determined using a student T-test followed by a multiple comparison correction using Benjamini-Hochberg procedure. Results are representative of n=67 for Resp and n=30 Non-Resp.

Figure 3:
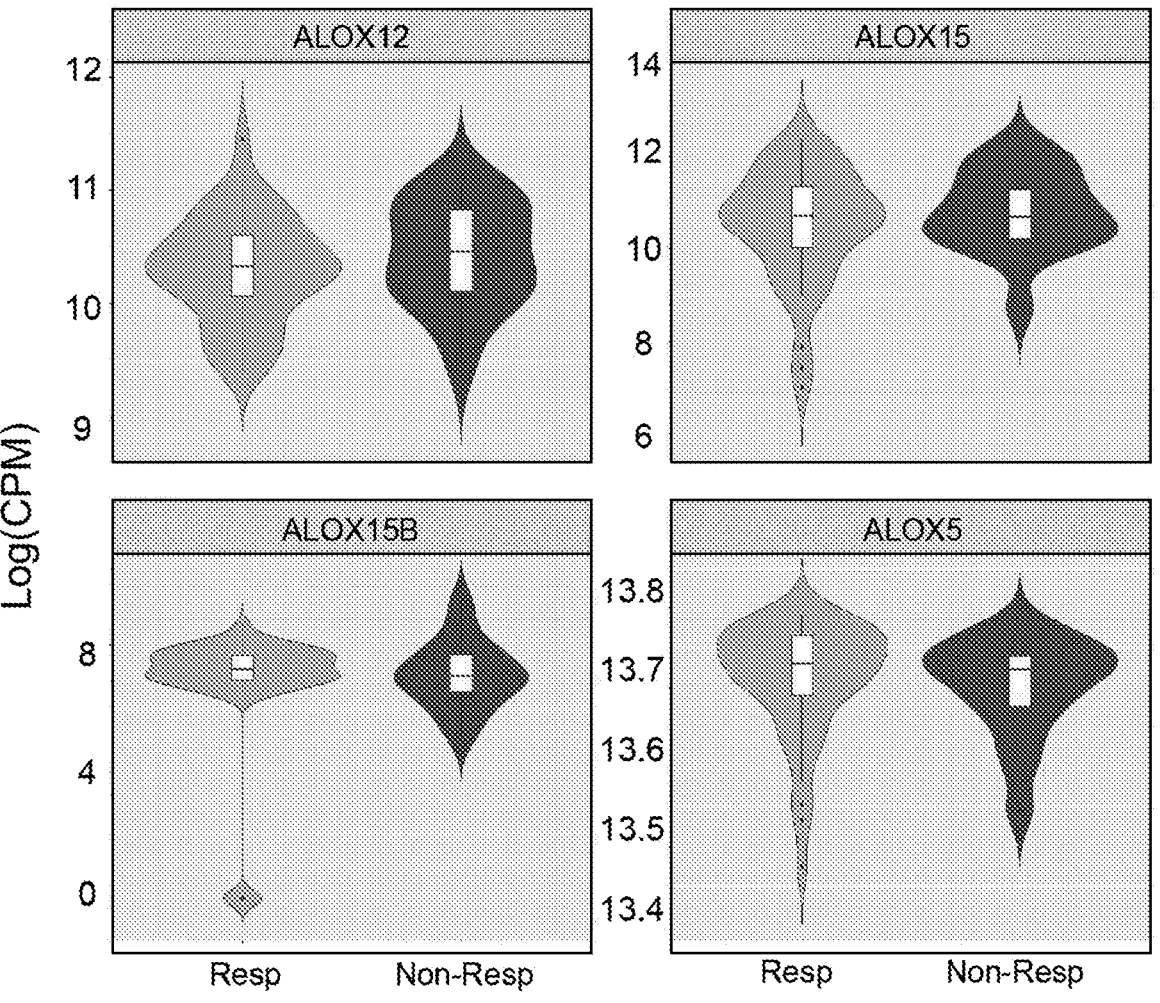

FIG. 3—Baseline expression of ALOX enzymes is essentially the same between DMARD-responders and DMARD-non-responders.

Peripheral blood was collected in patients DMARD-responders (Resp) and DMARD-non-responders (Non Resp) prior to DMARD treatment initiation and the expression of ALOX enzymes was assessed. RNA count normalization and differential gene expression analysis were performed using the quasi-likelihood method of the Bioconductor R package "edgeR". The data is expressed as the logarithm of counts per million (Log(CPM)), which indicates the number of reads mapping to a gene scaled by the number of reads you sequenced times one million. Results are representative of n=43 for Resp and n=15 for Non-Resp.

Figure 4:
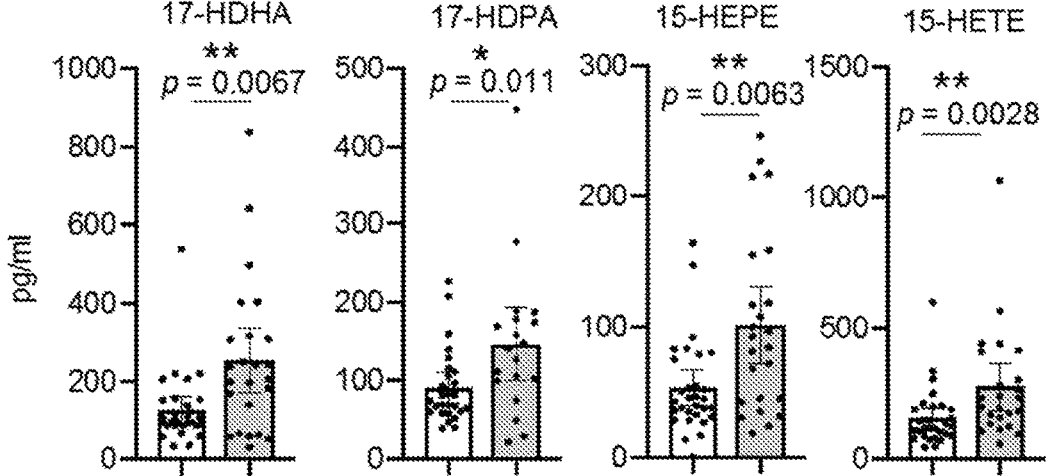
Figure 4:
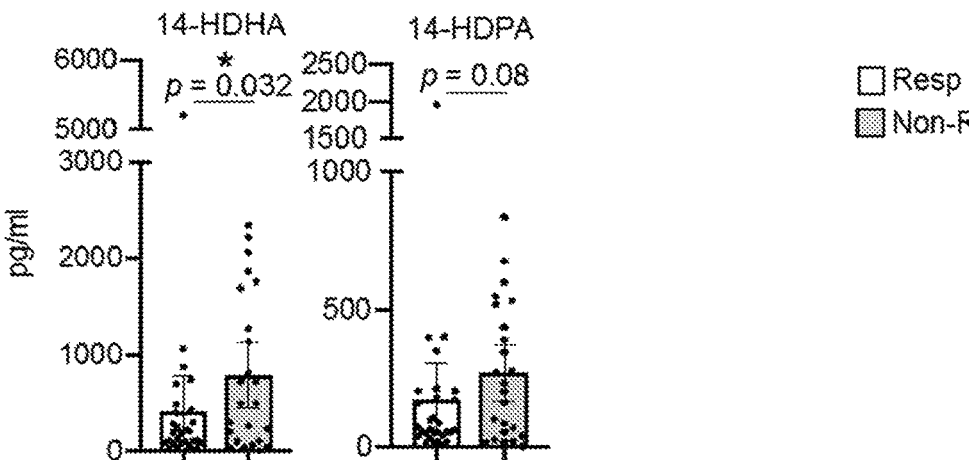
Figure 4:
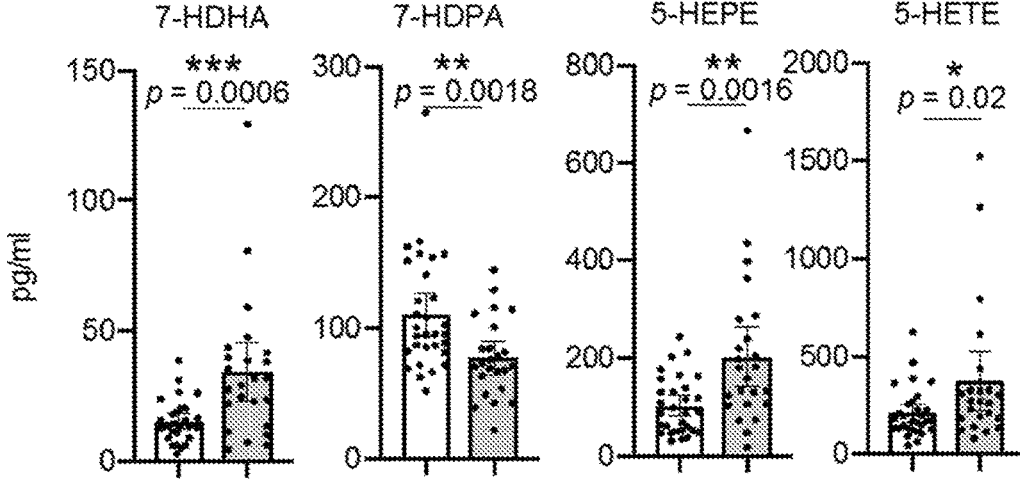

FIG. 4— Upregulation of ALOX5, ALOX12 and ALOX15 products from all four essential fatty acid metabolomes in plasma from non-responders when compared with responders prior to DMARD treatment initiation.

Plasma was collected from RA patients prior the initiation of DMARD treatment and the activity of ALOX5 (7-HDHA, 7-HDPA, 5-HEPE and 5-HETE), ALOX12 (14-HDHA, and 14-HDPA) and ALOX15 (17-HDHA, 17-HDPA, 15-HEPE and 15-HETE) was investigated using LC-MS/MS based lipid mediator profiling. Results are expressed as mean with 95% Cl. * p<0.05 using Mann-Whitney Test. N=30 for DMARD-responders (Resp) and 24 for DMARD-non-responders (Non-Resp).

FIG. 5—Combining disease pathotypes together with select SPM concentrations enhances the predictiveness of the machine learning model. Plasma was collected from RA patients prior to the initiation of treatment with DMARD and lipid mediator concentrations established using LC-MS/MS based lipid mediator profiling. (A,B) PLS-DA analysis of peripheral blood lipid mediator concentrations for Lympho-myeloid (Lymphoid), Diffuse-myeloid (Myeloid) and Pauci-immune-fibroid (Fibroid) pathotypes. (A) 3-dimensional score plot. (B) Variable importance in projection (VIP) scores of 15 lipid mediators with the greatest differences in concentrations between the three groups. Results are representative of n=18 for Fibroid n=17 for Myeloid and n=19 for Lymphoid. (C) Pathway analysis for the differentially expressed mediators from the DHA and n-3 DPA bioactive metabolomes in DMARD non-responders (Non-Resp) when compared to DMARD responders (Resp) for each pathotype. Statistical differences between the normalised concentrations (expressed as the fold change) of the lipid mediators from the Non-Resp and Resp groups were determined using student t-test followed by a multiple comparison correction using Benjamini-Hochberg procedure. Results are representative of n=19 for Fibroid Resp, n=9 for Fibroid Non-Resp, n=19 for Lymphoid Resp, n=8 for Lymphoid Non-Resp, n=22 for Myeloid Resp, n=9 for Myeloid Non-Resp (D) Classification accuracies for each class (sensitivity and specificity) of RvD4, 10S, 17S-diHDPA, 15R-LXA$_4$ and MaR1$_{n-3\ DPA}$ model created using the specific dataset for the different pathotypes (fibroid, lymphoid and myeloid). Green indicates the samples that were predicted as Resp while blue indicates predicted Non-Resp. Percentages indicate true positives (Resp class) and true negatives (Non-Resp class). All the models were created using the random forest methodology ("randomForest" package from R).

Figure 6:
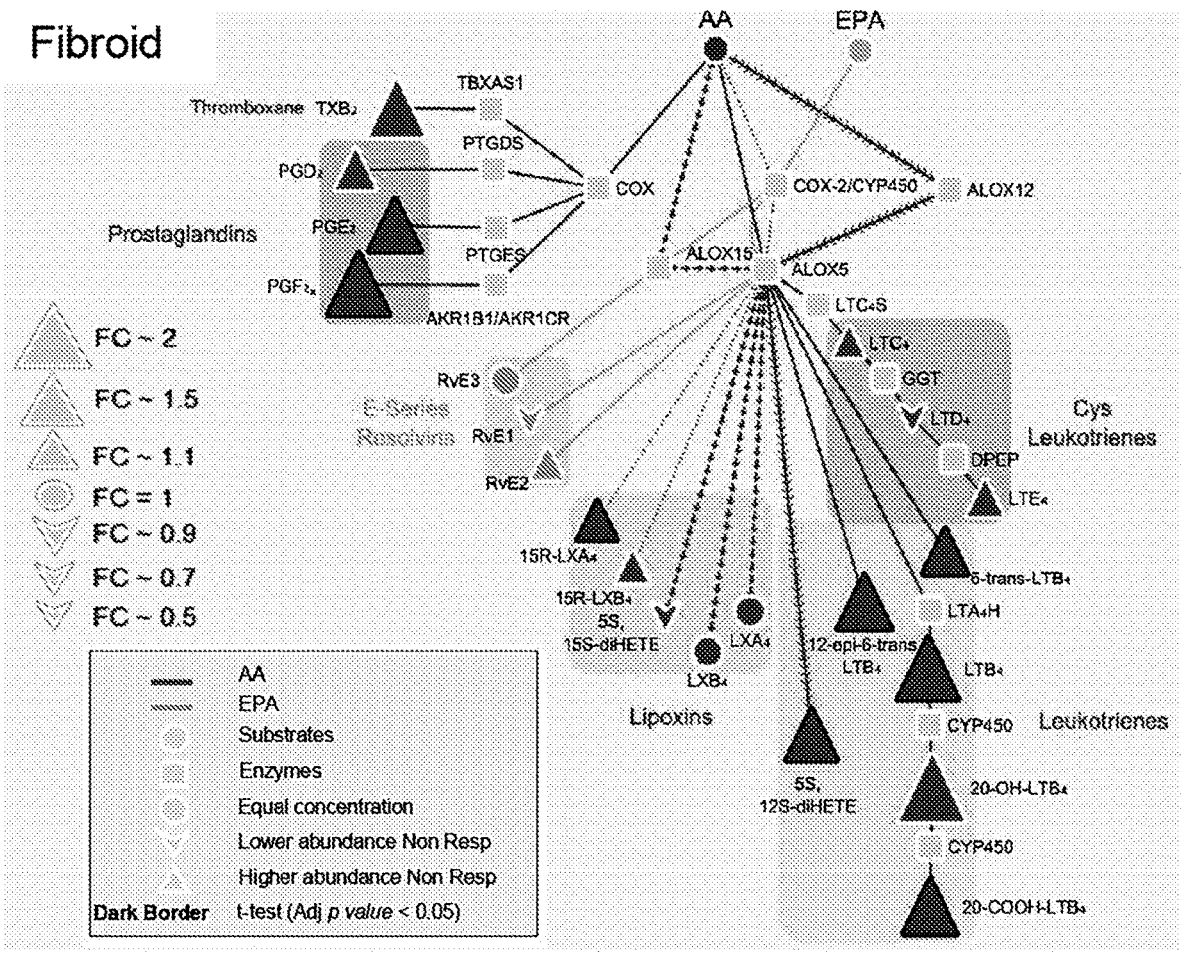
Figure 6:
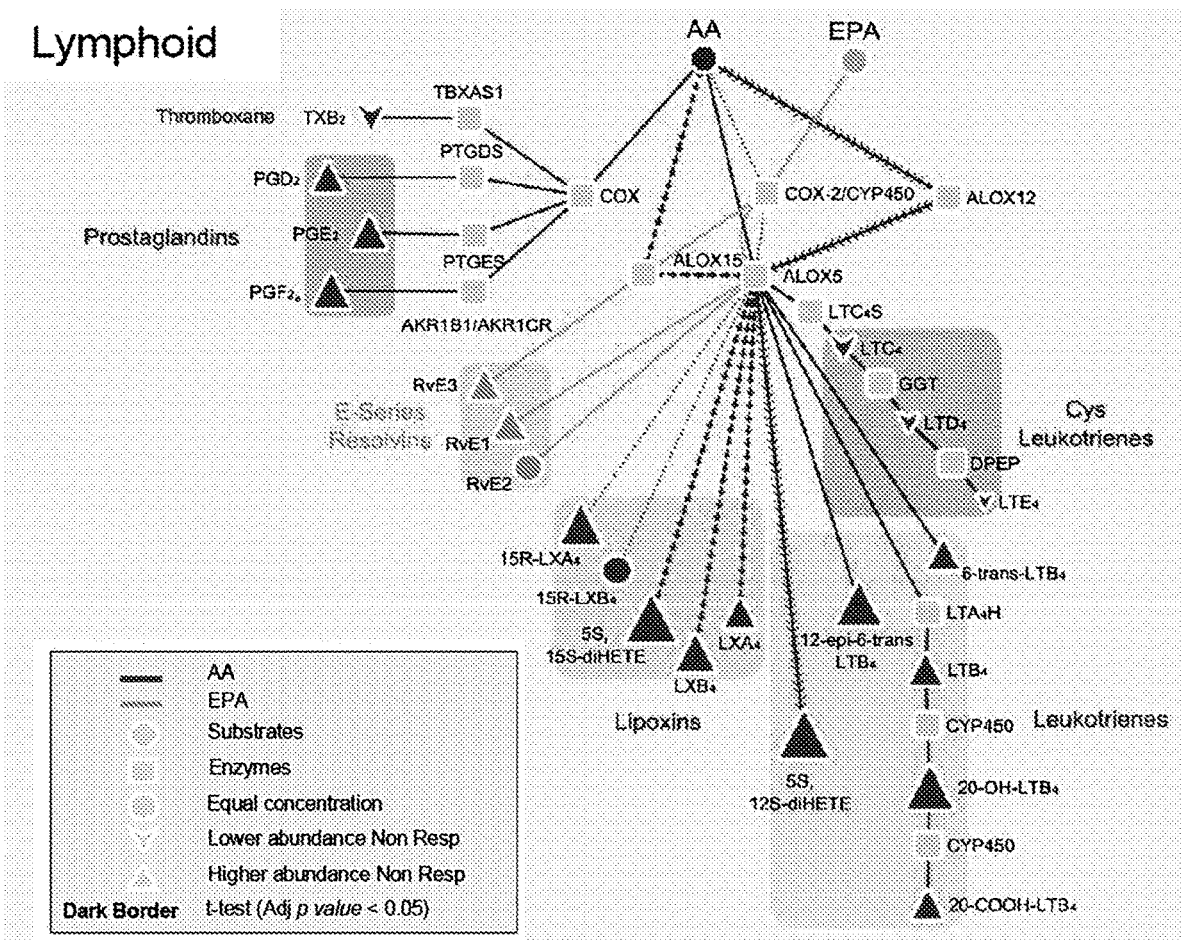
Figure 6:
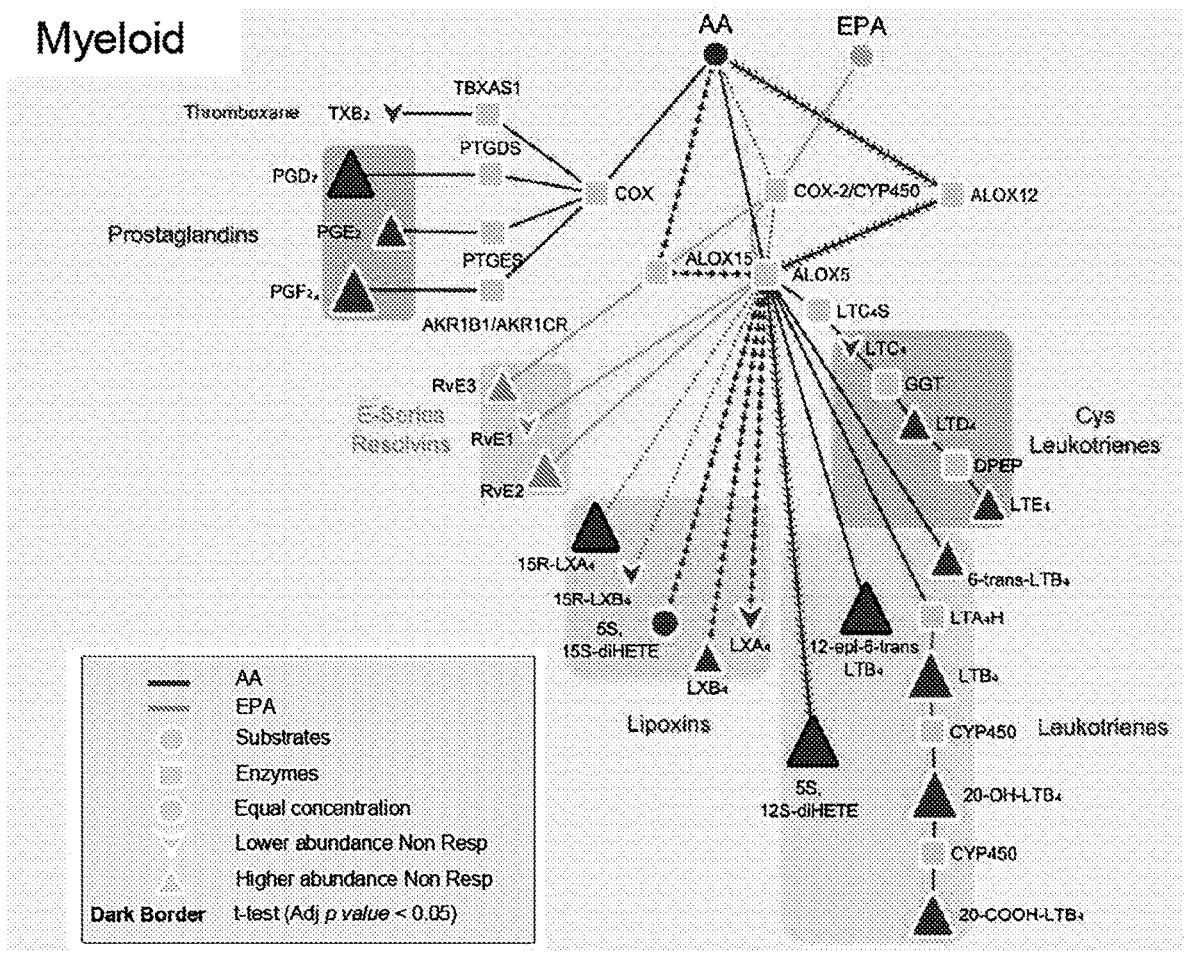

FIG. 6— Differential regulation of AA and EPA metabolomes in peripheral blood of DMARD-responders and DMARD-non-responders from patients with distinct pathotypes.

Plasma was collected from RA patients prior the initiation of DMARD treatment. Lipid mediators were identified and quantified using LC-MS/MS based lipid mediator profiling and the differential expression of mediators from the AA and EPA metabolomes was analysed for each RA pathotype in DMARD-non-responders (Non-Resp) when compared to DMARD-responders (Resp). Results are representative of n=19 for Fibroid Resp, n=9 for Fibroid Non-Resp, n=19 for Lymphoid Resp, n=8 for Lymphoid Non-Resp, n=22 for Myeloid Resp, n=9 for Myeloid Non-Resp.

Figure 7:
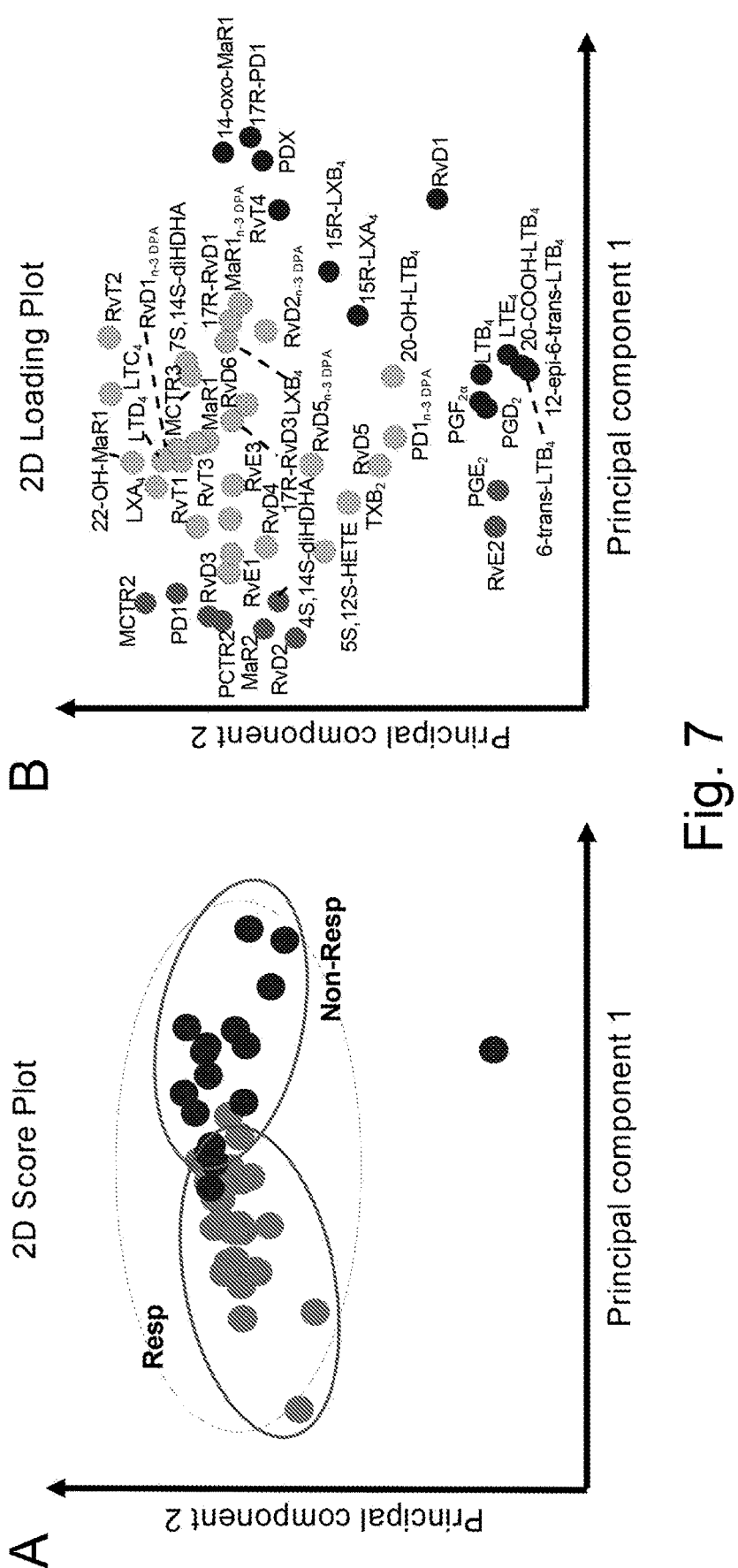
Figure 7:
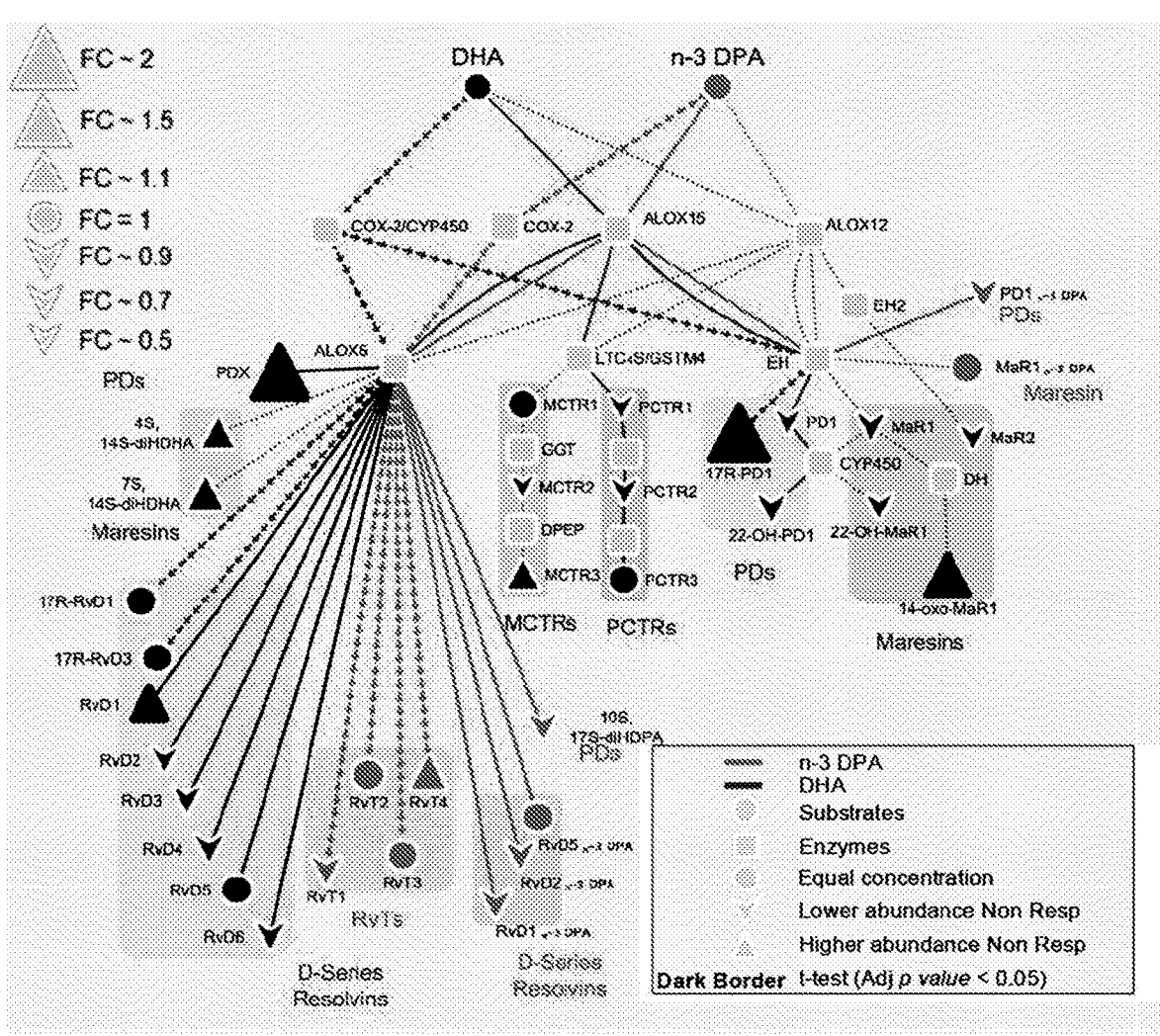
Figure 7:
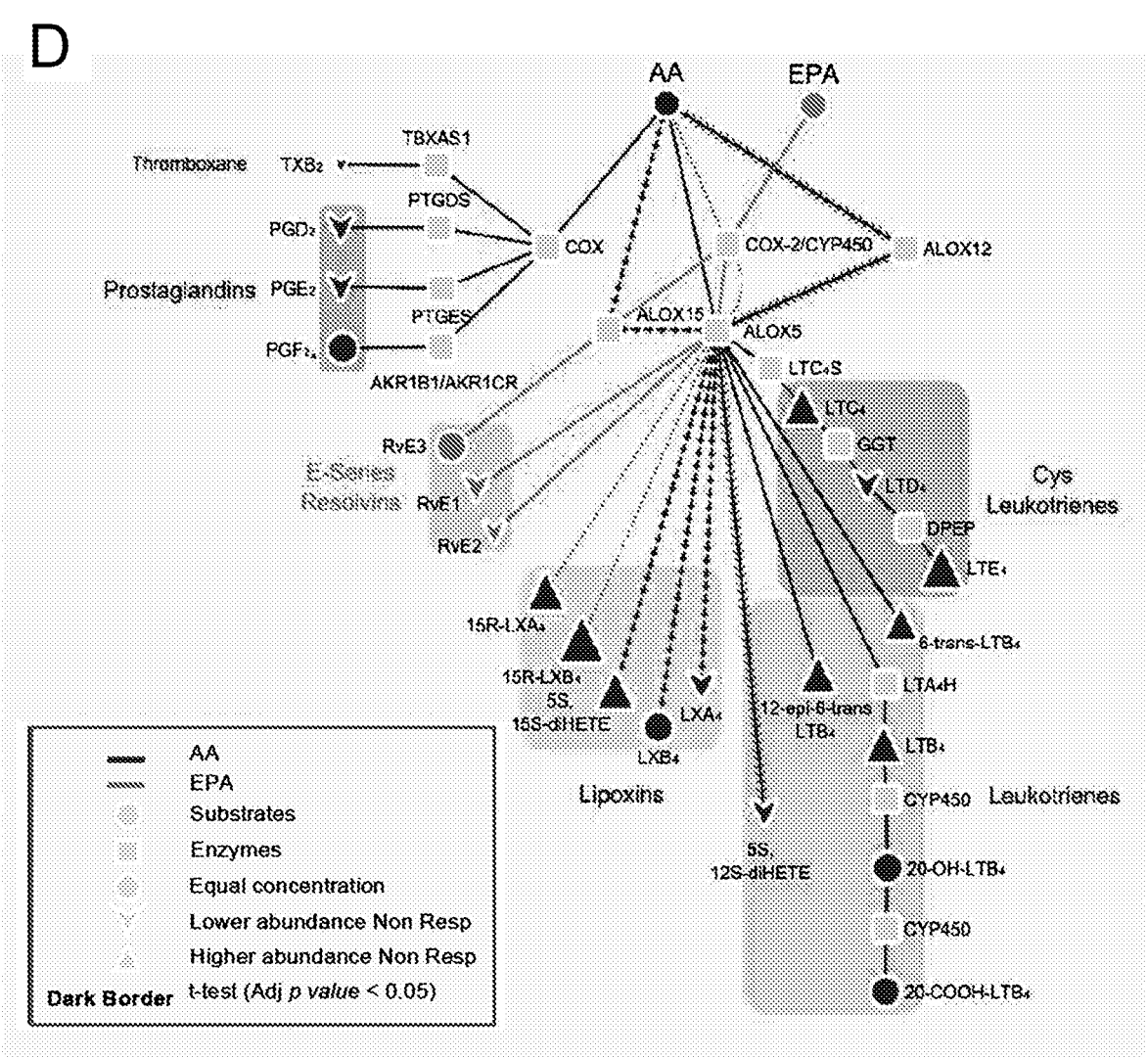

FIG. 7— Decreased peripheral blood SPM concentrations in DMARD non-responders when compared with DMARD responders 6 months after treatment initiation. Peripheral blood was collected in patients that displayed reduced joint disease (DMARD responders, Resp) and those that did not (DMARD non-responders; Non Resp) 6 months after treatment initiation. Peripheral blood lipid mediator profiles were established using LC-MS/MS based lipid mediator profiling. (A,B) OPLS-DA of lipid mediator profiles from Resp and Non-Resp. (A) Score plot, (B) Represents the loading plot with mediators displaying VIP score greater than 1 highlighted in dark-grey or black and correspond with either Resp or Non-Resp respectively. (C-D) Pathway analysis for the differential expression of mediators from the (C) DHA and n-3 DPA and (D) EPA and AA bioactive metabolomes in Non-Resp when compared to Resp. Statistical differences between the normalised concentrations (expressed as the fold change) of the lipid mediators from the Non-Resp and Resp groups were determined using a student t-test followed by multiple comparison correction using Benjamini-Hochberg procedure. Results are representative of n=27 for Resp and n=17 for Non-Resp.

Figure 8:
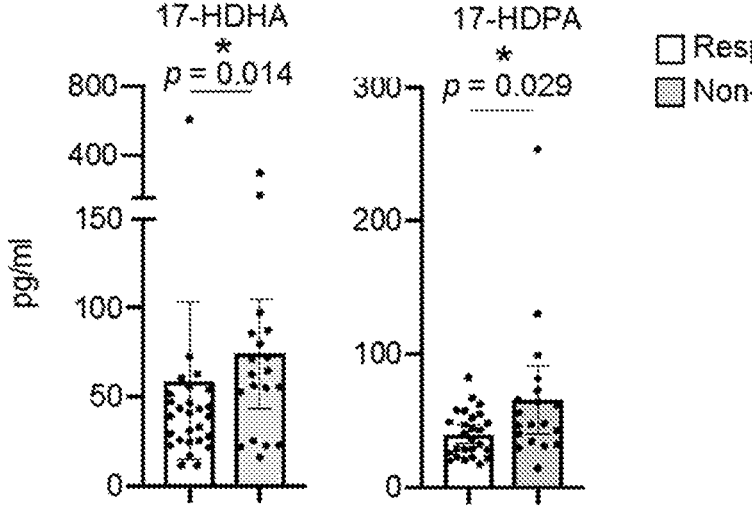
Figure 8:
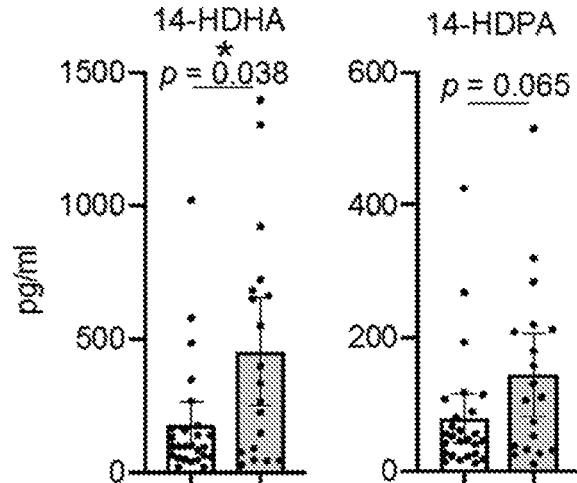
Figure 8:
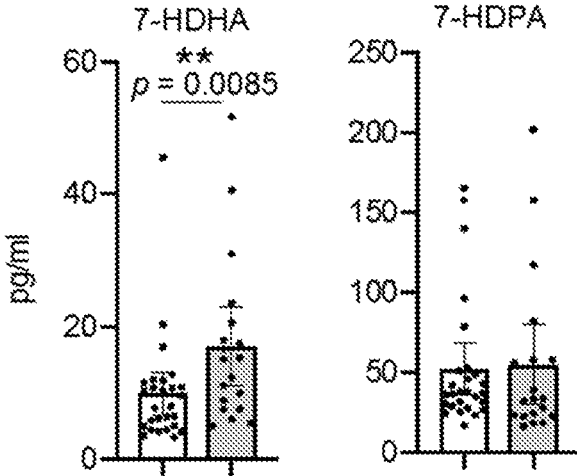

FIG. 8— Upregulation of ALOX5, ALOX12 and ALOX15 products from the DHA and n-3 DPA metabolomes in plasma from DMARD-non-responders when compared with DMARD-responders 6 months after DMARD treatment initiation.

Plasma was collected from RA patients 6 months after the initiation of DMARD treatment and the activity of ALOX5 (7-HDHA and 7-HDPA), ALOX12 (14-HDHA and 14-HDPA) and ALOX15 (17-HDHA and 17-HDPA) was investigated using LC-MS/MS based lipid mediator profiling. Results are expressed as mean with 95% Cl. * p<0.05 using Mann-Whitney Test. N=30 for DMARD-responders (Resp) and 24 for DMARD-non-responders (Non-Resp).

Figure 9:
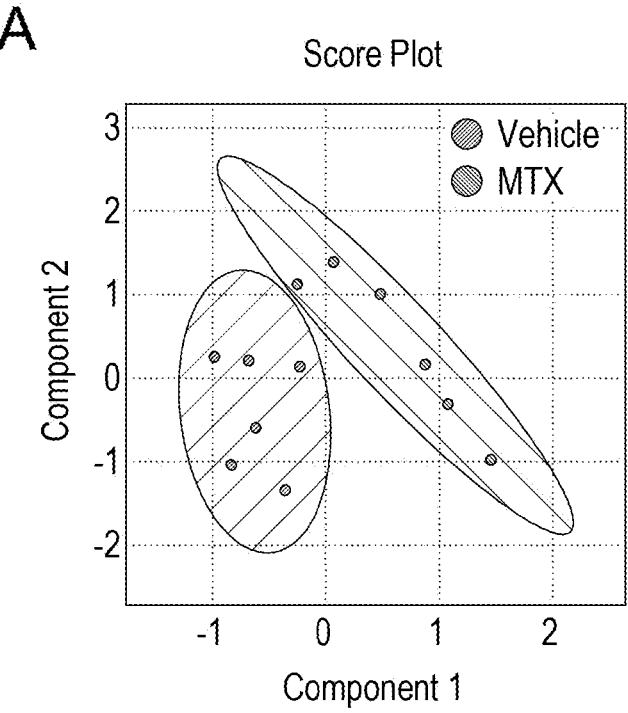
Figure 9:
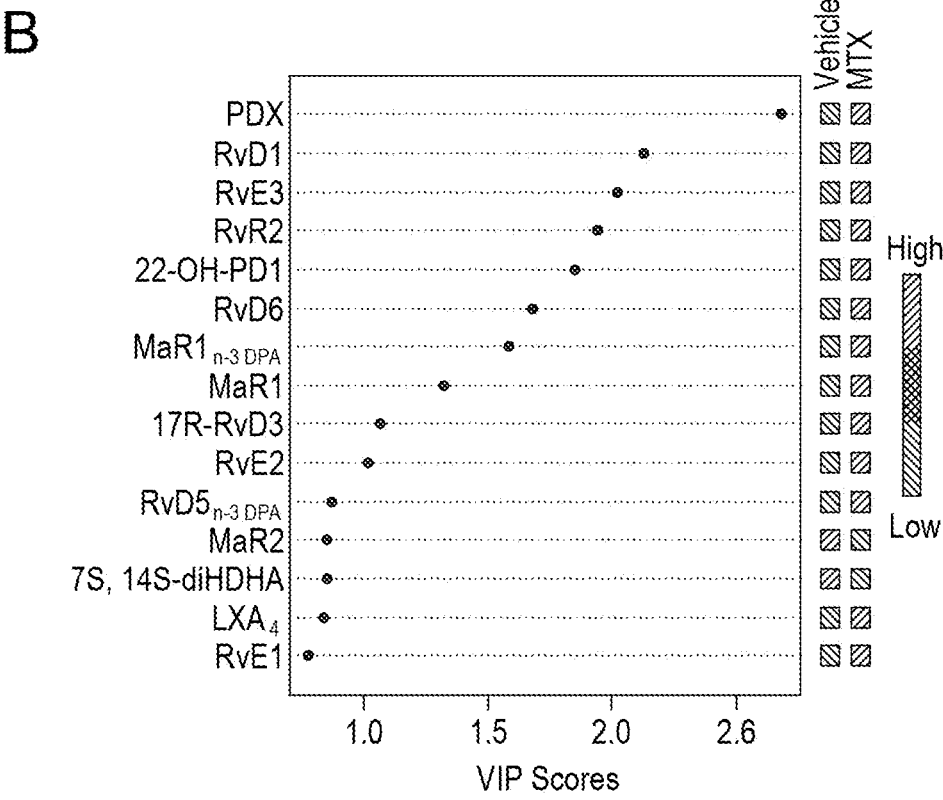
Figure 9:
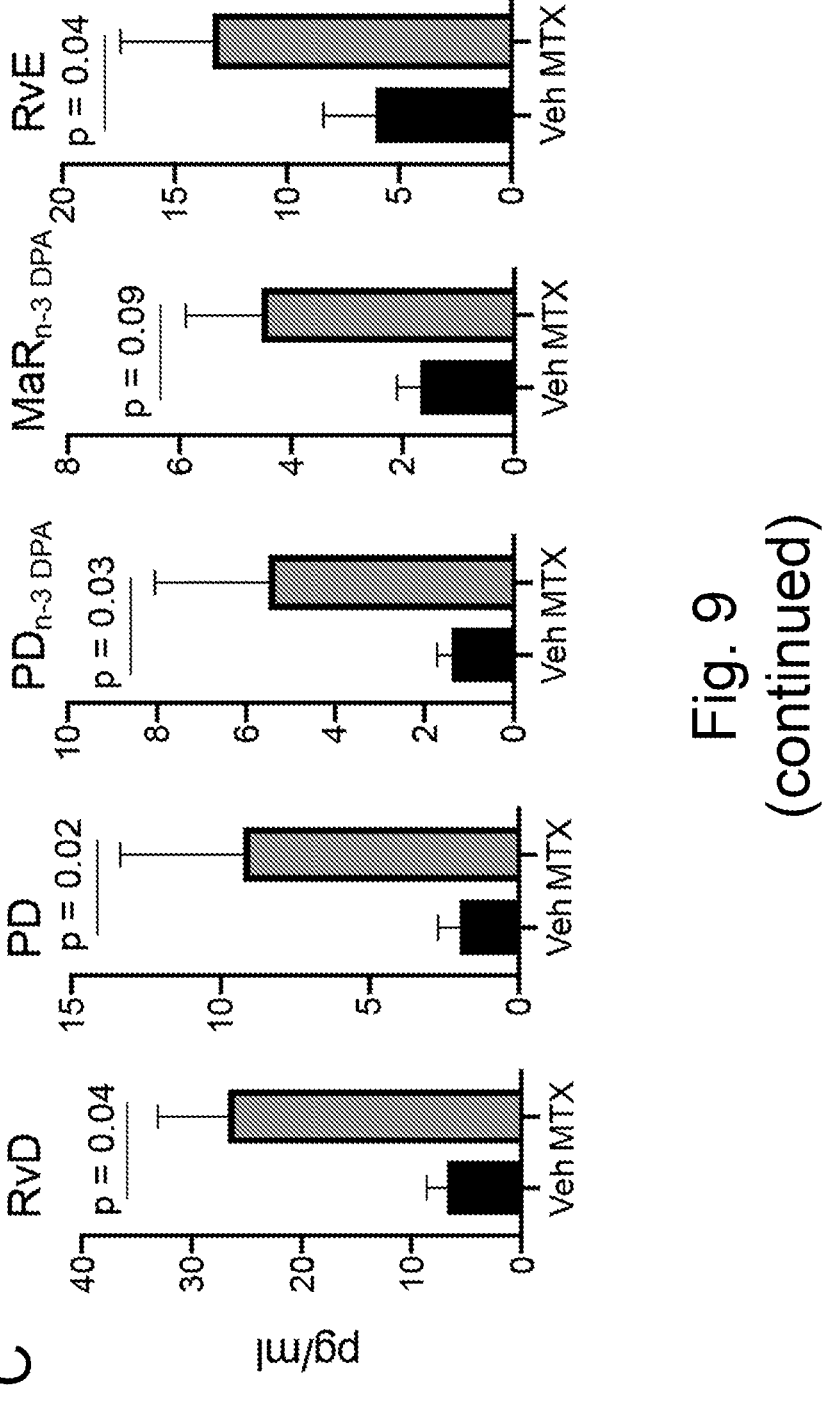
Figure 9:
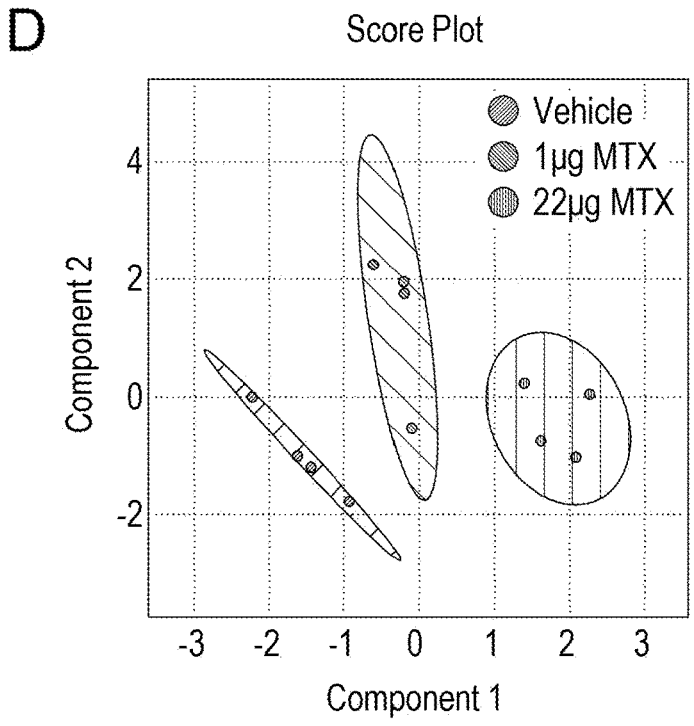
Figure 9:
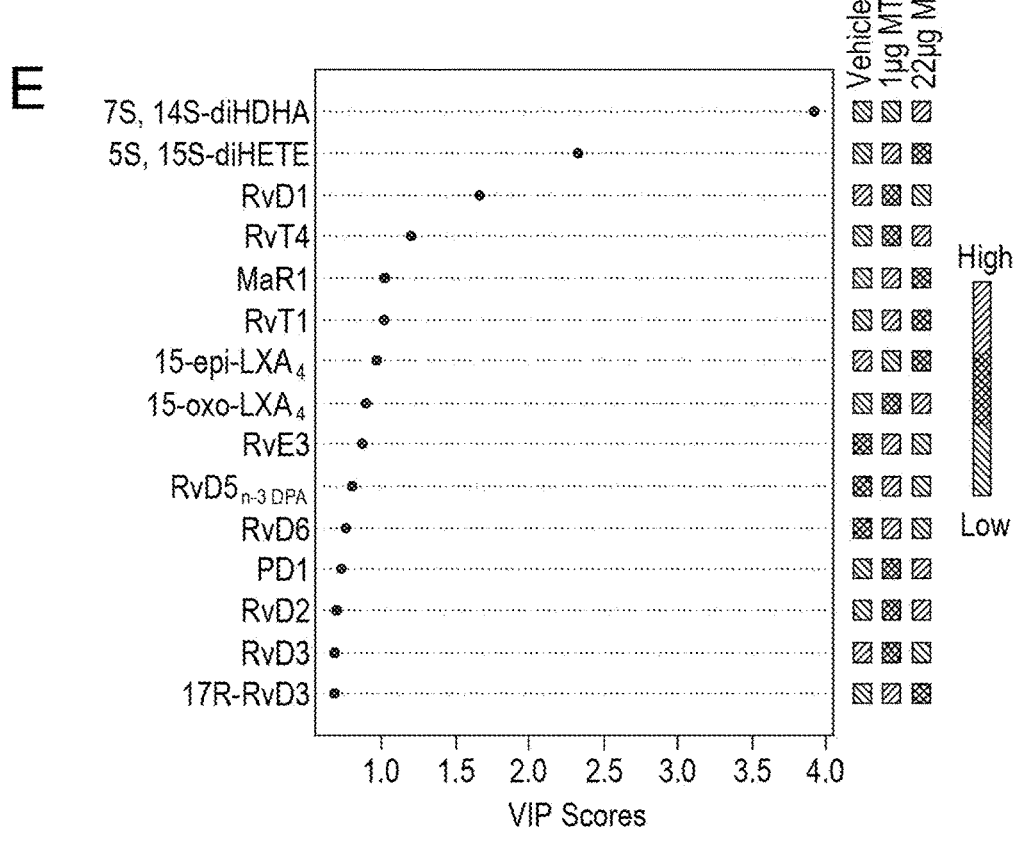

FIG. 9— MTX upregulates SPM formation in human peripheral blood. Human healthy volunteer peripheral blood was incubated with or without 100 nM of MTX (37° C., 45 min). Plasma was obtained by centrifugation and peripheral blood SPM concentrations were determined using LC-MS/ MS based lipid mediator profiling. (A) OPLS-DA analysis of plasma SPM concentrations. Colored spherical areas display 95% confidence region of respective incubations. (B) Variable importance in projection (VIP) scores of 15 lipid mediators with the greatest differences in concentrations between the two groups. (C) Cumulative concentrations of lipid mediator families that were upregulated by MTX. Results for A, B are representative of n=6 donors from three distinct experiments. Results for C are mean±SEM, n=6 donors *p<0.05 vs Vehicle group using Mann-Whitney test. (D-E) Mice were administered MTX (1 μg/mouse or 22 μg/mouse) or vehicle via intravenous injection. Blood was then collected after 1 hour and SPM concentrations were determined using LC-MS/MS based lipid mediator profiling (D) oPLS-DA analysis of plasma SPM concentrations. Colored areas display 95% confidence region of respective incubations. (E) Variable importance in projection (VIP) scores of 15 lipid mediators with the greatest differences in concentrations between the three groups. Results are representative of n=4 mice per group and experiments were conducted on two distinct occasions.

Figure 10:
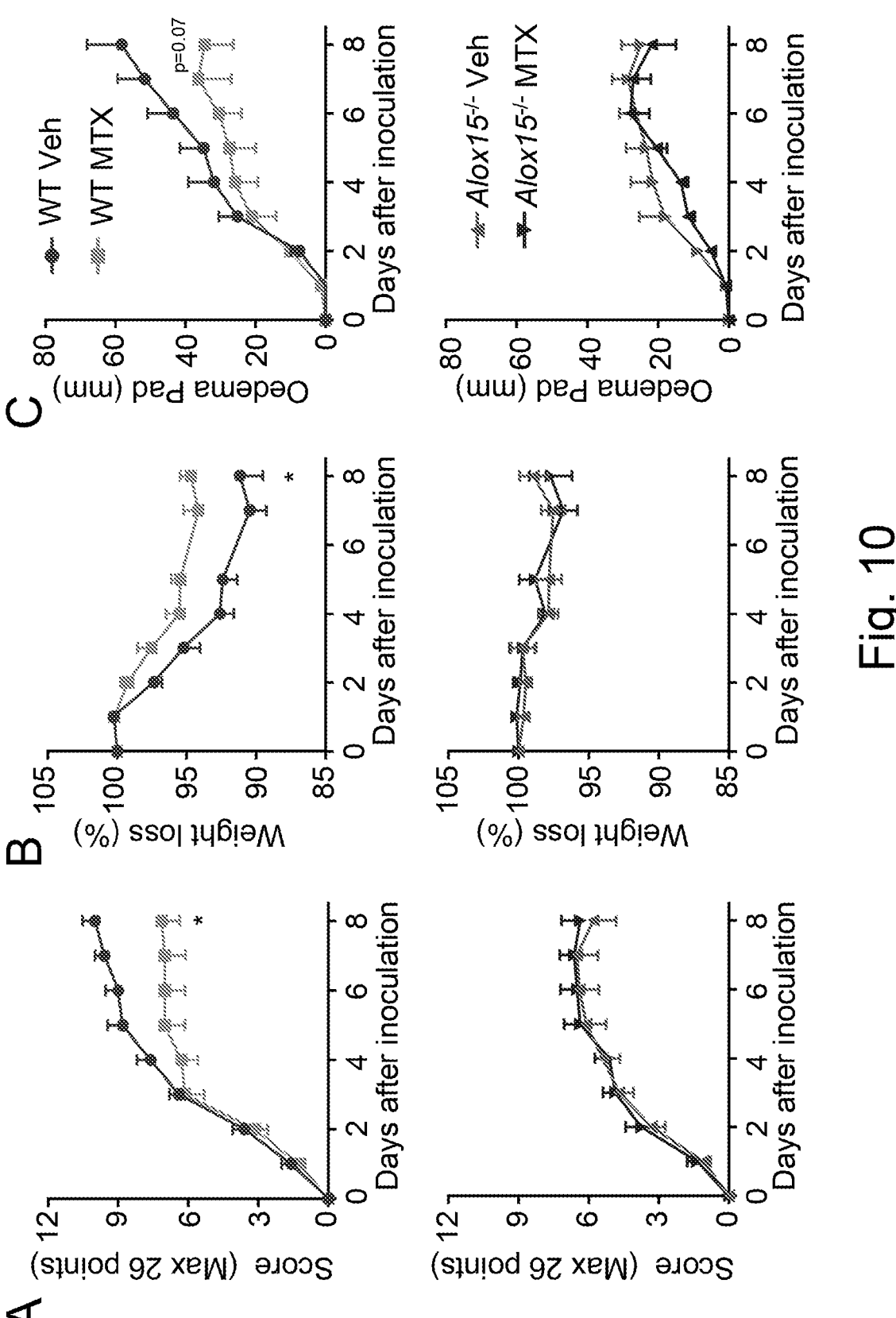
Figure 10:
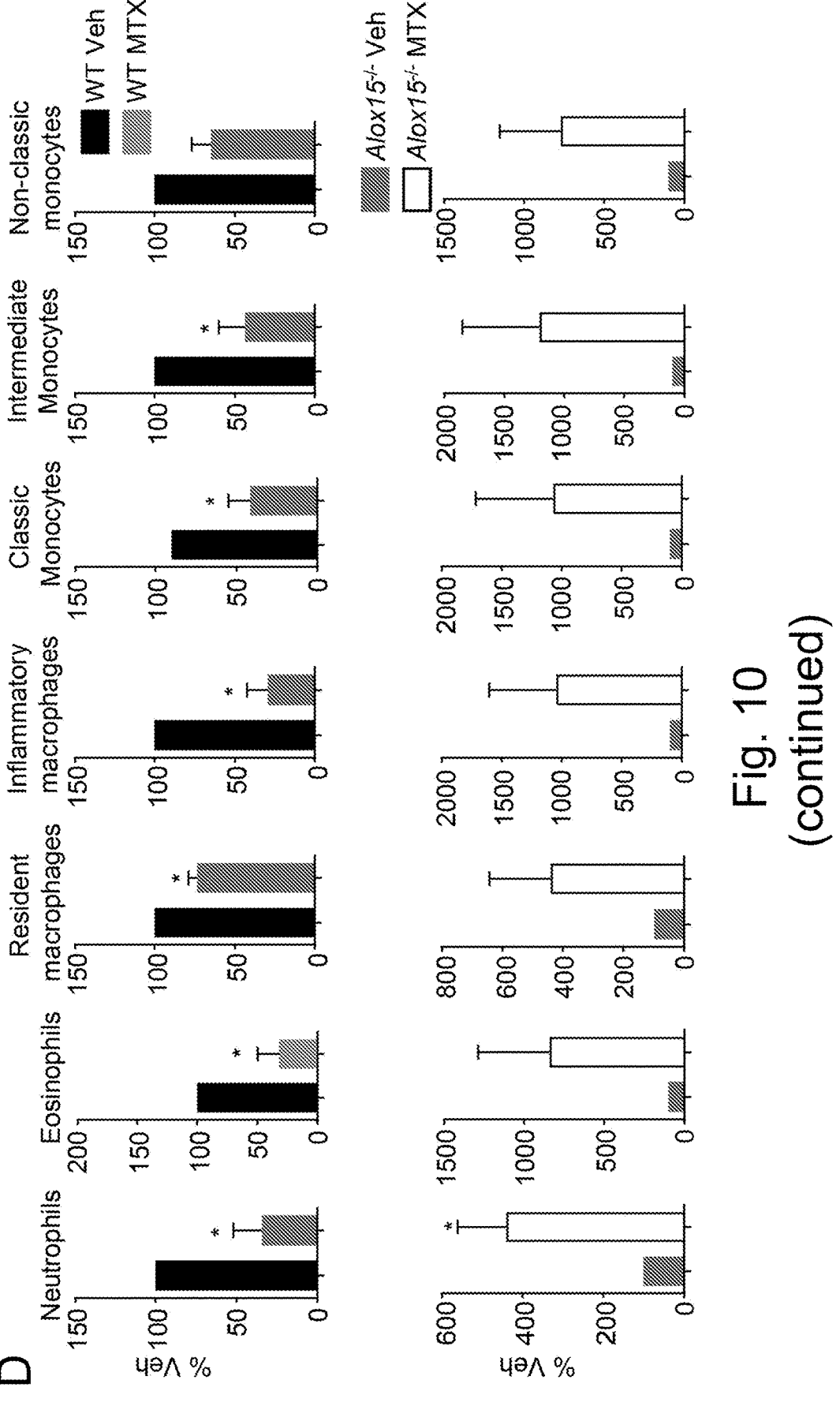

FIG. 10— Loss of ALOX15 activity reverses the protective actions of MTX in inflammatory arthritis. Inflammatory arthritis was initiated in wild type (WT) and Alox15$^{-/-}$ deficient mice by the administration of arthritogenic serum on days 0 and 2. Mice were then treated with MTX (25 mg/Kg) or Vehicle (PBS) via intraperitoneal injection on days 3, 5 and 7. Disease severity was assessed by measuring (A) disease activity using a 26-point clinical score (B) body weight and (C) paw edema. (D) Eight days post disease initiation joints were collected, leukocytes were liberated and the number of infiltrated leukocytes was determined using flow cytometry and fluorescently labelled antibodies. Results for A-C are mean±SEM and for D are percentage of vehicle n=7 mice per group. Results for D are representative of n=8 mice per group. Experiments were conducted on two distinct occasions. * p<0.05 vs Vehicle group for A-C using two-way ANOVA, for D using one-sample t test.

Figure 11:
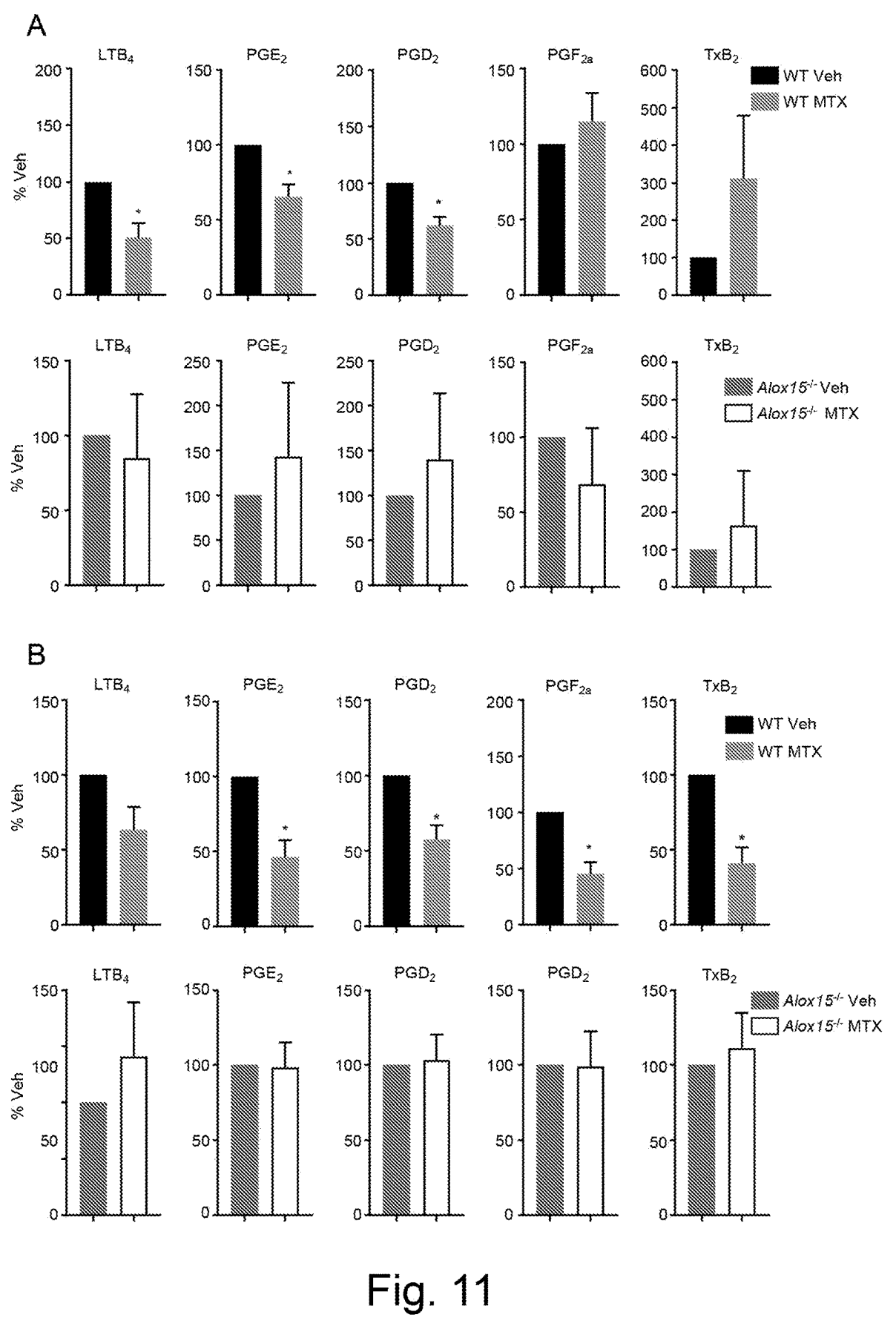

FIG. 11— MTX regulates the levels of inflammatory eicosanoids in peripheral blood and joints during inflammatory arthritis, actions that are lost in ALOX15 null mice.

Inflammatory arthritis was initiated in wild type (WT) and Alox15$^{-/-}$ mice by injecting K/BxN serum via intraperitoneal injection on days 0 and 2. MTX (25 μg/mouse) was administered on days 3, 5 and 7. Blood and joints were collected on day 8 and the concentrations of inflammatory eicosanoids in (A) plasma and (B) joints were determined using LC-MS/MS profiling. Results are presented as % of vehicle control. n=7 mice per group from two distinct experiments. * p<0.05 using one sample t-test.

Figure 12:
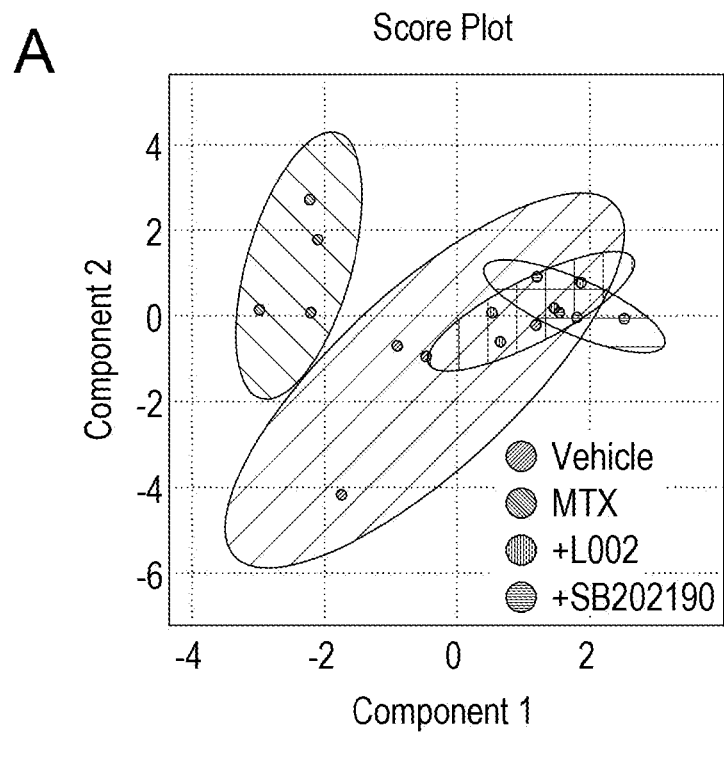
Figure 12:
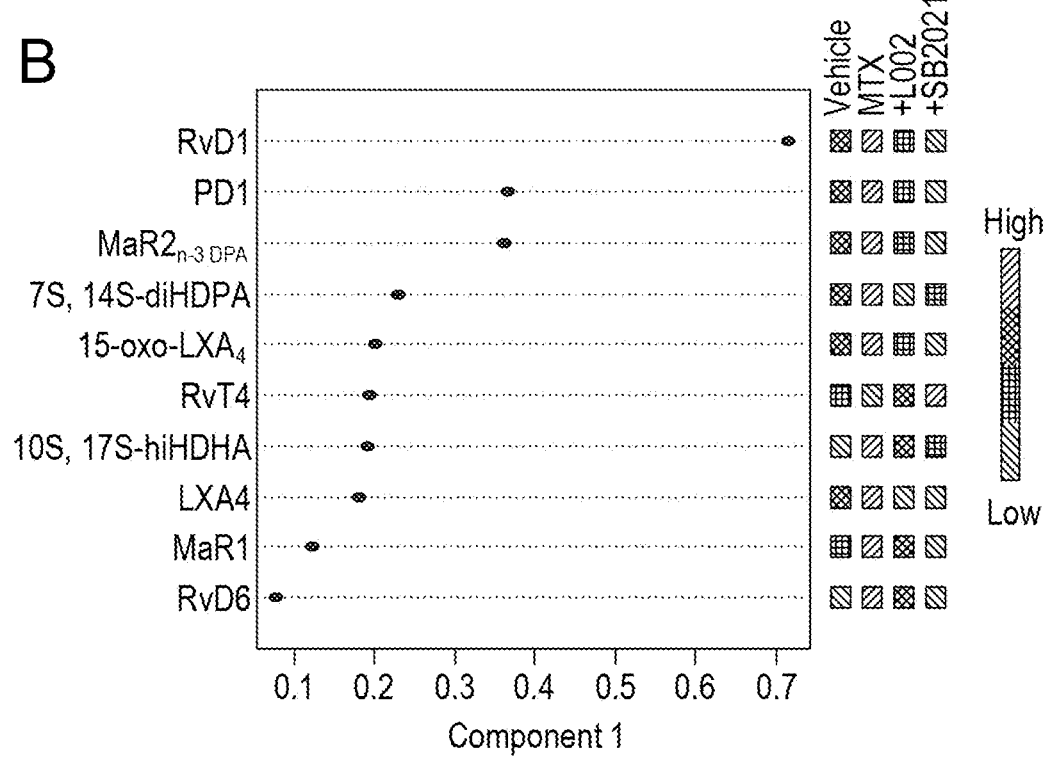
Figure 12:
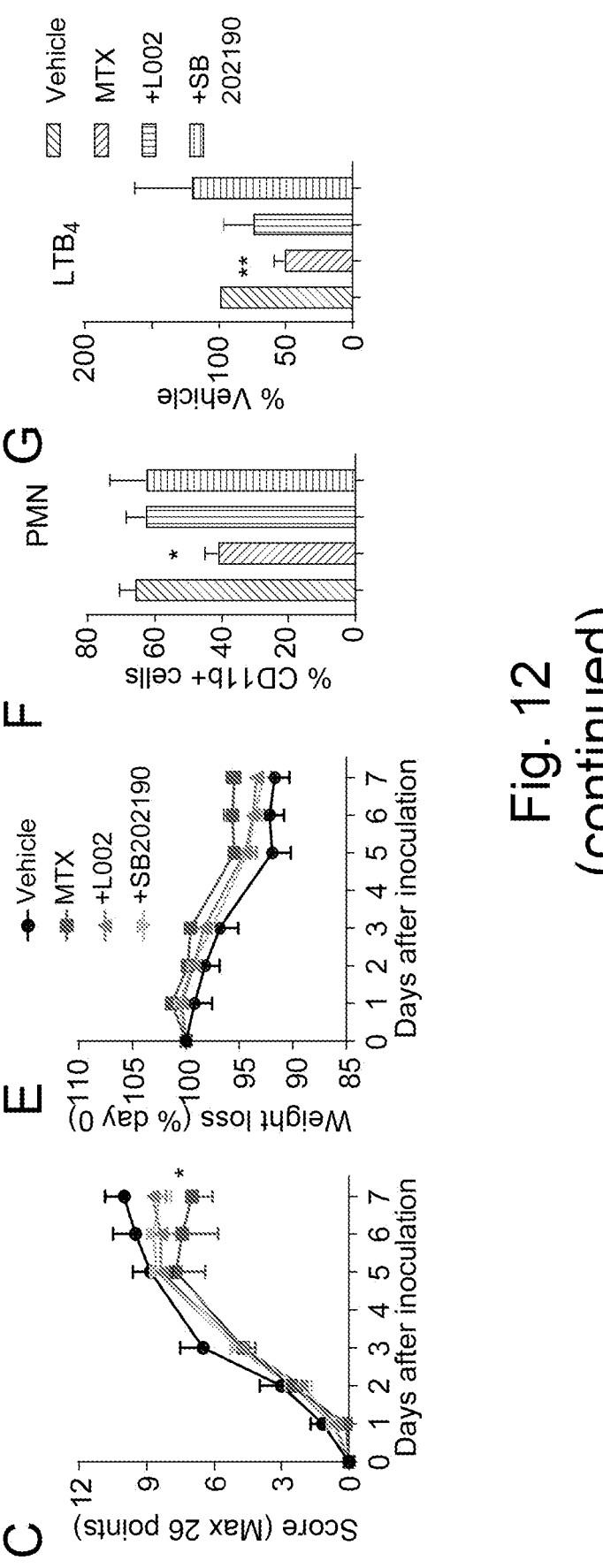
Figure 12:
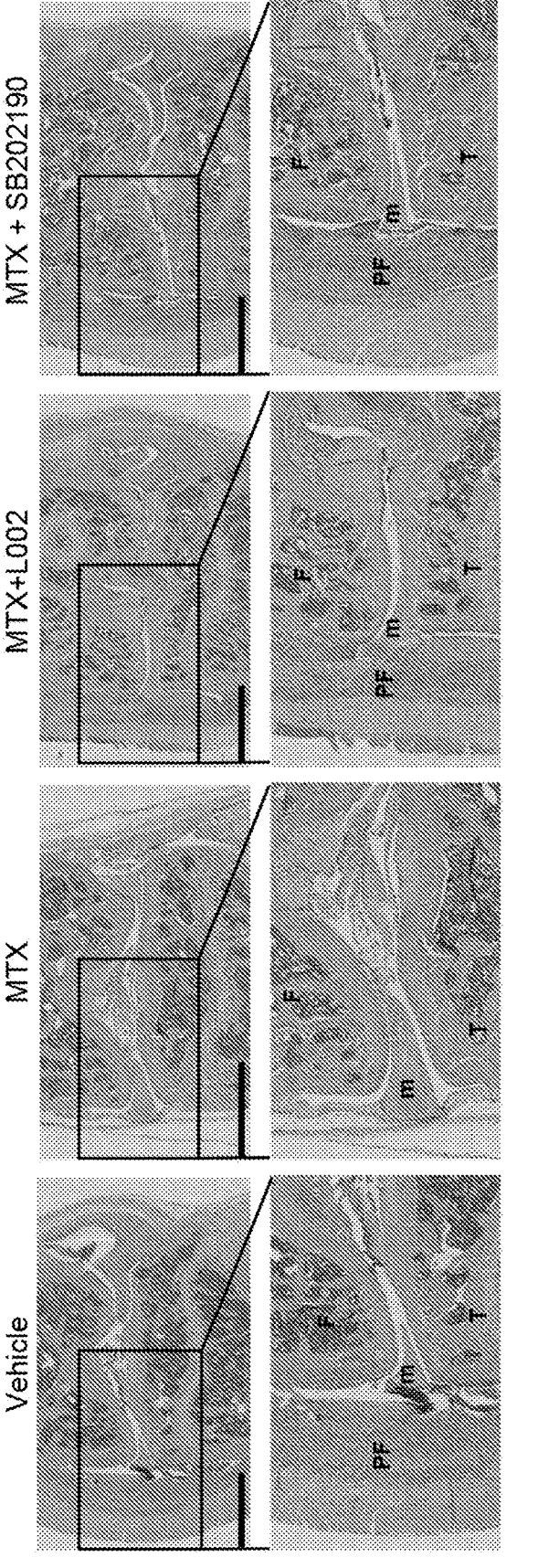

FIG. 12— Inhibition of p300 and MAPK reduces SPM biosynthesis and reverses the joint protective action of MTX in inflammatory arthritis. (A-B) Human peripheral blood was incubated with vehicle, L002 (p300 inhibitor; 2 μM) or SB202190 (MAPK inhibitor 5 μM) for 15 minutes at 37° C., then with MTX (100 nM) or vehicle (37° C., 45 min). Plasma was collected by centrifugation and SPM were identified and quantified using LC-MS/MS based lipid mediator profiling (see methods for details). (A) sPLS-DA score plot of identified lipid mediator concentrations (B) Contribution for the top 10 differentially regulated mediators in principle component 1. Results are representative of n=6 volunteers per group with experiments conducted on two distinct occasions. (C-G) Inflammatory arthritis was initiated in mice by the administration of arthritogenic serum on days 0 and 2. Mice were then treated with Vehicle (PBS), MTX (25 mg/Kg), MTX plus L002 (20 mg/Kg) or MTX plus SB202190 (20 mg/Kg) via intraperitoneal injection on days 3, 5 and 7. Disease severity was assessed by measuring (C) disease activity using a 26-point clinical score, (D) joint histology using hematoxylin and eosin staining of knee sections collected 8 days post disease initiation, original magnification=×4 and (E) body weight. (F,G) Eight days post disease initiation joints were collected, (F) leukocytes were liberated from the paws and the number of neutrophils infiltrated into the paw was determined using flow cytometry and fluorescently labelled antibodies. (G) Lipid mediators were extracted and the concentrations of LTB$_4$ were determined using liquid chromatography tandem-mass spectrometry. C, E, F are mean±SEM and G are percentage of vehicle of n=4 mice per group and experiments were conducted on two distinct occasions. Results for D are representative of n=8 mice per group. * p<0.05 vs Vehicle group for C and E using two-way ANOVA, for F one-way ANOVA, for G using one-sample t test. F=femur; m=meniscus; PF=pannus formation; T=tibia.

Figure 13:
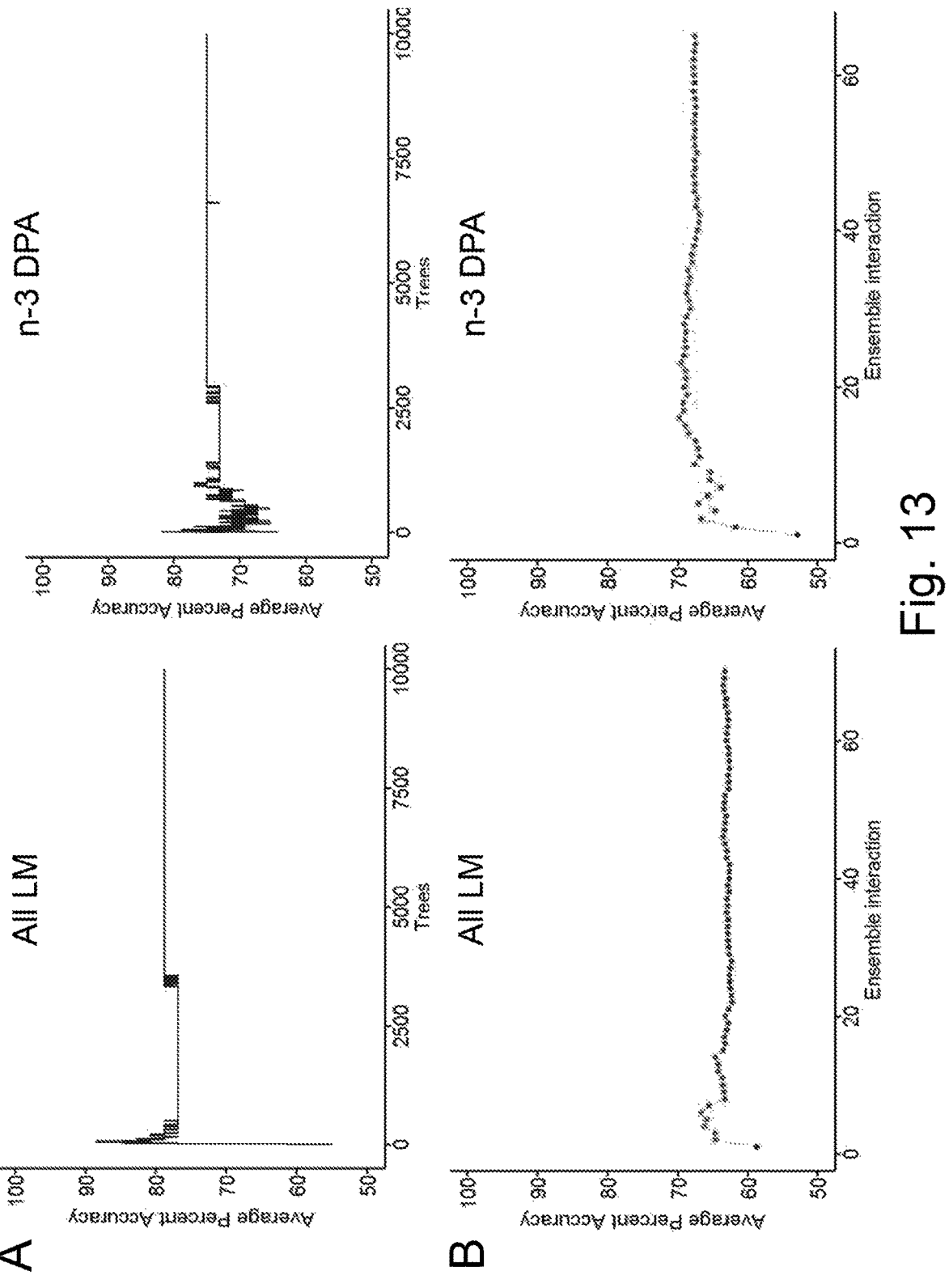

FIG. 13: Establishing the optimal parameters for RandomForest and SVM models. Representative results obtained for average percent accuracy for (A) RandomForest models and (B) SVM models by increasing the number of (A) decision trees (B) ensemble interactions.

Figure 14:
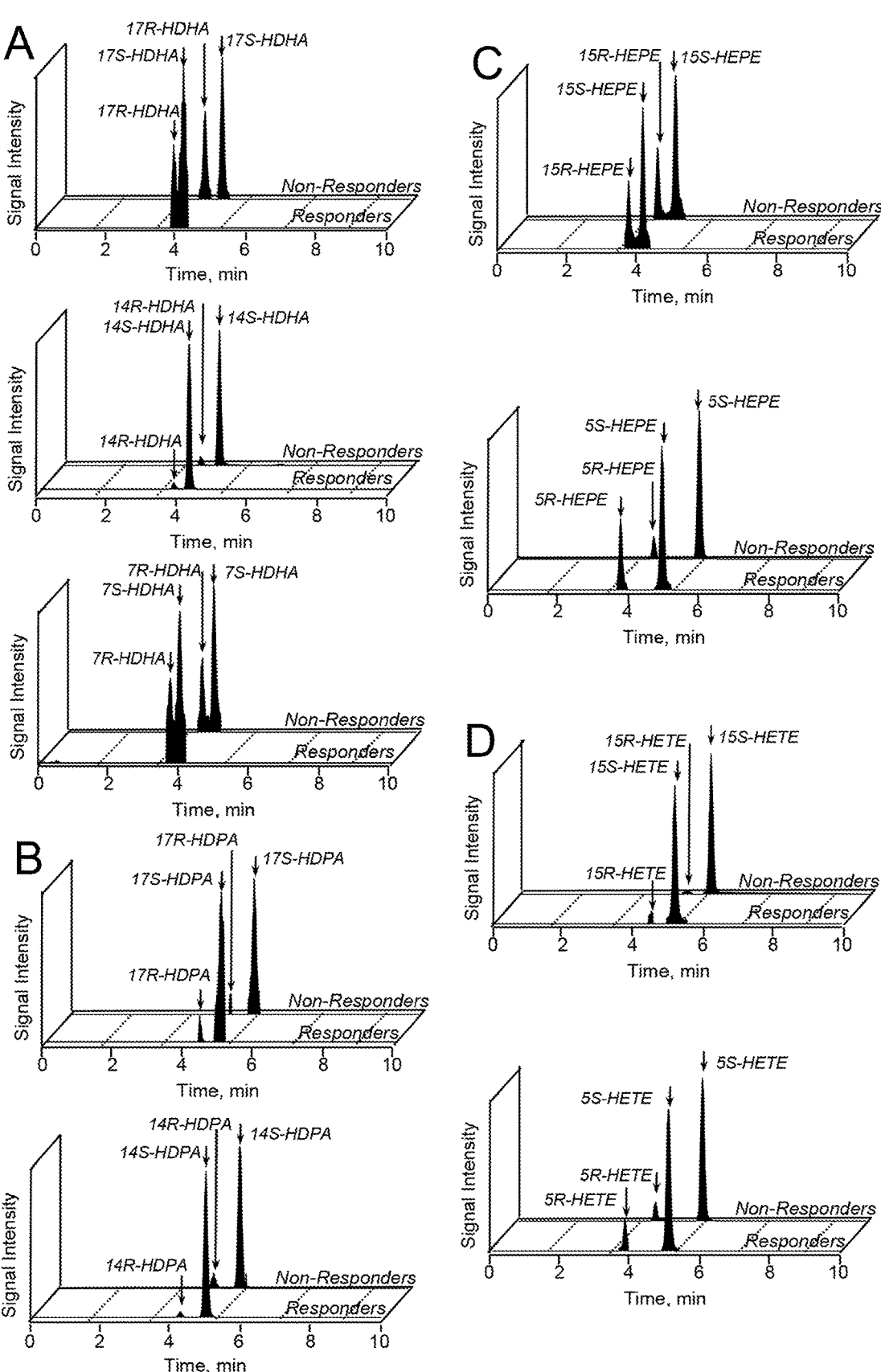

FIG. 14: Chiral chromatography of baseline plasma from DMARD responders and non-responders demonstrates higher concentrations of the S-monohydroxylated isomers. Plasma was extracted and relative abundance for each of the chiral isomers for the indicated monohydroxy fatty acids from the (A) DHA, (B) n-3 DPA, (C) EPA and (D) AA was determined without ambiguity using a chiral LC-MS/MS MRM approach. Results are representative of n=29 DMARD Responders and 22 DMARD-non-responders.

Figure 15:
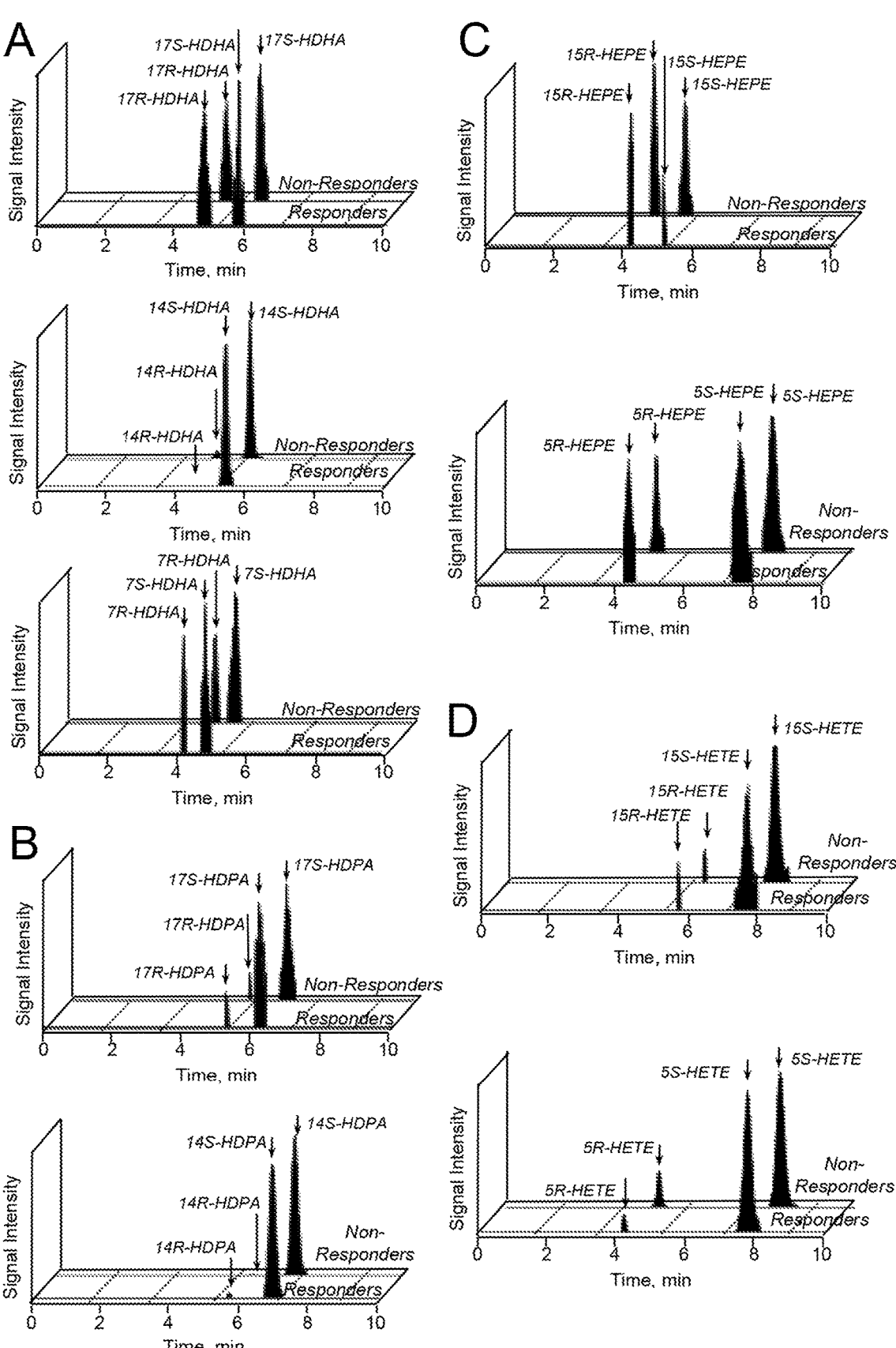

FIG. 15: Chiral chromatography of 6-month plasma from DMARD responders and non-responders demonstrates higher concentrations of the S-monohydroxylated isomers. Plasma was extracted and relative abundance for each of the chiral isomers for the indicated monohydroxy fatty acids from the (A) DHA, (B) n-3 DPA, (C) EPA and (D) AA was determined without ambiguity using a chiral LC-MS/MS MRM approach. Results are representative of n=29 DMARD Responders and 22 DMARD-non-responders.

DETAILED DESCRIPTION OF THE INVENTION

According to a first aspect, the invention provides a method of assessing the efficacy of a disease-modifying antirheumatic drug (DMARD) for use in the treatment of an inflammatory condition in a patient, which comprises measuring the levels of at least one specialized pro-resolving mediator (SPM) in samples obtained from the patient before and after administration of the DMARD, wherein an increase in the level of the at least one SPM after administration of the DMARD is indicative of efficacy of the DMARD.

Patients and Diseases

As used herein, the terms "subject" and "patient" are used interchangeably to refer to a human or a non-human mammal. The subject may be a companion non-human mammal (i.e. a pet, such as a dog, a cat, a guinea pig, or a non-human primate, such as a monkey or a chimpanzee), an agricultural farm animal mammal, e.g. an ungulate mammal (such as a horse, a cow, a pig, or a goat) or a laboratory non-human mammal (e.g., a mouse and a rat). The invention may find greatest application in connection with the treatment of human subjects.

The inflammatory condition may be rheumatoid arthritis, arthritis associated with ankylosing spondylitis, cardiovascular disease (CVD), periodontal disease, asthma, diabetes and inflammatory bowel disease (IBD), ulcerative colitis, Crohn disease or a neurological disorder such as Alzheimer's disease. The inflammatory condition may be cardiovascular disease (CVD) or rheumatoid arthritis. Preferably, the inflammatory condition is rheumatoid arthritis. In any of the embodiments herein, the subject may be a human. The subject may be a subject diagnosed with an inflammatory condition, for example Rheumatoid Arthritis. The subject may be a subject undergoing treatment for an inflammatory condition, for example Rheumatoid Arthritis.

The method advantageously allows personalisation of medicine. Because each patient will have differences in the genetics and their environment when compared to any other patient, they may respond differently to drugs, including DMARDs. If a patient is not responding to a DMARD then an alternative therapy may be needed. The method of the invention therefore allows better clinical decision making for an individual patient. The patient may be described as an "individual patent" accordingly.

Disease Modifying Anti-Rheumatic Drugs (DMARDs)

Disease modifying anti-rheumatic drugs (DMARDs) are a category of drugs. The members of this category of drugs are known to the person skilled in the art. The skilled person also knows what drugs are not DMARDs, for example, statins are not DMARDs. Statins include atorvastatin, cerivastatin, fluvastatin, lovastatin, mevastatin, pitavastatin, pravastatin, rosuvastatin and simvastatin, none of which are DMARDs. DMARDs include both biological (or "biologic") and non-biological (or "non-biologic") drugs.

Biological DMARDs include etanercept, adalimumab, infliximab, certolizumab pegol, and golimumab, which are all part of a class of drugs called tumor necrosis factor (TNF) inhibitors, and a variety of other agents with different targets, including anakinra, abatacept, rituximab, and tocilizumab.

Non-biological DMARDs include methotrexate, aspirin, hydroxychloroquine and leflunomide. Another common non-biological DMARDs is sulfasalazine. Less frequently used non-biological DMARDs include gold salts, azathioprine, and cyclosporine. The DMARD may therefore be selected from the group consisting of methotrexate, aspirin, hydroxychloroquine, leflunomide, sulfasalazine, gold salts, azathioprine, and cyclosporine. The DMARD may be selected from the group consisting of methotrexate, aspirin, hydroxychloroquine, leflunomide and sulfasalazine. The DMARD may be selected from the group consisting of methotrexate, aspirin, hydroxychloroquine and leflunomide. The DMARD may be methotrexate.

Known details concerning some frequently used non-biological DMARDs are provided below. In each case, a problem with non-biological DMARD treatment may be the need for patient monitoring, toxicity and side effects.

Methotrexate

Methotrexate was originally used as a chemotherapy treatment for cancer. When used in much lower doses for rheumatoid arthritis and other rheumatic diseases, methotrexate works to reduce inflammation and to decrease joint damage. It is taken weekly (on the same day each week) as a pill, liquid, or injection. Methotrexate may be combined with other DMARDs or with a biologic agent if methotrexate alone does not adequately control disease.

Common side effects include upset stomach and mouth sores. Methotrexate can rarely interfere with the bone marrow's production of blood cells. Low blood cell counts can cause fever, infections, swollen lymph nodes, and easy bruisability and bleeding. Liver function problems can occur, even with low doses, and therefore regular blood tests are necessary for anyone taking methotrexate. People using methotrexate should also limit alcohol use because of the increased risk of liver injury with this combination. Rare injury to the lung can occur, and methotrexate should be stopped if the person develops a new cough and shortness of breath. Women should not become pregnant while taking methotrexate.

Proper monitoring is critical to identify drug toxicity in people taking methotrexate. Testing is performed prior to starting treatment to evaluate baseline blood counts and check kidney and liver function. These tests are repeated every 4 to 6 weeks for the first few months then every 8 to 12 weeks thereafter. The dose of methotrexate can be modified if problems are noted. Anyone taking methotrexate should take folic acid (1 mg daily) or folinic acid (5 mg weekly) to reduce the risk of certain side effects, such as upset stomach, mouth sores, low blood cell counts, and abnormal liver function.

Sulfasalazine

Sulfasalazine is used in the treatment of rheumatoid arthritis and of arthritis associated with ankylosing spondylitis and inflammatory bowel disease (ulcerative colitis and Crohn disease). It is not clear how sulfasalazine works. It may be combined with other DMARDs if a person does not respond adequately to one medication. It is taken as a pill two times per day, and it is usually started at a low dose and is increased slowly to minimize side effects.

Side effects of sulfasalazine include changes in blood counts, nausea or vomiting, sensitivity to sunlight, skin rash, and headaches. People who are allergic to sulfonamide medications, such as sulfamethoxazole-trimethoprim (sample brand names: Bactrim, Septra), may have a cross-reaction to sulfasalazine and should therefore not take it. Periodic blood tests are recommended to monitor the blood count on a regular basis.

Sulfasalazine is a yellow-orange colour; people who take it may notice that their urine, tears, and sweat develop an orange tinge, which can stain clothing and contact lenses. Its important to drink plenty of fluids while taking sulfasalazine and to avoid taking it on an empty stomach or with antacids.

Hydroxychloroquine

Hydroxychloroquine, originally developed as a treatment for malaria, was later found to improve symptoms of arthritis. It can be used early in the course of rheumatoid arthritis and is often used in combination with other DMARDs. It is also very frequently used for treatment of systemic lupus erythematosus. It can be combined with steroid medications to reduce the amount of steroid needed. It is usually taken in pill form once or twice per day.

Taking a high dose of hydroxychloroquine for prolonged periods of time may increase the risk of damage to the retina of the eye, although high doses are not usually required for treatment of rheumatic conditions. An eye examination by an ophthalmologist is recommended before starting treatment and periodically thereafter. It is common to have an eye check-up done once each year.

Leflunomide

Leflunomide inhibits production of inflammatory cells to reduce inflammation. It is often used alone but may be used in combination with methotrexate for people who have not responded adequately to methotrexate alone or together with a biologic agent. It is taken by mouth once daily.

Side effects include rash, temporary hair loss, abnormal liver function tests, nausea, diarrhea, weight loss, abdominal pain, and neuropathy (nerve damage). High blood pressure can occur in up to 10 percent of people. Testing for prior exposure to hepatitis and regular blood testing while on therapy are needed to monitor for liver damage and other toxicities. Women should not become pregnant while taking leflunomide or while it is still detectable in the body.
Azathioprine Azathioprine has been used in the treatment of cancer, rheumatoid arthritis, lupus, and a variety of other inflammatory illnesses since the 1950s. It has also been used in organ transplantation to prevent rejection of the transplanted organ.

The most common side effects of azathioprine include nausea, vomiting, decreased appetite, liver function abnormalities, low white blood cell counts, and infection. It is usually taken by mouth once daily. Regular blood testing is recommended during treatment with azathioprine.

Typically, the invention relates to non-biological DMARDs, for example the invention may be defined as a method of assessing the efficacy of a non-biological DMARD. An advantage of the invention is that it may inform and improve clinical decision making, in particular, it may provide a more rapid determination that a non-biological DMARD is not effective and therefore permit an early and efficient change of treatment to a different non-biological DMARD or to a biological DMARD.
Specialized Pro-Resolving Mediators (SPMs)

SPM are molecules produced by enzymes primarily carried in leukocytes for the essential fatty acids arachidonic acids (AA), eicosapentaenoic acid (EPA), n-3 docosapentaenoic acid (n-3 DPA) and docosahexaenoic acids (DHA). These molecules are central in the regulation of innate and adaptive immune responses during inflammation to facilitate its termination. SPM may also be referred to as "lipid mediators".

Without being bound by theory, an increase in the levels of at least one SPM are thought to indicate efficacy because SPM are protective mediators.

As used herein, the terms "level" and "levels" are used interchangeably with the terms "concentration" and "concentrations".

The SPM may be a DHA metabolite, n-3 DPA metabolite, AA metabolite and/or an EPA metabolite. The method may comprise measuring the levels of at least one DHA metabolite, at least one n-3 DPA metabolite, at least one AA metabolite and/or at least one EPA metabolite.

The SPM may be a DHA metabolite and/or an EPA metabolite. The method may comprise measuring the levels of at least one DHA metabolite, and/or at least one EPA metabolite.

The invention may alternatively be characterised as comprising measuring the levels of at least one DHA metabolite, at least one n-3 DPA metabolite, at least one AA metabolite and/or at least one EPA metabolite, without reference to the term plasma specialized pro-resolving mediator (SPM). Likewise, the invention may be characterised as comprising measuring the levels of at least one DHA metabolite and/or at least one EPA metabolite, without reference to the term plasma specialized pro-resolving mediator (SPM). Similarly, the invention may be characterised by reference to any one or more of the specific EPA, n-3 DPA, AA and/or DHA metabolites defined below.
EPA Metabolites EPA metabolites include the "E-series resolvins" and EPA-derived monohydroxylated fatty acids.

EPA metabolites are listed in Table 1 below:

TABLE 1

| Abbreviation | Trivial name | Full stereochemistry |
|---|---|---|
| RvE1 | Resolvin E1 | 5S,12R,18R-trihydroxy-eicosa-6Z,8E,10E,14Z,16E-pentaenoic acid |
| RvE2 | Resolvin E2 | 5S,18R-dihydroxy-eicosa-6Z,8E,11E,14E,16Z-pentaenoic acid |
| RvE3 | Resolvin E3 | 17R,18R/S-dihydroxy-eicosa-5Z,8Z,11Z,13E,15E-pentaenoic acid |
| 18-HEPE | | 18-hydroxy-eicosa-5Z,8Z,11Z,14Z,16E-pentaenoic acid |
| 15-HEPE | | 15-hydroxy-eicosa-5Z,8Z,11Z,13E,17Z-pentaenoic acid |
| 12-HEPE | | 12-hydroxy-eicosa-5Z,8Z,10E,14Z,17Z-pentaenoic acid |
| 5-HEPE | | 5-hydroxy-eicosa-6E,8Z,11Z,14Z,17Z-pentaenoic acid | n-3 DPA Metabolites

These include the 13-series resolvins—RvT1, RvT2, RvT3 and RvT4, D-series resolvins-RvD1$_{n-3\ DPA}$, RvD2$_{n-3\ DPA}$ and RvD5$_{n-3\ DPA}$, Protectins PD1$_{n-3\ DPA}$ PD2$_{n-3\ DPA}$ and 10S, 17S-diHDPA and Maresins— MaR1$_{n-3\ DPA}$ MaR2$_{n-3\ DPA}$ and 7S, 14S-diHDPA together with the respective monohydroxylated fatty acids.

n-3 DPA metabolites are listed in Table 2 below:

TABLE 2

| Abbreviation | Trivial name | Full stereochemistry |
|---|---|---|
| Resolvin T1 | RvT1 | 7,13R,20-trihydroxy-docosa-8E,10Z,14E,16Z,18E-pentaenoic acid |
| Resolvin T2 | RvT2 | 7,12,13R-trihydroxy-docosa-8Z,10E,14E,16Z,19Z-pentaenoic acid |
| Resolvin T3 | RvT3 | 7,8,13R-trihydroxy-docosa-9E,11E,14E,16Z,19Z-pentaenoic acid |
| Resolvin T4 | RvT4 | 7,13R-dihydroxy-docosa-8,10Z,14E,16Z,19Z-pentaenoic acid |
| Resolvin D1$_{n-3\ DPA}$ | RvD1$_{n-3\ DPA}$ | 7S,8R,17S-trihydroxy-9E,11E,13Z,15E,19Z-docosapentaenoic acid |
| Resolvin D2$_{n-3\ DPA}$ | RvD2$_{n-3\ DPA}$ | 7S,16R,17S-trihydroxy-8E,10Z,12E,14E,19Z-docosapentaenoic acid |

TABLE 2-continued

| Abbreviation | Trivial name | Full stereochemistry |
|---|---|---|
| Resolvin D5$_{n-3\ DPA}$ | RvD5$_{n-3DPA}$ | 7S,17S-dihydroxy-8E,10Z,13Z,15E,19Z-docosapentaenoic acid |
| Protectin D1$_{n-3\ DPA}$ | PD1$_{n-3\ DPA}$ | 10R,17S-dihydroxy-7Z,11E,13E,15Z,19Z-docosapentaenoic acid |
| Protectin D2$_{n-3\ DPA}$ | PD2$_{n-3\ DPA}$ | 16R,17S-dihydroxy-7Z,10Z,12E,14E,19Z-docosapentaenoic acid |
| 10S,17S-diHDPA | 10S,17S-diHDPA | 10S,17S-dihydroxy-7Z,11E,13Z,15E,19Z-docosapentaenoic acid |
| Maresin 1$_{n-3\ DPA}$ | MaR1$_{n-3\ DPA}$ | 7R,14S-dihydroxy-8E,10E,12Z,16Z,19Z-docosapentaenoic acid |
| Maresin 2$_{n-3\ DPA}$ | MaR2$_{n-3\ DPA}$ | 13R,14S-dihydroxy-4Z,7Z,9E,11E,16Z,19Z-docosapentaenoic acid |
| 7S,14S-diHDPA | 7S,14S-diHDPA | 7S,14Sdihydroxy-8E,10Z,12E,16Z,19Zdocosapentaenoic acid |
| 17-HDHA | | 17-hydroxy-docosa-7Z,10Z,13Z,15E,19Z-pentaenoic acid |
| 14-HDHA | | 14S-hydroxy-docosa-7Z,10Z,12E,16Z,19Z-pentaenoic acid |
| 13-HDHA | | 13-hydroxy-docosa-7Z,10Z,14E,16Z,19Z-pentaenoic acid |
| 7-HDHA | | 7-hydroxy-docosa-8E,10Z,13Z,16Z,19Z-pentaenoic acid |

AA Metabolites

AA metabolites include Lipoxins—LXA$_4$, LXB$_4$, 5S, 15S-diHETE, 15R-LXA$_4$ and 15R-LXB$_4$ Leukotrienes: LTB$_4$, 5S, 12S-diHETE, 12-epi-LTB$_4$, 6-trans, 12-epi-LTB$_4$ and 20-OH-LTB$_4$, LTC$_4$, LTD$_4$ and LTE$_4$ and Prostanoids: PGD$_2$, PGE$_2$ and PGF$_{2\square}$ TxB$_2$ AA metabolites are listed in Table 3 below:

TABLE 3

| Abbreviation | Trivial name | Full stereochemistry |
|---|---|---|
| Lipoxin A$_4$ | LXA4 | 5S,6R,15S-trihydroxy-7E,9E,11Z,13E-eicosatetraenoic acid |
| Lipoxin B$_4$ | LXB4 | 5S,14R,15S-trihydroxy-6E,8Z,10E,12E-eicosatetraenoic acid |
| 15R-Lipoxin A$_4$ (15-epi-Lipoxin A$_4$) | 15R-LXA$_4$ (15-epi-LXA$_4$) | 5S,6R,15R-trihydroxy-7E,9E,11Z,13E-eicosatetraenoic acid |
| 15R-Lipoxin B$_4$ (15-epi-Lipoxin B$_4$) | 15R-LXB$_4$ (15-epi-LXB$_4$) | 5S,14R,15R-trihydroxy-6E,8Z,10E,12E-eicosatetraenoic acid |
| 13,14-dihydro, 15-oxo-Lipoxin A$_4$ | 13,14-dihydro, 15-oxo-LXA$_4$ | 5S,6R-dihydroxy-15-oxo-7E,9E,11Z-eicosatrienoic acid |
| 15-oxo-lipoxin A$_4$ | 15-oxo-LXA$_4$ | 5S,6R-dihydroxy-15-oxo-7E,9E,11Z,13E-eicosatetraenoic acid |
| 5S,15S-dihydroxy-eicosatetraenoic acid | 5S,15S-diHETE | 5S,15S-dihydroxy-6E,8Z,11Z,13E-eicosatetraenoic acid |
| Leukotriene B$_4$ | LTB$_4$ | 5S,12R-dihydroxy-6Z,8E,10E,14Z-eicosatetraenoic acid |
| 5S,12S-diHETE | 5S,12S-diHETE | 5S,12S-dihydroxy-6E,8Z,10E,14Z-eicosatetraenoic acid |
| Δ6-trans-leukotriene B$^4$ | Δ6-trans-LTB$_4$ | 5S,12R-dihydroxy-6E,8E,10E,14Z-eicosatetraenoic acid |
| Δ6-trans-12-epi-leukotriene B$_4$ | Δ-6-trans, 12-epi-LTB$_4$ | 5S,12S-dihydroxy-6E,8E,10E,14Z-eicosatetraenoic acid |
| 20-hydroxy-Leukotriene B$_4$ | 20-OH-LTB$_4$ | 5S,12R,20-trihydroxy-6Z,8E,10E,14Z-eicosatetraenoic acid |
| Leukotriene C$_4$ | LTC$_4$ | 5S-hydroxy-6R-(S-glutathionyl)-7E,9E,11Z,14Z-eicosatetraenoic acid |
| Leukotriene D$_4$ | LTD$_4$ | 5S-hydroxy-6R-(S-cysteinylglycinyl)-7E,9E,11Z,14Z-eicosatetraenoic acid |
| Leukotriene E$_4$ | LTE$_4$ | 5S-hydroxy-6R-(S-cysteinyl)-7E,9E,11Z,14Z-eicosatetraenoic acid |
| Prostaglandin D$_2$ | PGD$_2$ | 11-oxo-9α,15S-dihydroxy-5Z,13E-prostadienoic acid |
| Prostaglandin E$_2$ | PGE$_2$ | 9-oxo-11α,15S-dihydroxy-5Z,13E-prostadienoic acid |
| Prostaglandin F$_{2\alpha}$ | PGF$_{2\alpha}$ | 9α,11α,15S-trihydroxy-5Z,13E-prostadienoic acid |
| Thromboxane B$_2$ | TXB$_2$ | 9α,11,15S-trihydroxy-5Z,13E-thrombadienoic acid |
| 15-HETE | | 15-hydroxy-eicosa-5Z,8Z,11Z,13E-tetraenoic acid |
| 12-HETE | | 12-hydroxy-eicosa-5Z,8Z,10E,14-tetraenoic acid |
| 5-HETE | | 5-hydroxy-eicosa-6E,8Z,11Z,14Z,1-tetraenoicic acid |

DHA Metabolites

DHA metabolites include the "D-series resolvins—RvD1, RvD2, RvD3, RvD4, RvD5, RvD6, 17R-RvD1 and 17R-RvD3, Protectins—PD1, 10S,17S-diHDHA, 17R-PD1 and 22-OH-PD1, PCTR1, PCTR2 and PCTR3 and Maresins— MaR1, 7S, 14S-diHDHA, MaR2, 4S, 14S-diHDHA and 22-OH-MaR1, MCTR1, MCTR2 and MCTR3".

DHA metabolites are listed in Table 4 below:

TABLE 4

| Abbreviation | Trivial name | Full stereochemistry |
|---|---|---|
| RvD1 | Resolvin D1 | 7S,8R,17S-trihydroxy-docosa-4Z,9E,11E,13Z,15E,19Z-hexaenoic acid |
| RvD2 | Resolvin D2 | 7S,16R,17S-trihydroxy-docosa-4Z,8E,10Z,12E,14E,19Z-hexaenoic acid |
| RvD3 | Resolvin D3 | 4S,7R,17S-trihydroxy-docosa-5Z,7E,9E,13Z,15E,19Z-hexaenoic acid |
| RvD4 | Resolvin D4 | 4S,5R,17S-trihydroxy-docosa-6E,8E,10Z,13Z,15E,19Z-hexaenoic acid |

TABLE 4-continued

| Abbreviation | Trivial name | Full stereochemistry |
|---|---|---|
| RvD5 | Resolvin D5 | 7S,17S-dihydroxy-docosa-4Z,8E,10Z,13Z,15E,19Z-hexaenoic acid |
| RvD6 | Resolvin D6 | 4S,17S-dihydroxy-docosa-5E,7Z,10Z,13Z,15E,19Z-hexaenoic acid |
| MaR1 | Maresin 1 | 7R,14S-dihydroxy-docosa-4Z,8E,10E,12Z,16Z,19Z-hexaenoic acid |
| 4S,14S-diHDHA | | 4S,14S-dihydroxy-docosa-5Z,7E,10E,12Z,16E,19E-hexaenoic acid |
| 7S,14S-diHDHA | | 7S,14S-dihydroxy-docosa-4Z,8E,10E,12Z,16E,19E-hexaenoic acid |
| 14-oxo-MaR1 | | 14-oxo-7R,-hydroxy-docosa-4Z,8E,10E,12Z,16Z,19Z-hexaenoic acid |
| MCTR1 | Maresin Conjugate in Tissue Regeneration 1 | 13R-glutathionyl,14S-hydroxy-4Z,7Z,9E,11E,13R,14S,16Z,19Z-docosahexaenoic acid |
| MCTR2 | Maresin Conjugate in Tissue Regeneration 2 | 13R-cysteinylglycinyl,14S-hydroxy-4Z,7Z,9E,11E,13R,14S,16Z,19Z-docosahexaenoic acid |
| MCTR1 | Maresin Conjugate in Tissue Regeneration 3 | 13R-cysteinyl,14S-hydroxy-4Z,7Z,9E,11E,13R,14S,16Z,19Z-docosahexaenoic acid |
| PD1 | Protectin D1 | 10R,17S-dihydroxy-docosa-4Z,7Z,11E,13E,15Z,19Z-hexaenoic acid |
| 10S,17S-diHDHA | Protectin Dx | 10S,17S-dihydroxy-docosa-4Z,7Z,11E,13Z,15Z,19Z-hexaenoic acid |
| 17R-PD1 | 17R-Protectin D1 | 10R,17R-dihydroxy-docosa-4Z,7Z,11E,13E,15Z,19Z-hexaenoic acid |
| 22-OH-PD1 | 22-OH- Protectin D1 | 10R,17S,20-trihydroxy-docosa-4Z,7Z,11E,13E,15Z,19Z-hexaenoic acid |
| PCTR1 | Protectin Conjugate in Tissue Regeneration 1 | 16R-glutathionyl,17S-hydroxy-4Z,7Z,10Z,12E,14E,19Z-docosahexaenoic acid |
| PCTR2 | Protectin Conjugate in Tissue Regeneration 2 | 16R-cysteinylglycinyl,17S-hydroxy-4Z,7Z,10Z,12E,14E,19Z-docosahexaenoic acid |
| PCTR3 | Protectin Conjugate in Tissue Regeneration 3 | 16R-cysteinyl,17S-hydroxy-4Z,7Z,10Z,12E,14E,19Z-docosahexaenoic acid |
| 17-HDHA | | 17-hydroxy-docosa-4Z,7Z,10Z,13Z,15E,19Z-hexaenoic acid |
| 14-HDHA | | 14S-hydroxy-docosa-4Z,7Z,10Z,12E,16Z,19Z-hexaenoic acid |
| 13-HDHA | | 13-hydroxy-docosa-4Z,7Z,10Z,14E,16Z,19Z-hexaenoic acid |
| 7-HDHA | | 7-hydroxy-docosa-4Z,8E,10Z,13Z,16Z,19Z-hexaenoic acid |
| 4-HDHA | | 4-hydroxy-docosa-5E,7Z,10Z,13Z,16Z,19Z-hexaenoic acid |

Measuring SPM

The method may comprise measuring a D-series resolvin and/or an E-series resolvin. The D-series resolvin may be selected from the group consisting of RvD1, RvD2, RvD3, RvD4, RvD5, RvD6, 17R-RvD1 and 17R-RvD3. Any combination of the D-series resolvins may be measured. The E-series resolving may be selected from the group consisting of RvE1, RvE2 and RvE3. Any combination of the E-series resolvins may be measured.

The method may comprise measuring the levels of RvT3; RvT4; RvD1; MaR1$_{n-3}$ $_{DP4}$; RvT4; RvE2; 14-oxo-MaR1; 17R-RvD3; 15R-LXB4; RvD3; RvD4; TxB2; LTB4; 20-COOH-LTB4; LTE4; 10S, 17S,diHDHA (PDX); 17R-PD1; 15R-LXA4; PGE2; PGD2; MaR1$_{n-3}$ $_{DP4}$; 10S, 17S-diHDPA; 4S, 14S-diHDHA; 5S, 12S-diHETE; and/or 5S, 15S-diHETE.

The method may comprise measuring the levels of RvD4, 10S,17S-diHDPA, 15R-LXA$_4$ and/or MaR1$_{n-3}$ $_{DP4}$. The method may comprise measuring the levels of RvD4, 5S,12S-diHETE, 4S, 14S-diHDHA, 10S,17S-diHDPA, 15R-LXA$_4$ and/or MaR1$_{n-3}$ $_{DP4}$. The method may comprise measuring the levels of RvD4, 10S,17S-diHDPA, 15R-LXA$_4$ and MaR1$_{n-3}$ $_{DP4}$. The method may comprise measuring the levels of RvD4, 5S,12S-diHETE, 4S, 14S-diHDHA, 10S,17S-diHDPA, 15R-LXA$_4$ and MaR1$_{n-3}$ $_{DP4}$.

The method may comprise measuring the levels of RvD4, 10S,17S-diHDPA, 15R-LXA$_4$ and/or 5S,12S-diHETE. The method may comprise measuring the levels of RvD4, 10S, 17S-diHDPA, 15R-LXA$_4$ and 5S,12S-diHETE.

The method may comprise measuring the levels of at least one SPM. The method may comprise measuring the levels of at least two, at least three or at least four SPM. Accordingly, the at least one SPM may be at least four SPM. The at least four SPM may comprise RvD4, 10S,17S-diHDPA, 15R-LXA$_4$ and MaR1$_{n-3}$ $_{DP4}$. The at least two or at least three SPM may comprise any two or three SPM selected from RvD4, 5S,12S-diHETE, 4S, 14S-diHDHA, 10S,17S-diHDPA, 15R-LXA$_4$ and MaR1$_{n-3}$ $_{DP4}$ The method may comprise measuring the levels of at least six SPM. Accordingly, the at least one SPM may be at least six SPM. The at least six SPM may comprise RvD4, 5S,12S-diHETE, 4S, 14S-diHDHA, 10S,17S-diHDPA, 15R-LXA$_4$ and MaR1$_{n-3}$ $_{DP4}$. The method may comprise measuring the levels of at least five SPM. The at least five SPM may comprise any five selected from RvD4, 5S,12S-diHETE, 4S, 14S-diHDHA, 10S,17S-diHDPA, 15R-LXA$_4$ and MaR1$_{n-3}$ $_{DP4}$.

The method may comprise measuring the levels of RvT3; RvT4; RvD1; MaR1$_{n-3}$ $_{DP4}$; RvT4; 14-oxo-MaR1; 17R-RvD3; 15-epi-LXB4; RvD3; RvD4; TxB2; LTB4; 20-COOH-LTB4; LTE4; 10S, 17S,diHDHA (PDX); 17R-PD1; 15-epiLXA4; PGE2; PGD2; 10S, 17S-diHDPA; and/or 5S, 15S-diHETE.

The method may comprise measuring the levels of RvT3; RvT4; RvD1; MaR1$_{n-3}$ $_{DP4}$; RvT4; RvE2; 14-oxo-MaR1; 17R-RvD3; 15-epi-LXB4; RvD3; RvD4; TxB2; LTB4; 20-COOH-LTB4; LTE4; 10S, 17S,diHDHA (PDX); 17R-PD1; 15-epiLXA4; PGE2; PGD2; 10S, 17S-diHDPA; and/or 5S, 15S-diHETE.

The method may comprise measuring the levels of 14-oxo-MaR1, RvD4, RvT3 and/or RvE2. The method may comprise measuring the levels of 14-oxo-MaR1 and RvD4. The method may comprise measuring the levels of 14-oxo-MaR1, RvD4, RvT3 and RvE2.

The method may comprise measuring the levels of at least one SPM. The method may comprise measuring the levels of at least four SPM. Accordingly, the at least one SPM may be at least four SPM. The at least four SPM may comprise 14-oxo-MaR1, RvD4, RvT3 and RvE2.

The method may comprise measuring the levels of at least one SPM, for example at least two, at least three, at least four, at least five or at least six SPM selected from the top 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 or 54 SPMs shown in FIG. 1 F.

The method may comprise measuring the levels of SPM that are involved in coordinating the host response during ongoing inflammation. The method may therefore include measuring levels of PCTR2, RvD2 and/or RvD3.

The method may comprise measuring the levels of SPM that are mediators linked with pain modulation. The method may therefore include measuring levels of RvE1 and/or RvE2.

The method may comprise measuring the levels of SPM that are mediators linked with pain modulation and SPM that are involved in coordinating the host response during ongoing inflammation. The method may therefore include measuring levels of PCTR2, RvD2, RvD3, RvE1 and/or RvE2. Any combination of these SPM mediators may be measured. Any two or any three or any four of these SPM mediators may be measured. All five of these SPM mediators may be measured.

DMARD Responders and Non-Responders

The method may further comprise classifying the patient as a DMARD responder or a DMARD non-responder based on the efficacy of the DMARD. Where an increase in the level of the at least one SPM after administration of the DMARD indicates that the DMARD is effective, the patient will be classified as a DMARD responder. Conversely, where no increase in the level of the at least one SPM after administration of the DMARD is detected, the patient will be classified as a DMARD responder.

As used herein, the term "DMARD responder" typically refers to a non-biological DMARD responder; that is a patient who is responding or will respond to treatment with a non-biological DMARD. Likewise, the term "DMARD non-responder" typically refers to a non-biological DMARD non-responder; that is a patient who is not responding or will not respond to treatment with a non-biological DMARD. Both DMARD responders and DMARD non-responders may respond to biological DMARDs.

A responder is clinically defined as a patient who after treatment have a low disease activity score-28 (DAS28)<3.2

The method may comprise measuring the levels of ALOX5 and/or ALOX15-derived mediators from both the n-3 DPA and DHA metabolomes. ALOX5 and ALOX15-derived mediators from both the n-3 DPA and DHA metabolomes include RvD1, RvD4, $RvD1_{n\text{-}3\ DPA}$ and $RvD2_{n\text{-}3\ DPA}$ ALOX5 and ALOX15-derived mediators from both the n-3 DPA and DHA metabolomes may be reduced in non-responders.

The method may comprise measuring the levels of ALOX5 derived products of EPA. ALOX5-derived mediators from the EPA metabolomes include RvE1 and RvE2. ALOX5—derived mediators from the EPA metabolome may be reduced in non-responders.

The method may comprise measuring the levels of ALOX5 derived products of AA. ALOX5 derived products of AA include the leukocyte chemoattractant $LTB_4$ and the ionotropic cysteinyl leukotrienes. AA-derived ALOX5 products may be increased in plasma from non-responders when compared with responders.

Samples

Each sample may be defined as a "patient sample" or a "biological sample".

Samples are typically obtained prior to the methods of the invention being performed. The methods of the invention are in vitro methods accordingly. In some alternative embodiments, the method may further comprise a step or steps of sample collection.

The sample may be a plasma or whole blood sample. Preferably, the sample is a plasma sample. When the sample is a plasma sample, the SPM may be described as a plasma specialized pro-resolving mediator (SPM).

The sample obtained before treatment with a DMARD may have been obtained at any within 24 h prior to commencement of treatment.

The sample obtained after treatment with a DMARD may have been obtained around six months after commencement of treatment with the DMARD. However, changes may even be observed as soon as 1 month after treatment. The sample after treatment with a DMARD may have been obtained around 1 month, around 2 months, around 3 months, around 4 months or around 5 months after commencement of treatment with the DMARD.

The samples may be treated immediately after collection with an anticoagulant such, for example, as heparin to prevent clotting.

If the samples—for example human plasma samples—are required to be stored prior to analysis, they may be placed in an organic solvent and stored at a temperature of −75° C. or below, e.g., −80° C. Suitably, the organic solvent may comprise or consist of methanol. Although lipid mediators have been found to be unstable in frozen samples during the term-long-term storage, with the levels of some of the mediators being significantly (>50%) reduced following three-month storage, it has been surprisingly found that by using methanol, and optionally other organic solvents, the stability of these molecules may be improved when they are stored for an extended period at temperatures of −75° C. and below. Suitably, the samples may be stored at temperatures of about −80° C. or less. The samples may be stored for at least about 1 month, and in some embodiments at least about 3 months, up to about 9 months or longer.

Deuterium labelled standards of the kind described below may be added to the samples prior to freezing.

Measuring SPM Levels

Methods for measuring the levels of SPM in biological samples such as blood and tissue are available to those skilled in the art and need not be described herein in detail. Suitable methods are disclosed, for example, in Yang R, Chiang N, Oh SF and Serhan C N. 2011. "Metabolomics-Lipidomics of Eicosanoids and Docosanoids Generated by Phagocytes". Curr Protoc Immunol. 95:14.26:14.26.1-14.26.26 and Dalli J and Serhan C N. 2012. "Specific lipid mediator signatures of human phagocytes: microparticles stimulate macrophage efferocytosis and pro-resolving mediators". Blood. 2012; 120:e60-e72, the contents of both of which are incorporated herein by reference.

Briefly, in some embodiments, the levels of the at least one SPM in the samples may be measured using liquid chromatography tandem mass spectrometry (LC-MS/MS) after extracting the SPMs from the samples.

The SPMs may be extracted from the samples using solid-phase extraction, for instance using C18 columns. Suitable methods are disclosed by Colas R A, Shinohara M, Dalli J, Chiang N and Serhan C N. "Identification and signature profiles for pro-resolving and inflammatory lipid mediators in human tissue". Am J Physiol Cell Physiol. 2014; 307:C39-54, the contents of which are incorporated herein by reference.

One or more internal labelled standards may be added to the samples prior to extraction of the SPMs to facilitate quantitation of the SPM in the samples. Suitable labelled standards are deuterium-labelled 5S-HETE (5S-HETE-da), deuterium-labelled leukotriene $B_4$ ($LTB_4$-$d_4$), deuterium-labelled lipoxin $A_4$ ($LXA_4$-$d_5$), deuterium-labelled resolvin D2 (RvD2-$d_5$) and deuterium-labelled prostaglandin $E_2$ ($PGE_2$-$d_4$).

The identity of a SPM in a sample may be confirmed by matching its retention time (RT) and at least 6 diagnostic ions from its MS-MS spectrum with those of a synthetic or authentic standard for the SPM. Retention times for molecules measured using liquid chromatography are often instrument specific, but in some embodiments for example, the retention times of the above-mentioned 13-series resolvins may be as shown in Table 5 below:

TABLE 5

| 13-series resolvin (RvT) | Retention time (R$_T$) |
| --- | --- |
| RvT1 | 10.8 min ± 0.3 min |
| RvT2 | 11.2 min ± 0.3 min |
| RvT3 | 11.5 min ± 0.3 min |
| RvT4 | 13.6 min ± 0.3 min |

Quantitation may be achieved using linear regression curves that are constructed using a synthetic or authentic standard for the mediator.

LC-MS/MS may be suitable for use in situations where there is access to the equipment required such, for example, in hospital laboratories. However, more conveniently, the levels of the at least one SPM in the samples may be measured using an immunoassay. Immunoassays have the potential to be miniaturised to run on a microfluidics device or test-strip and may be more suited for clinical point-of-care applications. Embodiments of the invention which incorporate an immunoassay may therefore be used in situ by a primary healthcare provider for assistance in prescribing a statin for an individual patient.

The levels of the at least one SPM may be measured using a homogeneous or heterogeneous immunoassay.

Thus, in some embodiments, the levels of the or each SPM may be measured in solution by binding to labelled antibodies that are present in excess, whereby binding alters detectable properties of the label. The amount of a specific SPM present will therefore affect the amount of the label with a particular detectable property. As is well known in the art, the label may comprise a radioactive label, a fluorescent label or an enzyme having a chromogenic or chemiluminescent substrate that is coloured or caused or allowed to fluoresce when acted on by the enzyme.

The antibodies may be polyclonal or monoclonal with specificity for the SPM. In some embodiments, monoclonal antibodies may be used.

Alternatively, a heterogeneous format may be used in which the at least one SPM is captured by surface-bound antibodies for separation and quantification. In some embodiments, a sandwich assay may be used in which a surface-bound SPM is quantified by binding a labelled secondary antibody.

Suitably, the immunoassay may comprise an enzyme immunoassay (EIA) in which the label is an enzyme such, for example, as horseradish peroxidase (HRP). Suitable substrates for HRP are well known in the art and include, for example, ABTS, OPD, AmplexRed, DAB, AEC, TMB, homovanillic acid and luminol. In some embodiments, an ELISA immunoassay may be used; a sandwich ELISA assay may be particularly preferred.

The immunoassay may be competitive or non-competitive. Thus, in some embodiments, the amounts of the at least one SPM may be measured directly by a homogeneous or heterogeneous method, as described above. Alternatively, the SPM in the samples may be sequestered in solution with a known amount of antibody which is present in excess, and the amount of antibody remaining then determined by binding to surface-bound SPM to give an indirect read-out of the amount of SPM in the original sample. In another variant, the at least one SPM may be caused to compete for binding to a surface bound antibody with a known amount of a labelled SPM.

The surface bound antibodies or SPM may be immobilised on any suitable surface of the kind known in the art. For instance, the antibodies or SPM may be immobilised on a surface of a well or plate or on the surface of a plurality of magnetic or non-magnetic beads.

In some embodiments, the immunoassay may be a competitive assay, further comprising a known amount of the SPM, which is the same as the one to be quantitated in the sample, but tagged with a detectable label. The labelled SPM may be affinity-bound to a suitable surface by an antibody to the SPM. Upon adding the sample a proportion of the labelled SPM may be displaced from the surface-bound antibodies, thereby providing a measure of the level of SPM in the sample.

In some embodiments, the immunoassay may comprise surface-bound SPM, which is the same as the SPM that is to be quantitated in the sample, and a known amount of antibodies to the SPM in solution in excess. The sample is first mixed with the antibodies in solution such that a proportion of the antibodies bind with the SPM in the sample. The amount of unbound antibodies remaining can then be measured by binding to the surface-bound SPM.

In some embodiments, the immunoassay may comprise a labelled secondary antibody to the SPM or to a primary antibody to the SPM for quantifying the amount of the SPM bound to surface-bound antibodies or the amount of primary antibody bound to the SPM immobilised on a surface.

Measuring SPM levels may be by equipment for measuring the level of a specific SPM in a sample comprising a sample collection device and an immunoassay. The equipment may further comprise a detector for detecting labelled SPM or labelled antibodies to the SPM in the immunoassay. Suitable labels are mentioned above, but in a preferred embodiment, the label may be an enzyme having a chromogenic or chemiluminescent substrate that is coloured or caused or allowed to fluoresce when acted on by the enzyme.

The immunoassay or equipment may be incorporated into a miniaturised device for measuring the level of at least one SPM in a biological sample. Suitably, the device may comprise a lab-on-a-chip.

Measuring SPM levels may be by a device for measuring the level of at least one SPM in a sample obtained from a patient, the device comprising one or more parts defining an internal channel having an inlet port and a reaction zone, in which a SPM in a sample may be reacted with an immobilised primary antibody for the SPM for capturing the SPM, or a primary antibody for the SPM in excess in solution after mixing with the sample upstream of the reaction zone may be reacted with SPM, which is the same as the one to be measured in the sample, but immobilised on a surface within the reaction zone, for quantifying directly or indirectly the amount of the SPM in the sample.

The captured SPM or primary antibody may then be detected using a secondary antibody to the SPM or primary antibody, which is tagged with an enzyme.

As described above, the enzyme may have a chromogenic or chemiluminescent substrate that is coloured or caused or allowed to fluoresce when acted on by the enzyme. Suitably, the one or more parts of the device defining the channel, at least adjacent the reaction zone, may be transparent to light, at least in a range of wavelengths encompassing the colour or fluorescence of the substrate to allow detection of a reaction between the SPM or primary antibody and the secondary antibody using a suitable detector such, for example, as a photodiode, positioned outside the channel or further channel.

In some embodiments, the device may comprise a plurality of channels, each with its own inlet port, for measuring the levels of a plurality of different SPMs in the sample in parallel. Therefore, each channel may include a different respective immobilised primary antibody or SPM. Suitably, the device may comprise one or more selectively operable valves associated with the one or more inlet ports for controlling the admission of a sequence of different reagents into to the channels such, for example, as the sample, wash solutions, primary antibody, secondary antibody and enzyme substrate.

The device therefore may comprise a microfluidics device. The channel may include a reaction zone. Microfluidics devices are known to those skilled in the art. A review of microfluidic immunoassays or protein diagnostic chip microarrays is provided by Chin et al. 2012. *Lab on a Chip.* 2012; 12:2118-2134. A microfluidics device suitable for carrying out an ELISA immunoassay at a point-of-care is disclosed by Chan C D, Laksanasopin T, Cheung Y K, Steinmiller D et al. "Microfluidics-based diagnostics of infectious diseases in the developing world". *Nature Medicine.* 2011; 17(8):1015-1019, the contents of which are incorporated herein by reference.

Assessing Efficacy

Assessing the efficacy of a DMARD may comprise comparing levels of the at least one SPM in the samples obtained from the patient before and after administration of the DMARD. Where the comparison indicates that the level of the at least one SPM is higher in the sample obtained from the patient after administration of the DMARD than in the sample obtained from the patient before administration of the DMARD then the comparison shows there is an increase in the level of the at least one SPM after administration of the DMARD is indicative of efficacy of the DMARD. It will be appreciated that the converse comparison is equivalent; a decrease in the level of the at least one SPM before administration of the DMARD is indicative of efficacy of the DMARD. Likewise, a decrease in the level of the at least one SPM after administration of the DMARD is indicative of DMARD ineffectiveness. DMARD ineffectiveness may be observed in a patient resistant to DMARD therapy.

An increase is a difference compared to pre-treatment values. The increase may for example be an increase of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 100%. The increase may be an increase of at least about 20%.

Alternatively, an increase may be expressed as a fold change. The skilled person will appreciate that any percentage increase may be converted to a fold change and vice versa.

The terms "indicates" and "indicative" are used because, without being bound by theory, a method may determine that a DMARD is ineffective under particular circumstances, but this is not an absolute determination, for instance a different treatment regimen or an increased dose may yet be effective in some cases. However, the terms may "indicates" and "indicative" be replaced with "determine" and "determines" as appropriate, for instance when a maximum recommended dose of a DMARD is used, the method can determine that the DMARD is ineffective. Any of the above terms may be replaced with the terms "predict" or "predictive". Where discreet groups are involved, the word "classify" and its variants may be used, such as "wherein an increase in the level of the at least one SPM after administration of the DMARD classifies the DMARD as effective".

Where multiple SPM are measured, the increase that indicates efficacy of the DMARD may be the same or may be different for each SPM.

Assessing the efficacy of a DMARD may comprise a comparison with a control, such as a control database. A control database may be particularly beneficial when the levels of multiple SPM are be assessed.

The method may therefore comprise a further step of comparing the levels of the at least on SPM in samples obtained from the patient before administration of the DMARD with the levels of the at least on SPM in samples obtained from the patient after administration of the DMARD. Such a comparison may be performed by any method known in the art, including by a statistical method.

The method may comprise a further step of finding a difference between the levels of the at least on SPM in samples obtained from the patient before administration of the DMARD and the levels of the at least on SPM in samples obtained from the patient after administration of the DMARD. This step may be performed by any method known in the art, including by a statistical method. The method may therefore comprise a further step of determining whether the DMARD is effective or ineffective based on the levels of the at least on SPM in samples obtained from the patient before administration of the DMARD and the levels of the at least on SPM in samples obtained from the patient after administration of the DMARD. For instance, the method may comprise determining whether the DMARD is effective or ineffective based on a comparison of and/or finding a difference between the levels of the at least on SPM in samples obtained from the patient before administration of the DMARD and the levels of the at least on SPM in samples obtained from the patient after administration of the DMARD.

The method may comprise a further step of determining the DMARD is ineffective and optionally changing the patient's treatment.

The method may comprise assessing the efficacy of a DMARD using a multivariate analysis. The multivariate analysis may be orthogonal partial least squares-discrimination analysis (oPLS-DA).

oPLS-DA generates a regression model based on concentrations of lipid mediators differently expressed between two groups (Chong, J., Yamamoto, M. & Xia, J. MetaboAnalystR 2.0: "From Raw Spectra to Biological Insights." Metabolites 9 (2019). oPLS-DA may be performed using the MetaboAnalyst web-based application (https://www.metaboanalyst.ca/faces/ModuleView.xhtml).

The method may comprise assessing the efficacy of a DMARD using a trained machine learning model. Such a machine learning model may be used to predict the response to DMARD treatment based on data such as one or more of: SPM profiles (including individual concentrations for each SPM for each patient), clinical scores and specific SPM families. The data may be separated based on the specific pathotype of the patient.

The machine learning model may be created using various scripts, such as R scripts, to create Support Vector Machine (SVM) models and/or random forest prediction models, for example. The machine learning model may therefore comprise at least one of an SVM model and a random forest prediction model. The skilled person is familiar with SVM models and random forest prediction models, and as such a specific implementation of SVM models and random forest prediction models will now be briefly described.

The SVM models may be created using the known and freely-accessible package ClassyFire developed by the Wishart Research Group (http://classyfire.wishartlab.com/), and described in the publication: *Djoumbou Feunang Y, Eisner R, Knox C, Chepelev L, Hastings J, Owen G, Fahy E, Steinbeck C, Subramanian S, Bolton E, Greiner R, and Wishart DS. ClassyFire: Automated Chemical Classification With A Comprehensive, Computable Taxonomy. Journal of Cheminformatics*, 2016, 8:61. As the skilled person would understand, ClassyFire is a web-based application for automated structural classification of chemical entities. ClassyFire uses an SVM to create the machine learning models. As would be understood, SVM classifies, makes a regression, and creates a novelty detection for the creation of the model. Several such models may be created until the most accurate model is found. Validation of the models is achieved using a validation cohort to estimate the Matthews Correlation Coefficient (MCC) value and assess the accuracy of the prediction, as would be understood. These SVM models output accuracy percentages and MCC values after validation.

The SVM models are trained based on training data. Such data includes "explanatory" data and "response" data for patients in which the treatment outcome is already knows. The explanatory data comprises all the data that is used to determine why a patent is or isn't a responder. For example, the explanatory data may be lipid mediator profiles for a particular patient, including the individual concentrations of lipid mediators as obtained from plasma. The response data comprises data indicating whether or not the particular patient actually is or isn't a responder. The training data may therefore comprise a tab-delimited table with a training dataset of patients as columns and lipid mediators as rows, and a tab-delimited table with a validation dataset of patients as columns and lipid mediators as rows.

The random forest models may be created using the known package randomForest as described in the publication: *A. Liaw and M. Wiener* (2002). *Classification and Regression by randomForest. R News* 2(3), 18-22. As the skilled person would understand, this package creates a random forest model based on classification and regression of random forests. The random forest models may be created using random forests and bootstrapping in order to decorrelate the multiple trees generated on different bootstrapped samples from the training data, and then reduce the variance in the trees by averaging. The use of averaging improves the performance of decision trees and avoids overfitting. The randomForest package creates several trees, each one using different variables to create a best version.

The mtry parameter, which is the number of variables available for splitting at each tree node, can be used to define how many variables the data is split into to create different trees. Specifically in this use, the importance of each lipid mediator in the improvement of the model's accuracy is estimated by defining the lipid mediators to create a loop, monitoring for a change in accuracy of the model, and defining the best mtry based on the lipid mediator's effect on the accuracy of the model. The model may then be re-run based on the defined best mtry value. As for the SVM models, a validation cohort is used to estimate the MCC value. These random forest models output accuracy percentages and MCC values after validation, and may also output one or more plots associated with the performance of the model and the importance of each lipid mediator in the construction of the model.

The random forest models, like the SVM models, are trained using training data. The training data used to train the random forest models may be the same as that used to train the SVM models.

The method may therefore comprise measuring the levels of at least two SPM and determining whether the DMARD is effective, the method comprising inputting the levels of at least two SPM into a trained machine learning algorithm, the trained machine learning algorithm being arranged to:

i. Compare the levels of the at least two SPM from the sample obtained from the patient before administration of the DMARD with the levels of the same at least two SPM in the sample obtained from the patient after administration of the DMARD, and ii. Output whether the DMARD is effective or ineffective; optionally wherein the trained machine learning model is a Support Vector Machine (SVM) model and/or a random forests model.

The trained machine learning algorithm may be trained based on training data, the training data comprising:

First data including lipid mediator profiles for a plurality of patients before and after administration of the DMARD, optionally including concentrations of lipid mediators; and Second data identifying whether for each of the plurality of patients the DMARD was effective or ineffective.

Treatment of Inflammatory Conditions Including Rheumatoid Arthritis

DMARDS (including biologicals) are the main types of treatment for rheumatoid arthritis. Patients are also prescribed NSAIDs, Usually patients are given NSAIDs at early stages to manage symptoms and usually prior to diagnosis. Upon diagnosis patients are usually prescribed Methotrexate (~80-90%) if within the first weeks there is no improvement, this may be combined with another non-biological DMARD such as hydrochloroquinone and if after 6 months there is no improvement other drugs, usually biologicals, are administered.

The prescription of biological DMARDs is restricted under current guidelines until after non-biological treatment has been attempted. One reason for this is that non-biological DMARDs are much cheaper than biologicals.

Patient treatment may be modified on the basis of the present invention. The method of the invention may allow:

Terminating treatment with an ineffective DMARD and starting treatment with an alternative DMARD instead.

Terminating treatment with an ineffective DMARD and starting treatment with a biologic instead.

Changing the dose of an ineffective DMARD.

Combining the ineffective DMARD with a different DMARD.

The advantageous outcome is that a patient will not need to wait 6 months to determine whether they are getting an effective drug or not, and so the clinician can explore different combinations or doses of the drug, or switch to a different drug.

The method may therefore further comprise modifying treatment of the patient. For example, the method may further comprise a subsequent step of selected from the group consisting of:

a) terminating treatment with an ineffective DMARD and starting treatment with an alternative DMARD, b) terminating treatment with an ineffective DMARD and starting treatment with a biological DMARD instead, c) changing the dose of an ineffective DMARD, typically increasing the dose of an ineffective DMARD, and/or d) combining the ineffective DMARD with a different DMARD.

The method may comprise selecting a treatment for the patient wherein:

(a) if the DMARD is effective then the same DMARD is selected, and (b) if the DMARD is ineffective then a different DMARD, optionally a biological DMARD, is selected;

and optionally further comprising administering the selected treatment to the patient.

According to a second aspect, the invention provides a method for predicting which rheumatoid arthritis pathotype a patient having, suspected of having, or at risk of developing rheumatoid arthritis will develop comprising measuring the level of at least one specialized pro-resolving mediator (SPM) in a disease-modifying antirheumatic drug (DMARD) naïve patient sample and classifying the rheumatoid arthritis pathotype a patient will develop as Lympho-myeloid, Diffuse-myeloid and Pauci-immune-fibroid.

The term "DMARD naïve" refers to a patient who has never taken a DMARD, or has never been prescribed a DMARD. The patient may have never taken and/or been prescribed a DMARD for treatment of rheumatoid arthritis.

Patients with RA can be classified into three categories or pathotypes: Lympho-myeloid, Diffuse-myeloid and Pauci-immune-fibroid. These classifications are typically performed based on based on synovial molecular and histological features. Each category of RA is associated with distinct disease evolution and responses to DMARD treatment.

In one embodiment, an upregulation of pro-resolving mediators identifies that the patient has the Pauci-immune-fibroid pathotype. An upregulation of 15R-LXA4 and/or MCTR2 may identify that the patient has the Pauci-immune-fibroid pathotype.

In one embodiment, an upregulation of pro-inflammatory and immunosuppressive mediators identifies that the patient has the Pauci-immune-fibroid pathotype. An upregulation of PGD2, TxA2 and/or TxB2, may identify that the patient has the Pauci-immune-fibroid pathotype. Levels of TxA2 may be measured indirectly via its stable further metabolite TxB2.

The term "classifying" is used interchangeably with the terms, "diagnosing" and "predicting". The method may be considered a method for diagnosing which rheumatoid arthritis pathotype a patient having, suspected of having, or at risk of developing rheumatoid arthritis will develop, accordingly.

Classifying may comprise comparing levels of the at least one SPM in the sample obtained from the patient with a control. Where the comparison indicates that the level of the at least one SPM is higher in the sample obtained from the patient than the control then the comparison shows there is an increase in the level of the at least one SPM in the patient sample.

An increase is a difference compared to control values. The increase may for example be an increase of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 100%. The increase may be an increase of at least about 20%.

Alternatively, an increase may be expressed as a fold change. The skilled person will appreciate that any percentage increase may be converted to a fold change and vice versa.

Where multiple SPM are measured, the increase that indicates efficacy of the DMARD may be the same or may be different for each SPM.

Classifying the rheumatoid arthritis pathotype a patient will develop may comprise a comparison with a control, such as a control database. A control database may be particularly beneficial when the levels of multiple SPM are be assessed.

The method may comprise classifying the rheumatoid arthritis pathotype a patient will develop using a multivariate analysis. The multivariate analysis may be orthogonal partial least squares-discrimination analysis (oPLS-DA).

The method may comprise classifying the rheumatoid arthritis pathotype a patient will develop using a trained machine learning model. The trained machine learning model may be an SVM model and/or a random forests model.

The method may comprise measuring the levels of at least two SPM and predicting which rheumatoid arthritis pathotype a patient will develop, the method comprising inputting the levels of at least two SPM into a trained machine learning algorithm, the trained machine learning algorithm being arranged to:

i. Compare the levels of the at least two SPM from the sample with the levels of the same at least two SPM in a database, and iii. Output whether the patient will develop the Lympho-myeloid, Diffuse-myeloid or Pauci-immune-fibroid pathotype;

optionally wherein the trained machine learning model is a Support Vector Machine (SVM) model and/or a random forests model.

The trained machine learning algorithm may be trained based on training data, the training data comprising:

First data including lipid mediator profiles for a plurality of patients, optionally including concentrations of lipid mediators; and Second data identifying whether each of the plurality of patients developed the Lympho-myeloid, Diffuse-myeloid or Pauci-immune-fibroid pathotype.

In one embodiment, the method comprises comparing the level of the at least one SPM in the patient sample to one or more controls. An "increase" or "upregulation" may be determined by comparison with the one or more controls.

The one or more controls may be one or more control samples. The one or more control samples may be analysed in parallel to the patient sample. The level of the one or more SPM may be compared to the level of the corresponding one or more SPM in the control sample. An "increase" or "upregulation" may be determined by comparison with the control sample. Comparison may be to an average SPM level between a plurality of control samples.

The one or more controls may be a database comprising levels previously obtained from one or more control samples. The level of the one or more SPM may be compared to the level of the corresponding one or more SPM in the database. An "increase" or "upregulation" may be determined by comparison with the database.

The control may be an average level of the one or more SPM in rheumatoid arthritis patient samples.

Where a clinician may treat one pathotype differently from another pathotype, classifying the rheumatoid arthritis pathotype a patient will develop may allow the adoption of a particular, or an alternative, treatment regime more suited to the patient.

For instance, without being bound by theory, the evidence so far suggests that patients with the Pauci-immune-fibroid pathotype are more resistant to DMARDs. These patients may therefore benefit more from their treatment being biologicals rather that non-biological DMARDs such as Methotrexate for example.

The method may further comprise selecting a treatment for the patient. The treatment for the patient may be selected on the basis of the classification of the rheumatoid arthritis pathotype the patient will develop.

The method may further comprise administering the treatment selected for the patient.

In one embodiment, wherein the method classifies the rheumatoid arthritis pathotype as the Pauci-immune-fibroid pathotype, a treatment with a biological DMARD is selected and optionally administered to the patient.

According to a third aspect, the invention provides a method for predicting whether a patient having, suspected of having, or at risk of developing an inflammatory condition will respond to treatment with a disease-modifying antirheumatic drug (DMARD) comprising measuring the level of at least one specialized pro-resolving mediator (SPM) in a DMARD naïve patient sample and classifying the patient as a predicted DMARD responder or a predicted DMARD non-responder.

An advantage of this aspect is instead of waiting for the disease to progress a patient would give a sample in which the levels SPMs may be measured in order to determine if they are likely to respond or not. If not, they could be immediately prescribed alternative treatments such as biologicals.

The method may comprise measuring RvD4, 10S,17S-diHDPA, 15R-LXA$_4$ and/or MaR1$_{n-3\ DPA}$. The method may comprise measuring RvD4, 10S,17S-diHDPA, 15R-LXA$_4$ and MaR1$_{n-3\ DPA}$. The method may comprise measuring RvD4, 5S,12S-diHETE, 4S, 14S-diHDHA, 10S,17S-diHDPA, 15R-LXA4 and/or MaR1n-3 DPA. The method may comprise measuring RvD4, 5S,12S-diHETE, 4S, 14S-diHDHA, 10S,17S-diHDPA, 15R-LXA4 and MaR1n-3 DPA.

The method may comprise measuring 14-oxo-MaR1, RvD4, RvT3 and/or RvE2. The method may comprise measuring 14-oxo-MaR1 and RvD4. The method may comprise measuring 14-oxo-MaR1, RvD4, RvT3 and RvE2.

The method may comprise measuring RvD5 and/or RvT3.

The method may further comprise measuring the level of at least one pro-inflammatory eicosanoid. The pro-inflammatory eicosanoid(s) may be PGD$_2$ and/or PGE$_2$. PGD$_2$ and/or PGE$_2$ are AA-derived mediators but are not SPM. An increase in the level of at least one pro-inflammatory eicosanoid may predict that the patient is a DMARD non-responder.

The method may further comprise measuring a marker of ALOX5 activity; a marker of ALOX12 activity and/or a marker of ALOX15 activity. The marker of ALOX5 activity; a marker of ALOX12 activity and/or a marker of ALOX15 activity may be an S-isomer of a monohyrdoxylated fatty acid. The method may comprise chiral analysis of the marker of ALOX5 activity; a marker of ALOX12 activity and/or a marker of ALOX15 activity.

The marker of ALOX5 activity may be selected from the group consisting of 5-HETE, 5HEPE, 7-HDPA and 7-HDHA. Any combination of ALOX5 markers may be measured. Any two or any three ALOX5 marker may be measured. All four ALOX5 markers may be measured. The method may therefore comprise measuring 5-HETE, 5HEPE, 7-HDPA and/or 7-HDHA. Preferably, the method comprises measuring 7-HDHA, 5-HEPE and 5-HETE.

The marker of ALOX12 activity may be selected from the group consisting of 14-HDPA and 14-HDHA. Any combination of ALOX12 markers may be measured. The method may therefore comprise measuring 14-HDPA and/or 14-HDHA.

The marker of ALOX15 activity may be selected from the group consisting of 17-HDPA, 17-HDHA, 15-HEPE and 15-HETE. Any combination of ALOX15 markers may be measured. Any two or any three ALOX15 marker may be measured. All four ALOX5 markers may be measured. The method may therefore comprise measuring 17-HDPA, 17-HDHA, 15-HEPE and/or 15-HETE.

In an alternative aspect, the invention provides a method for predicting whether a patient with rheumatoid arthritis will respond to treatment with a DMARD comprising measuring a marker of ALOX5 activity; a marker of ALOX12 activity and/or a marker of ALOX15 activity in a DMARD naïve patient sample and classifying the patient as a predicted DMARD responder or a predicted DMARD non-responder.

The term "classifying" is used interchangeably with the terms, "diagnosing" and "predicting". The method may be considered a method for diagnosing whether a patient having, suspected of having, or at risk of developing an inflammatory condition will respond to treatment with a DMARD, accordingly.

The method may comprise classifying a patient as a predicted DMARD non-responder when the level of the at least one SPM is increased.

Classifying may comprise comparing levels of the at least one SPM in the sample obtained from the patient with a control. Where the comparison indicates that the level of the at least one SPM is higher in the sample obtained from the patient than the control then the comparison shows there is an increase in the level of the at least one SPM in the patient sample.

An increase is a difference compared to control values. The increase may be for example be an increase of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95% or at least about 100%. The increase may be an increase of at least about 20%.

Alternatively, an increase may be expressed as a fold change. The skilled person will appreciate that any percentage increase may be converted to a fold change and vice versa.

Where multiple SPM are measured, the increase that indicates efficacy of the DMARD may be the same or may be different for each SPM.

Classifying the patient as a predicted DMARD non-responder or as a predicted DMARD responder may comprise a comparison with a control, such as a control database. A control database may be particularly beneficial when the levels of multiple SPM are be assessed.

The method may comprise classifying a patient as a predicted DMARD non-responder using a multivariate analysis. The multivariate analysis may be orthogonal partial least squares-discrimination analysis (oPLS-DA).

The method may comprise a patient as a predicted DMARD non-responder using a trained machine learning model. The trained machine learning model may be an SVM model and/or a random forests model.

The method may comprise measuring the levels of at least two SPM and determining whether the patient is a DMARD responder or a DMARD non-responder, the method comprising inputting the levels of at least two SPM into a trained machine learning algorithm, the trained machine learning algorithm being arranged to:

i. Compare the levels of the at least two SPM from the sample with the levels of the same at least two SPM in a database, and ii. Output whether the patient is a DMARD responder or a DMARD non-responder;

optionally wherein the trained machine learning model is a Support Vector Machine (SVM) model and/or a random forests model.

The trained machine learning algorithm may be trained based on training data, the training data comprising:

First data including lipid mediator profiles for a plurality of patients, optionally including concentrations of lipid mediators; and Second data identifying whether each of the plurality of patients is a DMARD responder or a DMARD non-responder.

In addition to the machine learning models, another script may be used to perform differential gene expression analysis of the ALOX12, ALOX5, ALOX15 and ALOX15B enzymes. This script may be created using the known and freely-accessible package edgeR as described in the publications: *Robinson M D, McCarthy D J, Smyth G K (2010). "edgeR: a Bioconductor package for differential expression analysis of digital gene expression data." Bioinformatics,* 26(1), 139-140 *and McCarthy D J, Chen Y, Smyth G K* (2012). *"Differential expression analysis of multifactor RNA-Seq experiments with respect to biological variation." Nucleic Acids Research,* 40(10), 4288-4297. This script uses the quasi-likelihood method to identify differences in the expression levels of specific genes between a DMARD responder and a DMARD non-responder. It also provides a violin plots to visualize the different gene expression levels.

In one embodiment, the method comprises comparing the level of the at least one SPM in the patient sample to one or more controls. An "increase" or "upregulation" may be determined by comparison with the one or more controls.

The one or more controls may be one or more control samples. The one or more control samples may be analysed in parallel to the patient sample. The level of the one or more SPM may be compared to the level of the corresponding one or more SPM in the control sample. An "increase" or "upregulation" may be determined by comparison with the control sample. Comparison may be to an average SPM level between a plurality of control samples.

The one or more controls may be a database comprising levels previously obtained from one or more control samples. The level of the one or more SPM may be compared to the level of the corresponding one or more SPM in the database. An "increase" or "upregulation" may be determined by comparison with the database.

The control may be an average level of the one or more SPM in a plurality of DMARD naïve patient samples.

If a patient is classified ahead of treatment as a predicted DMARD non-responder then a clinician may treat that patient differently to a patient classified as a predicted DMARD responder. Classifying the patient as a predicted DMARD non-responder or as a predicted DMARD responder may allow the adoption of a particular, or an alternative, treatment regime more suited to the patient.

For instance, a predicted DMARD non-responder may be more resistant to DMARDs. These patients may therefore benefit more from their treatment being biologicals rather that non-biological DMARDs such as Methotrexate for example.

The method may further comprise selecting a treatment for the patient. The treatment for the patient may be selected on the basis of the classification of the patient as a predicted DMARD non-responder or as a predicted DMARD responder.

The method may further comprise selecting a treatment for the patient wherein:

(a) if the patient is a predicted DMARD responder then a non-biological DMARD is selected, and (b) if the patient is a predicted DMARD non-responder then a biological DMARD is selected;

and optionally further comprising administering the selected treatment to the patient.

The method may further comprise administering the treatment selected for the patient.

In one embodiment, wherein the method classifies the patient as a predicted DMARD non-responder, a treatment with a biological DMARD is selected and optionally administered to the patient.

In another embodiment, wherein the method classifies the patient as a predicted DMARD responder, a treatment with a non-biological DMARD is selected and optionally administered to the patient.

In one embodiment, the method comprises comparing the level of the at least one SPM in the patient sample to one or more controls. An "increase" or "upregulation" may be determined by comparison with the one or more controls.

The one or more controls may be one or more control samples. The one or more control samples may be analysed in parallel to the patient sample. The level of the one or more SPM may be compared to the level of the corresponding one or more SPM in the control sample. An "increase" or "upregulation" may be determined by comparison with the control sample. Comparison may be to an average SPM level between a plurality of control samples.

The one or more controls may be a database comprising levels previously obtained from one or more control samples. The level of the one or more SPM may be compared to the level of the corresponding one or more SPM in the database. An "increase" or "upregulation" may be determined by comparison with the database.

The control may be an average level of the one or more SPM in samples from patients having, suspected of having, or at risk of developing the same inflammatory condition.

The method of the second aspect may be combined with the method of the third aspect. Without being bound by theory, integrating a predication of which rheumatoid arthritis pathotype a patient having, suspected of having, or at risk of developing rheumatoid arthritis will develop with a prediction of whether the patient is a DMARD responder or a DMARD non-responder may:

a) Provide an improved prediction of whether the patient is a DMARD responder or a DMARD non-responder, and/or b) provide an improved selection of a treatment for the patient.

Accordingly, the invention also provides a method for predicting whether a patient having, suspected of having, or at risk of developing rheumatoid arthritis will respond to treatment with a disease-modifying antirheumatic drug (DMARD) comprising classifying the rheumatoid arthritis pathotype a patient will develop as Lympho-myeloid, Diffuse-myeloid and Pauci-immune-fibroid in accordance with the method of the second aspect, measuring the level of at least one specialized pro-resolving mediator (SPM) in a DMARD naïve patient sample and classifying the patient as a predicted DMARD responder or a predicted DMARD non-responder.

The method of the third aspect may therefore further comprise classifying the rheumatoid arthritis pathotype a patient will develop as Lympho-myeloid, Diffuse-myeloid and Pauci-immune-fibroid in accordance with the method of the second aspect.

In some embodiments, where the patient is classified as a patient that will develop the Pauci-immune-fibroid pathotype and as a predicted DMARD non-responder, a treatment with a biological DMARD is selected and optionally administered to the patient.

Computer Implementation

The methods of the present invention may be performed by a computer and equipment controlled by the computer. The step of measuring the level of at least one specialized pro-resolving mediator (SPM) may be performed by equipment controlled by the computer.

The invention also provides a computer-implemented method of assessing the efficacy of a DMARD for use in the treatment of an inflammatory condition in a patient, which comprises receiving in a computer sample data representing the levels of at least one SPM in samples obtained from the patient before and after administration of the DMARD and executing software on the computer to compare the levels of the at least one SPM in the samples, an increase in the level of the at least one SPM after administration of the DMARD being indicative of efficacy of the DMARD, and to output efficacy data representing the efficacy of the DMARD on the basis of the comparison.

The invention also provides a computer program comprising instructions which, when executed by a computer, cause the computer to carry out a computer implemented method of the invention.

It will be appreciated that the step of comparing the levels of the at least one SPM in the samples may be carried out on a different computer from a computer that initially receives data representing the levels of the SPM in the samples.

The invention also provides a computer apparatus for assessing the efficacy of a DMARD for use in the treatment of an inflammatory condition in a patient, which comprises a first device incorporating a computer, a second computer and a communication channel between the first device and second computer for the transmission of data therebetween; wherein the first device is arranged to receive sample data representing the levels of at least one SPM in samples obtained from the patient before and after administration of the DMARD and to transmit the sample data to the second computer via the communication channel, and the second computer is arranged to execute software to compare the levels of the at least one SPM in the samples to determine the efficacy of the DMARD for the patient, an increase in the level of the at least one SPM after administration of the DMARD being indicative of efficacy, and output efficacy data representing the efficacy of the DMARD.

The second computer may be arranged to transmit the efficacy data to the first device via the communication channel, or to a third computer.

In some embodiments, the first device may incorporate an immunoassay, equipment or device for measuring the level of at least one SPM in a sample.

The invention also provides a computer implemented method and computer apparatus for predicting which rheumatoid arthritis pathotype a patient having, suspected of having, or at risk of developing rheumatoid arthritis will develop in accordance with the second aspect of the invention, the features of which correspond to those given above for a computer implemented method and computer apparatus in accordance with the first aspect of the invention mutatis mutandis.

The invention also provides a computer implemented method and computer apparatus for predicting whether a patient having, suspected of having, or at risk of developing an inflammatory condition will respond to treatment with a disease-modifying antirheumatic drug (DMARD) in accordance with the third aspect of the invention, the features of which correspond to those given above for a computer implemented method and computer apparatus in accordance with the first aspect of the invention mutatis mutandis.

Further Advantages

Using samples from deeply phenotyped patients diagnosed with rheumathoid arthritis that had not yet received treatment for their conditions the inventors assessed the levels of bioactive mediators in their plasma and assessed the correlation of these lipid mediators with outcome of treatment with DMARDs. Results from these studies demonstrated identified four specific molecules that were prognostic for treatment outcome. In addition, these studies also demonstrated that peripheral mediator concentrations may be related to disease subsets which in turn are linked with disease severity and treatment responsiveness.

Thus, these results indicate that comparing the levels of bioactive lipid mediators in plasma from patients upon diagnosis will provide an indication on which therapeutic they may respond best to. In addition, measuring the plasma levels of these molecules after initiation of treatment will also provide an indication of whether the patient is responding to the given treatment or not.

This methodology can predict whether a patient with Rheumatoid Arthritis will respond to treatment with DMARDs.

An advantage provided by the invention is the ability of a clinician to tell at the outset whether DMARD treatment will be effective. Currently, whilst it can become apparent quite quickly whether a specific treatment regime is working or not, it may well take a cycle of six months of dose escalation, combination with pain killers etc. before a clinician may try, first a different DMARD, and then ultimately a different class of drug. That second cycle can take another six months, totaling a year of disease progression and potentially irreversible damage, before an effective treatment (likely a biological) is used. This is debilitating to the patient and brings not only health consequences, in the form of secondary disease complications, for example cardiovascular disease, and MTX side-effects, but also economic consequences. To these can be added the side effects of DMARDs which can be quite unpleasant.

An advantage provided by the invention in relation to determination of the disease pathotype is that, as well as having a relationship to the potential responsiveness of the patient, different pathotypes require different levels of treatment aggression. Determination of a patient's disease pathotype therefore allows personalisation of their treatment.

The invention finds use in both clinical laboratories to aid in patient stratification as well as to in pharmaceuticals as an aid to drug development.

Preferred features for the second and subsequent aspects of the invention are as for the first aspect of the invention mutatis mutandis.

The present invention will now be described by way of reference to the following Examples and accompanying Drawings which are present for the purposes of illustration only and are not to be construed as being limiting on the invention.

Example 1—Plasma SPM Concentrations are Predictive of Responsiveness to DMARD Treatment in RA Patients In order to determine whether peripheral blood SPM concentrations are predictive of DMARD responsiveness in patients with RA, we investigated plasma lipid mediator profiles in deeply phenotyped early RA patients prior to treatment initiation (see table 6 for patient information). Plasma lipid mediators were identified in accordance with published criteria (Dalli, J., Colas, R. A., Walker, M. E. & Serhan, C. N. "*Lipid Mediator Metabolomics Via LC-MS/MS Profiling and Analysis*." Methods Mol Biol 1730, 59-72 (2018), the contents of which are incorporated by reference). In RA patient plasma we identified mediators from all four major essential fatty acid metabolomes, i.e. arachidonic acid (AA), EPA, n-3 DPA and DHA (Table 7). These included the EPA, n-3 DPA and DHA-derived resolvins and the n-3 DPA and DHA-derived protectins and maresins. We next used Orthogonal Projections to Latent Structures Discriminant Analysis (OPLS-DA), which generates a regression model based on concentrations of lipid mediators differently expressed between two groups (Chong, J., Yamamoto, M. & Xia, J. MetaboAnalystR 2.0: "*From Raw Spectra to Biological Insights.*" Metabolites 9 (2019), the contents of which are incorporated by reference), to assess the concentrations of identified mediators between DMARD-responders and DMARD-non-responders. Here we observed two distinct clusters representing DMARD-responders and DMARD-non-responders (FIG. 1A, B). We next used machine learning method random forests to build models based on plasma lipid mediator concentrations to further evaluate whether pre-treatment levels of these mediators were linked with DMARD responsiveness. Using this approach, we found that cumulative concentrations of the DHA (that includes the D-series resolvins, protectins and maresins) and EPA (that includes the E-series resolvins) metabolomes were the most accurate at predicting whether a patient would respond to treatment or not. The accuracy for the DHA metabolome at predicting outcome was of ~81% and that of the n-3 DPA metabolome was of ~69% (FIG. 1C and Table 8). Of note, these values were also higher than those obtained using a combination of clinical parameters that included the DAS28-ESR and rheumatoid factor concentrations (FIG. 1C).

In order to validate the robustness of our model we obtained peripheral blood lipid mediator profiles from a second cohort of DMARD naive patients composed of 36 responders and 22 non-responders, and tested whether the models generated using the different mediator metabolomes predicted outcome for patients in this cohort (see Tables 9 and 10 for patient clinical parameters and lipid mediator concentrations). For this purpose, we assessed the receiver operating characteristic (ROC) curve, which evaluates the diagnostic potential of a classifier by varying its discrimination threshold. Assessment of the area under the curve for the generated plots demonstrated that the DHA metabolome gave an AUC of 0.44, whereas the n-3 DPA metabolome gave an AUC of 0.58 (FIG. 1D, FIG. 13 and Table 8). Similar findings were made using support vector machines, a different machine learning strategy. Here, the DHA metabolome gave the highest accuracy score of ~62%, an AUC of 0.54, whilst the n-3 DPA metabolome gave an accuracy score of 61%, an AUC of 0.66 (Table 1). We further evaluated the ability of the n-3 DPA metabolome-based model to accurately categorize patients using the resulting confusion matrix of the model. Here we found that the model based on concentrations of n-3 DPA derived mediators was able to correctly classify ~83% of responders in the appropriate category (FIG. 1E). Thus, these results indicate that baseline peripheral blood lipid mediator profiles are linked with DMARD treatment outcome.

TABLE 6

| Cohort 1 patient demographics and clinical information | | |
| --- | --- | --- |
| | DMARD - Responders (n = 30) | DMARD- Non-Responders (n = 24) |
| Pathotype (n) | Lymphoid (10), Fibroid (10), Myeloid (10) | Lymphoid (9), Fibroid (8), Myeloid (7) |
| Ethnicity (n) | Caucasian (19), Black (2), Indian (1), Caribbean (1), Asian (3), Bangladeshi (2), Black African (1) | Asian (1), Bangladeshi (1), Black (7), British (1), Caribbean (3), Caucasian (9), Filipino (1) |
| Diagnosis | RA | RA |
| Gender (n) | Female (16), Male (14) | Female (21), Male(3) |
| Age at Recruitment - years | 51 (±21) | 56 (±9.5) |
| Onset | 5.6 (±3.4) | 6.0 (±3.42) |
| Currently smoking (%) | 5 (16.7) | 10 (43.5) |
| Co-Morbs Baseline (n) | Acne (1), Anaemia (1), Vitamin D deficiency (3), Hypercholesterolemia (2), Asthma (3), Hypertension (9), Osteoarthritis (2), Hypothyroidism (3), Gout (1), Shingles (1), Graves' disease (1), Kidney disease (1), TIA (1), Cardiovascular disease (1), Type 1 diabetes (1), Reactive iritis (1), Raised cholesterol (1), Hypothyroidism (3), Glaucoma (1), Thalassaemia (1), Poor vision (1), Heart surgery (1), Rubello in utero (1), Scleritis (1), COPD (1), E Enlarged prostate (1), Sinusitis (1), Peptic ulcer (1), Lower back pain (1), Acute MI (1), Ischaemic heart disease (1), Ca bladder (1) | Hypercholesterolemia (2), Asthma (5), Hypertension (12), Osteoarthritis (2), Hypothyroidism (1), COPD (1), Ischaemic heart disease (2), Osteoporosis (1), Sickle cell trait (1), IBS (2), Cervical spondylitis (1), Psoriasis (1), Fatty liver (1), Renal impairment (1), Coronary artery disease (1), Angina (1), Dyslipidaemia (1), Menorrhagia (1), Multiple sclerosis (1), Rectal incontinence (1), Detrusor instability (1), Meniscus tear/knee (1), Depression (1), Spina Bifida occulta (1), Axonal neuropathy (1), BCC (1), Gastritis (1), Heart valve repaired (1), Hysterectomy (1), foot & shoulder surgery (1), Endometriosis (1), Hay fever (1), Hysterectomy (1) |

TABLE 6-continued

| | Cohort 1 patient demographics and clinical information | |
|---|---|---|
| | DMARD - Responders (n = 30) | DMARD- Non-Responders (n = 24) |
| Concomitant Med. Baseline (n) | Tetracycline (1), Ferrous sulphate (1), Co-codamol (6), NSAIDs (3), Calcium vitamin D (2), Inhaler (1), Candesartan (1), Etoricoxib (1), Furosemide (1), Ramipril (2), Levothyroxine (1), Dihydrocodeine (1), Lisinopril (1), Lansoprazole (1), Bisoprolol (1), Tamsulosin (1), Carbimazole (1), Aspirin (2), Adcal (1), Simvastatin (5), Ibuprofen (4), Codeine (1), Losartan (1), Citalopram (1), Naproxen (5), Metformin (1), Lantus (1), Lacri-lube (1), Atenolol (1), Irbesartan (1), Amlodipine (2), Timolol (1), GTN spray (1), Frusemide (1), Celecoxib (1), Omeprazole (2), Budromide (1), Salbutamol (3), Diclofenac (1), Finasteride (1), Thyroxine (1), Talisartan (1) | Co-codamol (3), NSAIDs (3), Calcium vitamin D (3), Inhaler (1), Candesartan (2), Furosemide (1), Ramipril (3), Dihydrocodeine (1), Allopurinol (1), Lansoprazole (4), Aspirin (4), Simvastatin (5), Ibuprofen (2), Losartan (1), Ca-antagonist (1), Atenolol (2), Amlodipine (2), Alendronate (1), GTN spray (1), Pregabalin (2), Frusemide (1), Omeprazole (1), Salbutamol (1), Diclofenac (4), Thyroxine (2), Isosorbide (1), Adizem (1), Clopidogrel (2), Atorvastatin (1), Ivabradine (1), Co-tenidone (1), Nicorandil (1), Paracetamol (4), Tramadol (5), Amitriptyline (5), Piroxicam (1), Quinine (1), Bendroflumethiazide (3), Budesonide (2), Formoterol (1), Cetirizine (1), Arthrotec (1), Insulin (1), Doxazosin (2), Seretide (2), Spiriva (1), Arcoxia (1), Metformin (2), Glimepiride (1), Fluoxetine (1), Anti-hyper (1), Lyrica (1), CaD3 (1), Peppermint (1), Tiotropium (1), Detrusitol (1), Docusate (1), Voltron (1), HRT, (1), Aminophylline (1), Xolair (1), Ventolin (1), Oramorph (1), Temazepam (1) |
| Concomitant Med. 6 mth (n) | Ferrous sulphate (1), MTX (28), Folic acid (8), ASA (21), Co-codamol (6), HCQ (8), Prednisolone (6), NSAIDs (3), Calcium vitamin D (3), Azathioprine (1), Salbutamol (3), Inhaler (1), Candesartan (1), Etoricoxib (1), Furosemide (1), Ramipril (2), Levothyroxine (1), Dihydrocodeine (1), Lisinopril (1), Allopurinol (1), Lansoprazole (1), Bisoprolol (1), Tamsulosin (1), Carbimazole (1), Aspirin (2), Adcal (1), Simvastatin (5), Ibuprofen (4), Codeine (1), Losartan (1), Citalopram (1), Naproxen (5), Metformin (1), Lantus (1), Lacri-lube (1), Atenolol (1), Irbesartan (1), Amlodipine (3), Timolol (1), Frusemide (1), Celecoxib (1), Omeprazole (2), Budromide (1), Diclofenac (1), Thyroxine (1), GTN spray (1), Finasteride (1) | MTX (18), Folic acid (6), ASA (9), Co-codamol (2), HCQ (11), Prednisolone (5), NSAIDs (3), Calcium vitamin D (3), Salbutamol (1), Inhaler (1), Candesartan (1), Furosemide (1), Ramipril (3), Dihydrocodeine (1), Allopurinol (1), Lansoprazole (5), Aspirin (4), Simvastatin (5), Ibuprofen (2), Losartan (1), Atenolol (2), Amlodipine (2), Frusemide (1), Omeprazole (1), Diclofenac (4), Thyroxine (2), Atorvastatin (1), GTN spray (1), Ca-antagonist (1), Alendronate (1), Pregabalin (2), Co-tenidone (1), Leflunomide (2), Paracetamol (5), Tramadol (5), Amitriptyline (4), Piroxicam (1), Quinine (1), Spironolactone (1), Bendroflumethiazide (2), Clopidogrel (2), Sulfasalazine (2), Budesonide (2), Formoterol (1), Cetirizine (1), Insulin (1), Doxazosin (2), Isosorbide (1), Adizem (1), Ivabradine (1), Nicorandil (1), Seretide (2), Spiriva (1), Arcoxia (1), Metformin (2), Glimepiride (1), Fluoxetine (1), Anti-hyper (1), Lyrica (1), Peppermint (1), Tiotropium (1), CaD4 (1), Detrusitol (1), Docusate (1), Voltarol (1), Aminophylline (1), Xolair (1), Ventolin (1), Co-Amoxiclav (1), Calcichew (1) |
| DMARD Treatment (n) | MTX/ASA/HCQ (2), MTX/ASA (21), MTX/HCQ (3), ASA/HCQ (1), MTX (1) | MTX/ASA/HCQ (2), MTX/ASA (11), MTX/HCQ (6), MTX (1), ASA (1), HCQ (2) |
| Recent Steroid Therapy Baseline (n) | No (25), Yes (5) | No (19), Yes (3) |
| Steroid Treatment Baseline (n) | Depo-Medro (5) | Pred. (3) |
| Recent Steroid Therapy 6 mth (n) | No (13), Yes (15) | No (8), Yes (13) |
| Steroid Treatment 6 mth (n) | Pred (15) | Depo-Medro (1), Pred (11) |
| ESR Baseline | 28 (±23) | 41 (±28) |
| CRP Baseline | 14 (±17) | 24 (±37) |
| CCP Baseline | 210 (±201) | 249 (±255) |
| RF Baseline | 87 (±120) | 93 (±150) |
| ESR 6 mth | 7 (±7) | 30 (±14) |
| CRP 6 mth | 7 (±5) | 15 (±18) |
| Tiredness VAS Baseline | 34 (±29) | 48 (±26) |
| Pain VAS Baseline | 50 (±29) | 62 (±23) |
| Pt. VAS Global Health baseline | 67 (±24) | 72 (±19) |
| Physician VAS Global Assess. Baseline | 58 (±)21 | 65 (±20) |

TABLE 6-continued

Cohort 1 patient demographics and clinical information

| | DMARD - Responders (n = 30) | DMARD- Non-Responders (n = 24) |
|---|---|---|
| Tiredness VAS 6 mth | 28 (±27) | 64 (±17) |
| Pain VAS 6 mth | 12 (±14) | 66 (±22) |
| Pt. VAS Global Health 6 mth | 17 (±20) | 71 (±24) |
| Physician VAS Global Assess. 6 mth | 10 (±12) | 63 (±22) |
| Tender Joints Baseline | 12 (±7) | 13 (±9) |
| Swollen Joints Baseline | 7 (±5) | 8 (±5) |
| Tender Joints 6 mth | 1 (±1) | 17 (±8) |
| Swollen Joints 6 mth | 1 (±1) | 8 (±4) |
| HAQ Baseline | 1.41 (±0.68) | 1.83 (±0.60) |
| HAQ 6 mth | 0.57 (±0.73) | 1.79 (±0.51) |
| DAS28 Baseline | 5.58 (±0.98) | 5.81 (±1.08) |
| DAS28 6 mth | 1.86 (±0.65) | 6.17 (±0.98) |
| Delta DAS28 | −3.72 (±1.13) | 0.36 (±0.98) |
| US Synovial Thickness (12max) Baseline | 18 (±7) | 15 (±9) |
| US Power Doppler (12max) Baseline | 7 (±6) | 6 (±8) |
| US Synovial Thickness (Biopsied Joint) Baseline | 2 (±0.5) | 3 (±1) |
| US Power Doppler (Biopsied Joint) Baseline | 1 (±1) | 2 (±1) |
| US Synovial Thickness (12max) 6 mths | 6 (±4) | 7 (±8) |
| US Power Doppler (12max) 6 mths | 2 (±3) | 3 (±5) |
| Radiographic Erosion (n) | No (23), Yes (4) | No (20), Yes (2) |

Erythrocyte sedimentation rate = ESR, C-reactive protein = CRP, Anti-cyclic citrullinated peptide = CCP, rheumatoid factor = RF, VAS = visual analogue scale, HAQ = Health Assessment Questionnaire, DAS28 = disease activity score-28, US = ultrasound, MTX = methotrexate, ASA = aspirin, HCQ = hydroxychloroquine, LEF = Leflunomide.

TABLE 7

Baseline peripheral blood lipid mediator profiles in RA patient cohort 1

| | Q1 | Q3 | DMARD Responders Mean ± SEM | DMARD Non-Responders Mean ± SEM |
|---|---|---|---|---|
| DHA bioactive metabolome | | | | |
| RvD1 | 375 | 233 | 0.92 ± 0.44 | 2.20 ± 0.61 |
| RvD2 | 375 | 141 | 1.75 ± 0.73 | 1.52 ± 1.52 |
| RvD3 | 375 | 147 | 0.52 ± 0.15 | 1.06 ± 0.24 |
| RvD4 | 375 | 101 | 1.40 ± 0.53 | 5.70 ± 1.19 |
| RvD5 | 359 | 199 | 7.90 ± 1.06 | 8.17 ± 1.34 |
| RvD6 | 359 | 101 | 1.82 ± 0.66 | 1.30 ± 0.40 |

TABLE 7-continued

Baseline peripheral blood lipid mediator profiles in RA patient cohort 1

| | Q1 | Q3 | DMARD Responders Mean ± SEM | DMARD Non-Responders Mean ± SEM |
|---|---|---|---|---|
| 17R-RvD1 | 375 | 233 | 2.43 ± 1.62 | 3.69 ± 1.92 |
| 17R-RvD3 | 375 | 147 | 0.13 ± 0.05 | 0.60 ± 0.20 |
| PD1 | 359 | 153 | 0.78 ± 0.27 | 0.99 ± 0.33 |
| PDX | 359 | 153 | 0.63 ± 0.21 | 1.39 ± 0.46 |
| 17R-PD1 | 359 | 153 | 0.31 ± 0.13 | 0.74 ± 0.40 |
| 22-OH-PD1 | 375 | 153 | 2.36 ± 2.36 | 1.91 ± 1.46 |
| PCTR1 | 650 | 231 | 0.13 ± 0.13 | 0.00 ± 0.00 |
| PCTR2 | 521 | 231 | 1.48 ± 0.65 | 2.10 ± 1.80 |
| PCTR3 | 464 | 231 | 16.87 ± 6.74 | 4.75 ± 4.63 |

TABLE 7-continued

Baseline peripheral blood lipid mediator profiles in RA patient cohort 1

| | Q1 | Q3 | DMARD Responders Mean ± SEM | DMARD Non-Responders Mean ± SEM |
|---|---|---|---|---|
| MaR1 | 359 | 221 | 0.00 ± 0.00 | 0.00 ± 0.00 |
| MaR2 | 359 | 191 | 0.47 ± 0.20 | 0.56 ± 0.31 |
| 7S,14S-diHDHA | 359 | 221 | 3.21 ± 1.57 | 3.65 ± 1.73 |
| 4S,14S-diHDHA | 359 | 101 | 0.98 ± 0.48 | 4.29 ± 1.13 |
| 22-OH-MaR1 | 375 | 221 | 4.64 ± 3.77 | 5.31 ± 3.98 |
| 14-oxo-MaR1 | 357 | 248 | 0.73 ± 0.38 | 2.65 ± 0.78 |
| MCTR1 | 650 | 191 | 0.16 ± 0.16 | 0.38 ± 0.21 |
| MCTR2 | 521 | 191 | 1.42 ± 0.46 | 1.44 ± 1.04 |
| MCTR3 | 464 | 191 | 8.45 ± 2.67 | 6.57 ± 2.92 |
| n-3 DPA bioactive metabolome | | | | |
| RvT1 | 377 | 193 | 0.92 ± 0.69 | 0.66 ± 0.31 |
| RvT2 | 377 | 197 | 2.97 ± 1.31 | 2.26 ± 0.71 |
| RvT3 | 377 | 197 | 0.49 ± 0.17 | 0.60 ± 0.19 |
| RvT4 | 361 | 211 | 0.48 ± 0.13 | 0.78 ± 0.18 |
| $RvD1_{n\text{-}3\ DPA}$ | 377 | 143 | 4.73 ± 0.78 | 4.50 ± 0.58 |
| $RvD2_{n\text{-}3\ DPA}$ | 377 | 261 | 3.64 ± 1.22 | 2.32 ± 0.96 |
| $RvD5_{n\text{-}3DPA}$ | 361 | 199 | 3.39 ± 1.32 | 3.06 ± 1.26 |
| $PD1_{n\text{-}3\ DPA}$ | 361 | 155 | 0.72 ± 0.18 | 1.26 ± 0.38 |
| 10S,17S-diHDPA | 361 | 155 | 0.69 ± 0.33 | 2.11 ± 0.49 |
| $MaR1_{n\text{-}3\ DPA}$ | 361 | 249 | 0.07 ± 0.07 | 1.25 ± 0.49 |
| EPA bioactive metabolome | | | | |
| RvE1 | 349 | 161 | 1.98 ± 0.56 | 1.94 ± 0.83 |
| RvE2 | 333 | 199 | 0.30 ± 0.25 | 0.71 ± 0.34 |
| RvE3 | 333 | 201 | 2.89 ± 0.78 | 3.96 ± 0.95 |
| AA bioactive metabolome | | | | |
| $LXA_4$ | 351 | 115 | 0.72 ± 0.28 | 0.96 ± 0.60 |
| LXB4 | 351 | 221 | 5.14 ± 3.99 | 3.05 ± 1.47 |
| $15R\text{-}LXA_4$ | 351 | 115 | 0.97 ± 0.26 | 5.71 ± 2.27 |
| $15R\text{-}LXB_4$ | 351 | 221 | 3.90 ± 1.09 | 9.13 ± 2.60 |
| 5S,15S-diHETE | 335 | 115 | 36.90 ± 7.28 | 46.68 ± 7.59 |
| $LTB_4$ | 335 | 195 | 65.59 ± 13.57 | 115.09 ± 37.71 |
| 5S,12S-diHETE | 335 | 195 | 11.42 ± 9.03 | 12.69 ± 4.52 |
| $6\text{-trans-}LTB_4$ | 335 | 195 | 2.93 ± 0.57 | 5.37 ± 1.82 |
| $12\text{-epi-}6\text{-trans-}LTB_4$ | 335 | 195 | 3.56 ± 0.73 | 7.89 ± 2.10 |
| $20\text{-OH-}LTB_4$ | 351 | 195 | 61.80 ± 20.51 | 147.89 ± 50.54 |
| $20\text{-COOH-}LTB_4$ | 369 | 195 | 12.86 ± 5.40 | 22.68 ± 7.65 |
| $LTC_4$ | 626 | 189 | 12.34 ± 3.16 | 18.59 ± 8.10 |
| $LTD_4$ | 497 | 189 | 7.42 ± 2.20 | 6.93 ± 2.71 |
| $LTE_4$ | 440 | 189 | 32.99 ± 7.84 | 72.85 ± 16.13 |
| $PGD_2$ | 351 | 189 | 9.00 ± 2.47 | 15.22 ± 7.22 |
| $PGE_2$ | 351 | 189 | 13.39 ± 5.30 | 18.75 ± 5.76 |
| $PGF_{2a}$ | 353 | 193 | 29.26 ± 15.96 | 27.65 ± 7.49 |
| $TXB_2$ | 369 | 169 | 33.46 ± 13.46 | 83.09 ± 25.63 |

TABLE 8

Summary of prediction models created using the support vector machine and random forest methodologies.

| Machine Learning methodology | Samples | Model | Number of variables | % Accuracy Score | Model validation Sensitivity | Specificity | TP | FP | TN | FN |
|---|---|---|---|---|---|---|---|---|---|---|
| randomForest (RF) | All samples (1st cohort) | Four metabolomes | 54 | 73 | 0.87 | 0.55 | 87 | 45 | 55 | 13 |
| randomForest (RF) | All samples (1st cohort) | DHA metabolome | 23 | 81 | 0.9 | 0.68 | 90 | 32 | 68 | 10 |
| randomForest (RF) | All samples (1st cohort) | n-3 DPA metabolome | 10 | 69 | 0.83 | 0.5 | 83 | 50 | 50 | 17 |
| randomForest (RF) | All samples (1st cohort) | ERA metabolome | 3 | 65 | 0.8 | 0.45 | 80 | 55 | 45 | 20 |
| randomForest (RF) | All samples (1st cohort) | AA metabolome | 18 | 65 | 0.77 | 0.5 | 77 | 50 | 50 | 23 |
| randomForest (RF) | All samples (1st cohort) | Clin. Score | 11 | 50 | 0.6 | 0.36 | 60 | 64 | 36 | 40 |
| randomForest (RF) | All samples (2nd cohort) | RvD4, 10S, 17S-diHDPA, $15R\text{-}LXA_4$, $MaR1_{n\text{-}3\ DPA}$ | 4 | 83 | 0.92 | 0.68 | 92 | 32 | 68 | 8 |
| randomForest (RF) | All samples (2nd cohort) | RvD4, 10S, 17S-diHDPA, $15R\text{-}LXA_4$, 5S,12S-diHETE, 4S,14S-diHDHA, $MaR1_{n\text{-}3\ DPA}$ | 6 | 86 | 0.94 | 0.73 | 94 | 27 | 73 | 6 |
| randomForest (RF) | Fibroid samples (1st & 2nd cohort) | RvD4, 10S, 17S-diHDPA, $15R\text{-}LXA_4$, $MaR1_{n\text{-}3\ DPA}$ | 4 | 88 | 0.89 | 0.87 | 89 | 13 | 87 | 11 |
| randomForest (RF) | Lymphoid samples (1st & 2nd cohort) | RvD4, 10S, 17S-diHDPA, $15R\text{-}LXA_4$, $MaR1_{n\text{-}3\ DPA}$ | 4 | 83 | 0.89 | 0.7 | 89 | 30 | 70 | 11 |

TABLE 8-continued

Summary of prediction models created using the support
vector machine and random forest methodologies.

| randomForest (RF) | Myeloid samples (1st & 2nd cohort) | RvD4, 10S, 17S-diHDPA, 15R-LXA$_4$, MaR1$_{n\text{-}3\,DPA}$ | 4 | 70 | 0.86 | 0.47 | 86 | 53 | 47 | 14 |
|---|---|---|---|---|---|---|---|---|---|---|
| Classyfire (SVM) | All samples (1st cohort) | Four metabolomes | 54 | 61 | 0.63 | 0.54 | 63 | 46 | 54 | 37 |
| Classyfire (SVM) | All samples (1st cohort) | DHA metabolome | 23 | 62 | 0.65 | 0.56 | 65 | 44 | 56 | 35 |
| Classyfire (SVM) | All samples (1st cohort) | n-3 DPA metabolome | 10 | 61 | 0.63 | 0.54 | 63 | 46 | 54 | 37 |
| Classyfire (SVM) | All samples (1st cohort) | EPA metabolome | 3 | 60 | 0.62 | 0.52 | 62 | 48 | 52 | 38 |
| Classyfire (SVM) | All samples (1st cohort) | AA metabolome | 18 | 58 | 0.6 | 0.48 | 60 | 52 | 48 | 40 |
| randomForest (RF) | All samples (1st cohort) | Four metabolomes | 54 | 73 | 0.87 | 0.55 | 87 | 45 | 55 | 13 |
| randomForest (RF) | All samples (1st cohort) | DHA metabolome | 23 | 81 | 0.9 | 0.68 | 90 | 32 | 68 | 10 |
| randomForest (RF) | All samples (1st cohort) | n-3 DPA metabolome | 10 | 69 | 0.83 | 0.5 | 83 | 50 | 50 | 17 |
| randomForest (RF) | All samples (1st cohort) | EPA metabolome | 3 | 65 | 0.8 | 0.45 | 80 | 55 | 45 | 20 |
| randomForest (RF) | All samples (1st cohort) | AA metabolome | 18 | 65 | 0.77 | 0.5 | 77 | 50 | 50 | 23 |
| randomForest (RF) | All samples (1st cohort) | Clin. Score | 11 | 50 | 0.6 | 0.36 | 60 | 64 | 36 | 40 |
| randomForest (RF) | All samples (2nd cohort) | RvD4, PDX, 15R-LXA$_4$, MaR1$_{n\text{-}3\,DPA}$ | 4 | 83 | 0.92 | 0.68 | 92 | 32 | 68 | 8 |
| randomForest (RF) | All samples (2nd cohort) | RvD4, PDX, 15R-LXA$_4$, 5S,12S-diHETE, 4S,14S-diHDHA, MaR1$_{n\text{-}3\,DPA}$ | 6 | 86 | 0.94 | 0.73 | 94 | 27 | 73 | 6 |
| randomForest (RF) | Fibroid samples (1st & 2nd cohort) | RvD4, PDX, 15R-LXA$_4$, MaR1$_{n\text{-}3\,DPA}$ | 4 | 88 | 0.89 | 0.87 | 89 | 13 | 87 | 11 |
| randomForest (RF) | Lymphoid samples (1st & 2nd cohort) | RvD4, PDX, 15R-LXA$_4$, MaR1$_{n\text{-}3\,DPA}$ | 4 | 83 | 0.89 | 0.7 | 89 | 30 | 70 | 11 |
| randomForest (RF) | Myeloid samples (1st & 2nd cohort) | RvD4, PDX, 15R-LXA$_4$, MaR1$_{n\text{-}3\,DPA}$ | 4 | 70 | 0.86 | 0.47 | 86 | 53 | 47 | 14 |
| Classyfire (SVM) | All samples (1st cohort) | Four metabolomes | 54 | 61 | 0.63 | 0.54 | 63 | 46 | 54 | 37 |
| Classyfire (SVM) | All samples (1st cohort) | DHA metabolome | 23 | 62 | 0.65 | 0.56 | 65 | 44 | 56 | 35 |
| Classyfire (SVM) | All samples (1st cohort) | n-3 DPA metabolome | 10 | 61 | 0.63 | 0.54 | 63 | 46 | 54 | 37 |
| Classyfire (SVM) | All samples (1st cohort) | EPA metabolome | 3 | 60 | 0.62 | 0.52 | 62 | 48 | 52 | 38 |
| Classyfire (SVM) | All samples (1st cohort) | AA metabolome | 18 | 58 | 0.6 | 0.48 | 60 | 52 | 48 | 40 |

| Machine Learning methodology | Samples | Model | Model evaluation | | | | | | |
|---|---|---|---|---|---|---|---|---|---|
| | | | Sensitivity | Specificity | TP | FP | TN | FN | AUC |
| randomForest (RF) | All samples (1st cohort) | Four metabolomes | 0.58 | 0.64 | 58 | 36 | 64 | 42 | 0.72 |
| randomForest (RF) | All samples (1st cohort) | DHA metabolome | 0.39 | 0.55 | 39 | 45 | 55 | 61 | 0.44 |
| randomForest (RF) | All samples (1st cohort) | n-3 DPA metabolome | 0.78 | 0.32 | 78 | 68 | 32 | 22 | 0.58 |
| randomForest (RF) | All samples (1st cohort) | ERA metabolome | 0.53 | 0.32 | 53 | 68 | 32 | 47 | 0.6 |
| randomForest (RF) | All samples (1st cohort) | AA metabolome | 0.83 | 0.77 | 83 | 23 | 77 | 17 | 0.89 |
| randomForest (RF) | All samples (1st cohort) | Clin. Score | 0.03 | 0.88 | 3 | 12 | 88 | 97 | 0.53 |

TABLE 8-continued

Summary of prediction models created using the support
vector machine and random forest methodologies.

| randomForest (RF) | All samples (2nd cohort) | RvD4, 10S, 17S-diHDPA, 15R-LXA$_4$, MaR1$_{n-3\ DPA}$ | 0.83 | 0.59 | 83 | 41 | 59 | 17 | 0.8 |
|---|---|---|---|---|---|---|---|---|---|
| randomForest (RF) | All samples (2nd cohort) | RvD4, 10S, 17S-diHDPA, 15R-LXA$_4$, 5S,12S-diHETE, 4S,14S-diHDHA, MaR1$_{n-3\ DPA}$ | 0.87 | 0.64 | 87 | 36 | 64 | 13 | 0.79 |
| randomForest (RF) | Fibroid samples (1st & 2nd cohort) | RvD4, 10S, 17S-diHDPA, 15R-LXA$_4$, MaR1$_{n-3\ DPA}$ | N/A | N/A | N/A | N/A | N/A | N/A | N/A |
| randomForest (RF) | Lymphoid samples (1st & 2nd cohort) | RvD4, 10S, 17S-diHDPA, 15R-LXA$_4$, MaR1$_{n-3\ DPA}$ | N/A | N/A | N/A | N/A | N/A | N/A | N/A |
| rando est (RF) | Myeloid samples (1st & 2nd cohort) | RvD4, 10S, 17S-diHDPA, 15R-LXA$_4$, MaR1$_{n-3\ DPA}$ | N/A | N/A | N/A | N/A | N/A | N/A | N/A |
| Clas (SVM) | All samples (1st cohort) | Four metabolomes | 0.94 | 0.05 | 94 | 95 | 5 | 6 | 0.53 |
| Classyfire (SVM) | All samples (1st cohort) | DHA metabolome | 0.78 | 0.18 | 78 | 82 | 18 | 22 | 0.54 |
| Classyfire (SVM) | All samples (1st cohort) | n-3 DPA metabolome | 0.94 | 0.23 | 94 | 77 | 23 | 6 | 0.66 |
| Classyfire (SVM) | All samples (1st cohort) | EPA metabolome | 0.92 | 0.05 | 92 | 95 | 5 | 8 | 0.58 |
| Classyfire (SVM) | All samples (1st cohort) | AA metabolome | 0.92 | 0.09 | 92 | 91 | 9 | 8 | 0.66 |
| randomForest (RF) | All samples (1st cohort) | Four metabolomes | 0.58 | 0.64 | 58 | 36 | 64 | 42 | 0.72 |
| randomForest (RF) | All samples (1st cohort) | DHA metabolome | 0.39 | 0.55 | 39 | 45 | 55 | 61 | 0.44 |
| randomForest (RF) | All samples (1st cohort) | n-3 DPA metabolome | 0.78 | 0.32 | 78 | 68 | 32 | 22 | 0.58 |
| randomForest (RF) | All samples (1st cohort) | EPA metabolome | 0.53 | 0.32 | 53 | 68 | 32 | 47 | 0.6 |
| randomForest (RF) | All samples (1st cohort) | AA metabolome | 0.83 | 0.77 | 83 | 23 | 77 | 17 | 0.89 |
| randomForest (RF) | All samples (1st cohort) | Clin. Score | 0.03 | 0.88 | 3 | 12 | 88 | 97 | 0.53 |
| randomForest (RF) | All samples (2nd cohort) | RvD4, PDX, 15R-LXA$_4$, MaR1$_{n-3\ DPA}$ | 0.83 | 0.59 | 83 | 41 | 59 | 17 | 0.8 |
| randomForest (RF) | All samples (2nd cohort) | RvD4, PDX, 15R-LXA$_4$, 5S,12S-diHETE, 4S,14S-diHDHA, MaR1$_{n-3\ DPA}$ | 0.87 | 0.64 | 87 | 36 | 64 | 13 | 0.79 |
| rando est (RF) | Fibroid samples (1st & 2nd cohort) | RvD4, PDX, 15R-LXA$_4$, MaR1$_{n-3\ DPA}$ | N/A | N/A | N/A | N/A | N/A | N/A | N/A |
| rando est (RF) | Lymphoid samples (1st & 2nd cohort) | RvD4, PDX, 15R-LXA$_4$, MaR1$_{n-3\ DPA}$ | N/A | N/A | N/A | N/A | N/A | N/A | N/A |
| randomForest (RF) | Myeloid samples (1st & 2nd cohort) | RvD4, PDX, 15R-LXA$_4$, MaR1$_{n-3\ DPA}$ | N/A | N/A | N/A | N/A | N/A | N/A | N/A |
| Classyfire (SVM) | All samples (1st cohort) | Four metabolomes | 0.94 | 0.05 | 94 | 95 | 5 | 6 | 0.53 |
| Classyfire (SVM) | All samples (1st cohort) | DHA metabolome | 0.78 | 0.18 | 78 | 82 | 18 | 22 | 0.54 |
| Classyfire (SVM) | All samples (1st cohort) | n-3 DPA metabolome | 0.94 | 0.23 | 94 | 77 | 23 | 6 | 0.66 |
| Classyfire (SVM) | All samples (1st cohort) | EPA metabolome | 0.92 | 0.05 | 92 | 95 | 5 | 8 | 0.58 |

TABLE 8-continued

| Summary of prediction models created using the support vector machine and random forest methodologies. | | | | | | | | | |
|---|---|---|---|---|---|---|---|---|---|
| Classyfire (SVM) | All samples (1st cohort) | AA metabolome | 0.92 | 0.09 | 92 | 91 | 9 | 8 | 0.66 |

TABLE 9

| Cohort 2 patient demographics and clinical information | | |
|---|---|---|
| | DMARD Responders (n = 36) | DMARD Non-Responders (n = 22) |
| Pathotype (n) | Lymphoid (9), Fibroid (8), Myeloid (13), Ungraded (6) | Lymphoid (2), Fibroid (7), Myeloid (9), Ungraded (4) |
| Ethnicity | Caucasian (18), Asian (3), Indian (1), Chinese (1), Black Caribbean (1), Bengali (1), Somalian (1), Black African (2), Afro-Caribbean (1), Bangladeshi (2), Sudanese (1), Pakistan (1), Korean (1), Caribbean (1) | Caucasian (8), Asian (5), Black African (1), Bangladeshi (2), Mixed Greek (1), Black (1), Pakistani (1), British (1), African (1) |
| Gender (n) | Female (13), Male (22) | Female (19), Male (3) |
| Age at Recruitment - years | 51 (±14) | 50 (±10.4) |
| Onset | 4.8 (±2.7) | 4.8 (±3.1) |
| Currently smoking (%) | 7 (20) | 6 (22.3) |
| Co-Morbs Baseline (n) | Osteoarthritis (1), Acne (1), Anaemia (1), Asthma (5), Depression (3), Hypothyroidism (2), Gastro-oesophageal reflux disease (1), anal fistula (1), Hay fever (1), Varicose veins (1), Hypertension (10), Glaucoma (2), Psoriasis (1), Gastric ulcers (1), Diverticulitis (1), Allergy to penicillin (1), Hypercholesterolemia (5), Erectile dysfunction (1), Ischaemic heart disease (2), Diabetes (3), Coronary heart disease (1), Enlarged prostate (1), Carpal tunnel syndrome (1), Low vitamin D (1), GORD (1), Ca prostate (1) | Osteoarthritis (3), Asthma (4), Depression (2), Hypertension (6), Hypercholesterolemia (6), Diabetes (5), Osteopenia (1), Low back pain (1), Anaemia (1), Psoriasis (3), Gout (1), heart block (1), hearing loss (1), laiden deficiency (1), Polcystic ovaries (1), Chest infection (1), Gastritis (1), Fibromyalgia (1), Renal tubular acidosis (1), |
| Concomitant Med. Baseline (n) | NSAIDs (1), Tetracycline (1), Ferrous sulfate (2), Fluoxetine(1), Fluticasone (1), Salbutamol (1), Lansoprazole (2), Levothyroxine (2), Naproxen (5), Gaviscon (1), Movicol (1), Ibuprofen (5), Amlodipine (6), Timolol (1), Latanoprost (1), Omeprazole (2), Tramadol (1), Diclofenac (2), Perindopril (2), Etoricoxib (1), Indapamide (1), Calcium (2), Irbesartan (1), Vitamin D (2), Sibicol (1), Bendroflumethiazide (2), Simvastatin (6), Co-codamol (5), Metformin (3), Ramipril (2), Repaglinide (1), Insulin (2), Sildenafil (1), Aspirin (3), Dipyridamole (1), Isosorbide (1), Calci-chew (1), Doxazosin (1), Prednisolone (1), Lisinopril (2), Atenolol (2), Gabapentin (1), Symbicort (1), Paracetamol (1), Solgar (1), Glucosamine (1), Multivitamin (1), Senokot (1), Amitriptyline (1), Flixotide (1), Ventolin (1), Phyllocontin (1), Tamsulosin (1), Arcoxia (1) | Salbutamol (2), Lansoprazole (3), Levothyroxine (1), Naproxen (2), Ibuprofen (3), Amlodipine (2), Omeprazole (2), Tramadol (2), Diclofenac (3), Irbesartan (1), Vitamin D (1), Bendroflumethiazide (1), Simvastatin (2), Co-codamol (3), Metformin (7), Ramipril (2), Aspirin (1), Doxazosin (2), Lisinopril (1), Gabapentin (1), Paracetamol (4), Ventolin (1), Arcoxia (2), Co-dydramol (3), Gliclazide (3), Atorvastatin (4), Pioglitazone (1), Trimethoprim (1), Lipitor (1), Allopurinol (1), Voltarol (1), Buprenorphine (1), Dihydrocodeine (2), Glucophage (1), Lanus (1), Novorapid (1), Amoxycillin (1), Clarithromycin (1), Losartan (1), Frusemide (1), Vitamin B12 (1), Humalog (2), Exenatide (1), Glucaxide (1), Glargine (1), Citalopram (2), Colecalcif (1), Metatone (1), Paroxitene, (1), Fenobrate (1), Ferrous fu (3), Bisacodyl (1), Pregabalin (1), |
| Recent Steroid Therapy (n) | No (30), Yes (5) | No (20), Yes (2) |
| Steroid Treatment (n) | Depo-Medro (2), Pred (2), Fluticason (1) | Methylpred. (1), Depo-Medro (1) |
| DMARD Treatment (n) | MTX (1), MTX/ASA (10), MTX/ASA/HCQ (5), ASA (1), ASA/HCQ (2), HCQ (1), MTX/HCQ/LEF (1), MTX/HCQ (12) | MTX (4), MTX/ASA/HCQ (2), MTX/ASA (6), MTX/HCQ (2), ASA (2), ASA/HCQ (1), HCQ (1), ASA/LEF (1) |
| ESR (mm/hr) | 42 (±34) | 45 (±26) |
| CRP (mg/l) | 22 (±34) | 31 (±35) |
| CCP (UI/L) | 197 (±218) | 164 (±200) |
| RF (UI/L) | 119 (±187) | 272 (±227) |
| Tiredness VAS (1-100) | 49 (±31) | 51 (±32) |
| Pain VAS (1-100) | 61 (±28) | 55 (±26) |
| Pt. VAS Global Health (1-100) | 62 (±29) | 62 (±30) |
| Physician VAS Global Assess. (1-100) | 60 (±24) | 60 (±25) |

TABLE 9-continued

| Cohort 2 patient demographics and clinical information | |
| --- | --- |
| DMARD Responders (n = 36) | DMARD Non-Responders (n = 22) |
| Tender Joints Baseline (Number/28) | 15 (±8) | 13 (±8) |
| Swollen Joints Baseline (Number/28) | 9 (±6) | 6 (±5) |
| HAQ (Max 38) | 1.46 (±0.75) | 1.85 (±0.68) |
| DAS28 (0-10) | 6.03 (±1.48) | 5.67 (±1.20) |
| Delta DAS28 (difference between 2 time points | −2.59 (±1.18) | 0.14 (±1.0) |
| Response (1) | Responder (36) | Non-responder (22) |
| Response (2) | Good (19), Moderate (17) | Non-responder (22) |
| US Synovial Thickness (12max) (Number/36) | 2 (±0) | |
| US Power Doppler (12max) (Number/36) | 1.5 (±0.5) | |
| US Synovial Thickness (Biopsied Joint) (Number/3) | 13 (±1) | |
| US Power Doppler (Biopsied Joint) (Number/3) | 4 (±1) | |
| Radiographic Erosion (n) | No (20), Yes (6) | No (11), Yes (4) |

Erythrocyte sedimentation rate = ESR, C-reactive protein = CRP, Anti-cyclic citrullinated peptide = CCP, rheumatoid factor = RF, VAS = visual analogue scale, HAQ = Health Assessment Questionnaire, DAS28 = disease activity score-28, US = ultrasound, MTX = methotrexate, ASA = aspirin, HCQ = hydroxychloroquine, LEF = Leflunomide.

Increased Eicosanoid and SPM Concentrations in Peripheral Blood from DMARD Non-Responders

TABLE 10

| Baseline peripheral blood lipid mediator profiles in RA patient cohort 2. | | | | |
| --- | --- | --- | --- | --- |
| | Q1 | Q3 | DMARD Responders Mean ± SEM | DMARD Non-Responders Mean ± SEM |
| DHA bioactive metabolome | | | | |
| RvD1 | 375 | 233 | 0.31 ± 0.19 | 0.50 ± 0.17 |
| RvD2 | 375 | 141 | 0.08 ± 0.04 | 16.96 ± 11.42 |
| RvD3 | 375 | 147 | 0.01 ± 0.01 | 0.10 ± 0.05 |
| RvD4 | 375 | 101 | 0.93 ± 0.27 | 1.98 ± 0.51 |
| RvD5 | 359 | 199 | 0.15 ± 0.04 | 2.39 ± 1.41 |
| RvD6 | 359 | 101 | 0.18 ± 0.03 | 1.72 ± 0.78 |
| 17R-RvD1 | 375 | 233 | 0.49 ± 0.12 | 0.68 ± 0.23 |
| 17R-RvD3 | 375 | 147 | 0.01 ± 0.00 | 0.02 ± 0.02 |
| PD1 | 359 | 153 | 0.38 ± 0.06 | 0.92 ± 0.28 |
| PDX | 359 | 153 | 0.12 ± 0.02 | 1.47 ± 0.60 |
| 17R-PD1 | 359 | 153 | 0.04 ± 0.01 | 0.65 ± 0.34 |
| 22-OH-PD1 | 375 | 153 | 0.09 ± 0.03 | 0.66 ± 0.35 |
| PCTR1 | 650 | 231 | 0.00 ± 0.00 | 0.00 ± 0.00 |
| PCTR2 | 521 | 231 | 0.17 ± 0.06 | 0.13 ± 0.08 |
| PCTR3 | 464 | 231 | 0.36 ± 0.14 | 0.00 ± 0.00 |
| MaR1 | 359 | 221 | 0.44 ± 0.14 | 3.27 ± 0.81 |
| MaR2 | 359 | 191 | 0.08 ± 0.03 | 1.43 ± 0.74 |
| 7S,14S-diHDHA | 359 | 221 | 0.67 ± 0.17 | 2.70 ± 0.70 |
| 4S,14S-diHDHA | 359 | 101 | 0.65 ± 0.09 | 3.79 ± 2.12 |

TABLE 10-continued

| Baseline peripheral blood lipid mediator profiles in RA patient cohort 2. | | | | |
| --- | --- | --- | --- | --- |
| | Q1 | Q3 | DMARD Responders Mean ± SEM | DMARD Non-Responders Mean ± SEM |
| 22-OH-MaR1 | 375 | 221 | 0.74 ± 0.26 | 6.55 ± 1.98 |
| 14-oxo-MaR1 | 357 | 248 | 0.04 ± 0.02 | 0.02 ± 0.01 |
| MCTR1 | 650 | 191 | 0.00 ± 0.00 | 0.00 ± 0.00 |
| MCTR2 | 521 | 191 | 0.44 ± 0.12 | 2.15 ± 0.81 |
| MCTR3 | 464 | 191 | 0.29 ± 0.12 | 1.83 ± 1.14 |
| n-3 DPA bioactive metabolome | | | | |
| RvT1 | 377 | 193 | 0.48 ± 0.45 | 0.00 ± 0.00 |
| RvT2 | 377 | 197 | 2.07 ± 0.18 | 2.40 ± 1.36 |
| RvT3 | 377 | 197 | 0.32 ± 0.11 | 0.43 ± 0.13 |
| RvT4 | 361 | 211 | 1.74 ± 1.03 | 0.93 ± 0.34 |
| $RvD1_{n-3\,DPA}$ | 377 | 215 | 0.78 ± 0.21 | 0.74 ± 0.50 |
| $RvD2_{n-3\,DPA}$ | 377 | 261 | 0.36 ± 0.25 | 0.17 ± 0.06 |
| $RvD5_{n-3\,DPA}$ | 361 | 199 | 0.49 ± 0.22 | 2.69 ± 0.90 |
| $PD1_{n-3\,DPA}$ | 361 | 155 | 0.06 ± 0.03 | 0.10 ± 0.06 |
| 10S,17S-diHDPA | 361 | 155 | 0.08 ± 0.03 | 0.12 ± 0.06 |
| $MaR1_{n-3\,DPA}$ | 361 | 223 | 0.05 ± 0.03 | 1.53 ± 0.69 |
| EPA bioactive metabolome | | | | |
| RvE1 | 349 | 195 | 0.24 ± 0.08 | 0.01 ± 0.01 |
| RvE2 | 333 | 159 | 1.58 ± 0.27 | 5.37 ± 1.62 |
| RvE3 | 333 | 201 | 0.21 ± 0.06 | 0.18 ± 0.10 |

TABLE 10-continued

Baseline peripheral blood lipid mediator
profiles in RA patient cohort 2.

| | Q1 | Q3 | DMARD Responders Mean ± SEM | DMARD Non-Responders Mean ± SEM |
|---|---|---|---|---|
| AA bioactive metabolome | | | | |
| LXA$_4$ | 351 | 115 | 0.02 ± 0.01 | 0.41 ± 0.16 |
| LXB4 | 351 | 221 | 0.80 ± 0.49 | 1.86 ± 0.83 |
| 15R-LXA$_4$ | 351 | 115 | 0.65 ± 0.31 | 3.82 ± 0.82 |
| 15R-LXB$_4$ | 351 | 221 | 1.39 ± 0.30 | 0.44 ± 0.17 |
| 5S,15S-diHETE | 335 | 235 | 2.05 ± 0.44 | 5.87 ± 3.78 |
| LTB$_4$ | 335 | 195 | 18.04 ± 4.20 | 66.04 ± 14.51 |
| 5S,12S-diHETE | 335 | 195 | 0.15 ± 0.07 | 10.51 ± 2.95 |
| 6-trans-LTB$_4$ | 335 | 195 | 0.72 ± 0.14 | 4.79 ± 0.96 |
| 12-epi-6-trans-LTB$_4$ | 335 | 195 | 0.63 ± 0.17 | 9.97 ± 2.10 |
| 20-OH-LTB$_4$ | 351 | 195 | 10.92 ± 3.42 | 34.65 ± 7.93 |
| 20-COOH-LTB$_4$ | 369 | 195 | 1.43 ± 0.48 | 7.26 ± 1.89 |
| LTC$_4$ | 626 | 189 | 51.99 ± 17.43 | 14.45 ± 3.07 |
| LTD$_4$ | 497 | 189 | 14.88 ± 4.12 | 8.14 ± 1.89 |
| LTE$_4$ | 440 | 189 | 91.54 ± 23.83 | 32.76 ± 6.85 |
| PGD$_2$ | 351 | 189 | 0.87 ± 0.15 | 5.84 ± 1.39 |
| PGE$_2$ | 351 | 189 | 1.30 ± 0.31 | 7.13 ± 1.72 |
| PGF$_{2a}$ | 353 | 193 | 2.04 ± 0.62 | 23.01 ± 4.64 |
| TXB$_2$ | 369 | 169 | 53.28 ± 13.57 | 45.37 ± 16.21 |

To gain insights into mechanisms determining the responsiveness of patients to DMARD treatment, we conducted lipid mediator pathway analysis to identify which pathways were differentially regulated between the two patient groups. This demonstrated that there was an upregulation of SPM biosynthetic pathways, including the DHA derived RvD5 and the n-3 DPA derived RvT3 as well as the pro-inflammatory eicosanoids, including the nociceptive mediators PGD$_2$ and PGE$_2$, in DMARD non-responders when compared with responders (FIG. 2). To determine whether the differences in SPM expression were linked with a distinct transcriptional regulation of enzymes involved in SPM biosynthesis we assessed the transcript expression of ALOX enzymes in peripheral blood from these two patient groups. ALOX5, ALOX12, ALOX15 and ALOX15B transcript levels were similar between the DMARD-responders and DMARD-non-responders (FIG. 3). These results suggest that regulation of SPM biosynthetic pathways may be via either the regulation of protein translation or posttranslational modification of the enzymes to regulate their activity (Dalli, J., Chiang, N. & Serhan, C. N. *"Elucidation of novel 13-series resolvins that increase with atorvastatin and clear infections."* Nat Med 21, 1071-1075 (2015) and Fredman, G., et al. Resolvin *"D1 limits 5-lipoxygenase nuclear localization and leukotriene 84 synthesis by inhibiting a calcium-activated kinase pathway."* Proc Natl Acad Sci USA 111, 14530-14535 (2014). The contents of both of which are incorporated herein by reference). Thus, we next tested whether the activity of these enzymes was altered. For this purpose, we measured plasma levels of monohydroxylated fatty acids from all four fatty acid metabolomes to gain insights into their activity in the two patient groups. Assessment of plasma concentrations of 5-HETE, 5HEPE, 7-HDPA and 7-HDHA, markers of ALOX5 activity, revealed a significant upregulation of 7-HDHA, 5-HEPE and 5-HETE in DMARD-non-responders when compared with responders. Concentrations of markers for ALOX12 (14-HDPA and 14-HDHA) and ALOX15 (17-HDPA, 17-HDHA, 15-HEPE and 15-HETE) also demonstrated an increased in activity for these enzymes in non-responders (FIG. 4). Thus, these findings indicate that the observed increases in plasma SPM in non-responders was due to increased ALOX activity. To further evaluate the origin of these proposed pathway markers we conducted chiral liquid chromatography tandem mass spectrometry which permits the separation the R and S isomers of a given hydroxylated fatty acid. Here we found that in plasma of both DMARD responders and DMARD non-responders the most abundant isomer for all the monohydroxylated fatty acids tested was that carrying the alcohol in the S conformation (FIG. 14). Given that all four ALOX enzymes involved in SPM biosynthesis preferentially oxygenate fatty acids in the S conformation, these results indicate an increased ALOX activity in non-responders.

Example 2—Baseline RvD4, 10S, 17S-diHDPA, 15R-LXA$_4$, MaR1$_{n-3\ DPA}$ Concentrations are Predictive of DMARD-Treatment Outcome in RA Patients Having found that lipid mediator profiles are predictive of responsiveness to DMARD treatment in RA patients we next investigated whether we could identify specific lipid mediators that may be useful as biomarkers for treatment responsiveness. For this purpose, we conducted a random forest "importance" analysis that identifies the relevance of every mediator in the performance of the model based on the prediction accuracy. Here we found that the DHA-derived RvD4 (4S,5R,17S-trihydroxy-6E,8E,10Z,13Z,15E,19Z-docosahexaenoic acid) and 10S, 17S-diHDPA (10S,17S-dihydroxy-7Z,11E,13Z,15E,19Z-docosapentaenoic acid) were the most important mediators in predicting treatment responsiveness, with 15R-LXA$_4$ (5S,6R,15R-trihydroxy-7E,9E, 11Z,13E-eicosatetraenoic acid), 5S,12S-diHETE (5S,12S-dihydroxy-6E,8Z,10E,14Z-eicosatetraenoic acid), 4S, 14S-diHDHA (4S,14S-dihydroxy-5E,7Z,10Z,12E,16Z,19Z-docosahexaenoic acid) and n-3 DPA derived Maresin 1 (MaR1$_{n-3\ DPA}$) (7R,14S-dihydroxy-8E,10E,12Z,16Z,19Z-docosapentaenoic acid) also displaying a marked contribution although to a lesser extent than the RvD4 and 10S, 17S-diHDPA (FIG. 1F). Having identified potential candidate biomarkers, we next built machine-learning models using the random forest methodology and concentrations of either RvD4, 10S, 17S-diHDPA, 15R-LXA$_4$ and MaR1n-3 DPA or RvD4, 10S, 17S-diHDPA, 15R-LXA$_4$, 5S,12S-diHETE, 4S,14S-diHDHA, MaR1$_{n-3\ DPA}$ using a second group of DMARD naive patients (see Table 9 and 10 for patient clinical parameters and lipid mediator concentrations) and tested the ability of this model to assign patients to the correct outcome group. Here we found that the combination of the two mediators alone predicted treatment outcome in ~86% of the cases while the model build using the four mediators gave a better prediction score of ~83% (FIG. 1G). We next validated the accuracy of these two models using mediator concentrations from a different group of DMARD naive patients. Results from these experiments demonstrated that the model build using the four mediators gave an AUC of 0.80, whereas the model built with the six mediators gave an AUC score of 0.79 (FIG. 1H). Of note, the AUC for these mediators were markedly better than those obtained using mediator concentrations from the n-3 DPA metabolome and disease scores (FIG. 1D).

Example 3—Pre-Treatment Lipid Mediator Profiles Identify Distinct Disease Pathotypes Recent studies demonstrate that based on synovial molecular and histological features patients with RA can be classified into three categories Lympho-myeloid, Diffuse-myeloid and Pauci-immune-fibroid that are associated with distinct disease evolution and responses to DMARD treatment (Humby, F., et al. *"Synovial cellular and molecular signatures stratify clinical response to csDMARD therapy and predict radiographic progression in early rheumatoid arthritis patients." Ann Rheum Dis* (2019), the contents of which are incorporated herein by reference). Therefore, we next questioned whether immune-related features in each of these groups extended beyond the synovium into the systemic circulation. To address this question, we conducted lipid mediator profiling to assess whether peripheral blood lipid mediator concentrations in RA patients from each of these three groups were distinct prior to the initiation of DMARD therapy. Using PLS-DA we found that plasma lipid mediators were indeed characteristic for different disease pathotypes i.e. distinct lipid mediator profiles clustered with each category (FIG. 5A). Assessment of the variable importance in projection (VIP) scores, which identify the contribution of each mediator in the observed separation between groups demonstrated an upregulation of pro-resolving mediators, including 15R-LXA$_4$ and MCTR2, in peripheral blood from patients with the Pauci-immune-fibroid pathotype. In plasma from these patients we also found an upregulation of pro-inflammatory and immunosuppressive mediators including PGD$_2$ and TxA2, measured as its stable the further metabolite TxB2 (FIG. 5B).

We next investigated the differential regulation of lipid mediator profiles between DMARD-responders and non-responders for each of these three pathotypes. Here we found an increase in ALOX5 products from both the n-3 DPA and DHA metabolomes in non-responders with Lympho-myeloid and those with a Pauci-immune-fibroid pathotype when compared with responders with the respective pathotypes. These included significant increases in the DHA-derived RvD4, and PDX. Assessment of mediators from the AA and EPA metabolomes demonstrated an increase in ALOX5 products in non-responders with Lympho-myeloid and Pauci-immune-fibroid pathotypes that reached statistical significance in patients with a Pauci-immune-fibroid pathotype for the leukotriene (LT) B4 pathway including its further metabolite 20-COOH-LTB$_4$. In these patients we also found a statistically significant increase of the pro-inflammatory and nociceptive mediator PGE$_2$ (FIG. 6). These results demonstrate that differences in peripheral blood lipid mediator profiles between DMARD-responders and non-responders are common to different RA pathotypes.

Having found that lipid mediator concentrations were different between these patient groups, we next assessed whether combining disease pathotypes with the biomarkers identified above would further enhance the predictiveness of our machine learning model. Results from this analysis demonstrate a marked increase in the predictiveness of RvD4, 10S, 17S-diHDPA, 15R-LXA$_4$ and MaR1$_{n-3\ DPA}$ at identifying responders, when separate machine learning models were built for each of the RA pathotypes, with the ability of the model to correctly classify responders increasing to ~89% (FIG. 5D).

Example 4—Increased SPM in DMARD-Responders when Compared to Non-Responders 6 Months after Treatment Having observed a differential regulation in peripheral blood SPM concentrations between DMARD-responders and DMARD-non-responders prior to treatment initiation we next investigated whether differences in peripheral blood lipid mediator concentrations were also present in patients 6 months after treatment initiation. OPLS-DA analysis demonstrated that plasma lipid mediator profiles from DMARD responders 6 months after the initiation of treatment were distinct from those of DMARD-non-responders, as demonstrated by a separation between the two patient clusters (FIG. 7A, Table 11). Assessment of VIP scores identified 21 mediators and SPM pathway markers that were differentially expressed between the two patient groups (FIG. 7B). Amongst these mediators we found SPM that are involved in coordinating the host response during ongoing inflammation such as PCTR2, RvD2 and RvD3 (Arnardottir, H. H., et al. Resolvin *"D3 Is Dysregulated in Arthritis and Reduces Arthritic Inflammation." J Immunol* 197, 2362-2368 (2016), Chiang, N., Dalli, J., Colas, R. A. & Serhan, C. N. *"Identification of resolvin D2 receptor mediating resolution of infections and organ protection"*. J Exp Med 212, 1203-1217 (2015), and Dalli, J., Ramon, S., Norris, P. C., Colas, R. A. & Serhan, C. N. *Novel proresolving and tissue-regenerative resolvin and protectin sulfido-conjugated pathways. FASEB J* 29, 2120-2136 (2015), the contents of all of which are incorporated by reference) as well as mediators linked with pain modulation e.g. RvE1 and RvE2 (Barden, A. E., et al. *"Specialised pro-resolving mediators of inflammation in inflammatory arthritis"*. *Prostaglandins Leukot Essent Fatty Acids* 107, 24-29 (2016) and Xu, Z. Z., et al. *"Resolvins RvE1 and RvD1 attenuate inflammatory pain via central and peripheral actions." Nat Med* 16, 592-597, 591p following 597 (2010), the contents of both of which are incorporated by reference) (FIG. 7B).

TABLE 11

| Peripheral blood lipid mediator profiles in patients with RA after 6 months of DMARD treatment. | | | | |
|---|---|---|---|---|
| | Q1 | Q3 | DMARD Responders Mean ± SEM | DMARD Non-Responders Mean ± SEM |
| DHA bioactive metabolome | | | | |
| RvD1 | 375 | 233 | 0.09 ± 0.06 | 0.60 ± 0.19 |
| RvD2 | 375 | 141 | 0.97 ± 0.44 | 0.18 ± 0.13 |
| RvD3 | 375 | 147 | 0.13 ± 0.05 | 0.02 ± 0.02 |
| RvD4 | 375 | 101 | 1.38 ± 0.41 | 0.93 ± 0.26 |
| RvD5 | 359 | 199 | 0.30 ± 0.12 | 0.32 ± 0.11 |
| RvD6 | 359 | 101 | 0.52 ± 0.10 | 0.55 ± 0.16 |
| 17R-RvD1 | 375 | 233 | 0.13 ± 0.07 | 0.27 ± 0.13 |
| 17R-RvD3 | 375 | 147 | 0.07 ± 0.04 | 0.10 ± 0.07 |
| PD1 | 359 | 153 | 1.14 ± 0.19 | 0.78 ± 0.27 |
| PDX | 359 | 153 | 0.92 ± 0.36 | 9.23 ± 3.38 |
| 17R-PD1 | 359 | 153 | 0.64 ± 0.51 | 5.98 ± 2.01 |
| 22-OH-PD1 | 375 | 153 | 0.07 ± 0.04 | 0.06 ± 0.05 |
| PCTR1 | 650 | 231 | 2.25 ± 1.59 | 0.00 ± 0.00 |
| PCTR2 | 521 | 231 | 0.39 ± 0.14 | 0.05 ± 0.05 |
| PCTR3 | 464 | 231 | 0.00 ± 0.00 | 0.00 ± 0.00 |
| MaR1 | 359 | 221 | 6.82 ± 1.39 | 5.83 ± 1.30 |
| MaR2 | 359 | 191 | 0.64 ± 0.38 | 0.00 ± 0.00 |
| 7S,14S-diHDHA | 359 | 221 | 2.21 ± 0.78 | 2.79 ± 0.69 |
| 4S,14S-diHDHA | 359 | 101 | 3.89 ± 3.28 | 1.51 ± 0.37 |
| 22-OH-MaR1 | 375 | 221 | 2.21 ± 0.95 | 2.07 ± 1.78 |
| 14-oxo-MaR1 | 357 | 248 | 0.32 ± 0.32 | 2.35 ± 0.86 |
| MCTR1 | 650 | 191 | 0.00 ± 0.00 | 0.00 ± 0.00 |
| MCTR2 | 521 | 191 | 0.97 ± 0.23 | 0.28 ± 0.19 |
| MCTR3 | 464 | 191 | 3.32 ± 0.98 | 4.71 ± 1.61 |
| n-3 DPA bioactive metabolome | | | | |
| RvT1 | 377 | 193 | 0.34 ± 0.13 | 0.23 ± 0.12 |
| RvT2 | 377 | 197 | 0.04 ± 0.04 | 0.16 ± 0.10 |
| RvT3 | 377 | 197 | 0.00 ± 0.00 | 0.00 ± 0.00 |

TABLE 11-continued

Peripheral blood lipid mediator profiles in patients
with RA after 6 months of DMARD treatment.

| | Q1 | Q3 | DMARD Responders Mean ± SEM | DMARD Non-Responders Mean ± SEM |
|---|---|---|---|---|
| RvT4 | 361 | 211 | 0.31 ± 0.09 | 0.93 ± 0.27 |
| RvD1$_{n-3\ DPA}$ | 377 | 143 | 1.19 ± 0.31 | 1.02 ± 0.27 |
| RvD2$_{n-3\ DPA}$ | 377 | 261 | 1.54 ± 0.27 | 1.68 ± 0.58 |
| RvD5$_{n-3\ DPA}$ | 361 | 199 | 1.26 ± 0.21 | 1.38 ± 0.28 |
| PD1$_{n-3\ DPA}$ | 361 | 155 | 0.37 ± 0.08 | 0.34 ± 0.11 |
| 10S,17S-diHDPA | 361 | 155 | 0.28 ± 0.07 | 0.16 ± 0.11 |
| MaR1$_{n-3\ DPA}$ | 361 | 249 | 0.02 ± 0.02 | 0.10 ± 0.07 |
| EPA bioactive metabolome | | | | |
| RvE1 | 349 | 161 | 0.09 ± 0.07 | 0.00 ± 0.00 |
| RvE2 | 333 | 199 | 5.26 ± 1.02 | 3.62 ± 1.44 |
| RvE3 | 333 | 201 | 0.87 ± 0.26 | 0.90 ± 0.23 |
| AA bioactive metabolome | | | | |
| LXA$_4$ | 351 | 115 | 0.11 ± 0.03 | 0.08 ± 0.03 |
| LXB4 | 351 | 221 | 0.17 ± 0.08 | 0.36 ± 0.23 |
| 15R-LXA$_4$ | 351 | 115 | 0.76 ± 0.15 | 1.78 ± 0.54 |
| 15R-LXB$_4$ | 351 | 221 | 5.11 ± 0.60 | 9.37 ± 1.39 |
| 5S,15S-diHETE | 335 | 115 | 26.99 ± 7.61 | 26.54 ± 3.89 |
| LTB$_4$ | 335 | 195 | 52.21 ± 10.73 | 108.07 ± 50.98 |
| 5S,12S-diHETE | 335 | 195 | 1.57 ± 0.69 | 0.85 ± 0.33 |
| 6-trans-LTB$_4$ | 335 | 195 | 1.67 ± 0.28 | 5.35 ± 3.63 |
| 12-epi-6-trans-LTB$_4$ | 335 | 195 | 1.95 ± 0.33 | 4.63 ± 2.24 |
| 20-OH-LTB$_4$ | 351 | 195 | 24.47 ± 7.22 | 42.62 ± 18.36 |
| 20-COOH-LTB$_4$ | 369 | 195 | 0.16 ± 0.03 | 0.42 ± 0.33 |
| LTC$_4$ | 626 | 189 | 13.21 ± 4.65 | 20.10 ± 6.85 |
| LTD$_4$ | 497 | 189 | 6.86 ± 1.69 | 5.65 ± 1.31 |
| LTE$_4$ | 440 | 189 | 41.48 ± 12.00 | 87.57 ± 44.40 |
| PGD$_2$ | 351 | 189 | 7.48 ± 1.87 | 12.26 ± 5.93 |
| PGE$_2$ | 351 | 189 | 11.10 ± 3.55 | 11.29 ± 4.59 |
| PGF$_{2a}$ | 353 | 193 | 11.24 ± 2.30 | 13.45 ± 3.42 |
| TXB$_2$ | 369 | 169 | 190.70 ± 72.02 | 168.15 ± 85.85 |

In order to gain further insights into the mediator pathways that were differentially regulated between these patient groups we interrogated the biosynthetic pathways for each of the essential fatty acid metabolomes. This analysis demonstrated that the concentrations of ALOX5 and ALOX15-derived mediators from both the n-3 DPA and DHA metabolomes were reduced in the plasma of non-responders when compared to responders (FIG. 7C). Pathway analysis of EPA and AA-derived lipid mediator concentrations demonstrated that while ALOX5 derived products of EPA were also reduced, AA-derived ALOX5 products, including those of the potent leukocyte chemoattractant LTB$_4$ and the ionotropic cysteinyl leukotrienes (Radmark, O., Werz, O., Steinhilber, D. & Samuelsson, B. "5-*Lipoxygenase, a key enzyme for leukotriene biosynthesis in health and disease*". Biochim Biophys Acta 1851, 331-339 (2015), the contents of which are incorporated herein by reference), were markedly increased in plasma from non-responders when compared with responders (FIG. 7D).

Having observed significant decreases in SPM concentrations we next investigated whether the activity of ALOX enzymes and the conversion of DHA and n-3 DPA was altered in peripheral blood cells from the two patient groups. For this purpose, we measured plasma levels of monohydroxylated fatty acids from the DHA and n-3 DPA metabolomes to gain insights into both enzyme activity and substrate conversion. Plasma concentrations of the ALOX5 products 7-HDPA and 7-HDHA were either similar (7-HDPA) between the two patient groups, or upregulated (7-HDHA) in DMARD-non-responders. Concentrations of the ALOX12 (14-HDPA and 14-HDHA) and ALOX15 (17-HDHA and 17-HDPA) products were increased in non-responders (FIG. 8). Of note, as observed in baseline plasma, chiral analysis of monohydroxylated fatty acids demonstrated that the predominant isomer for each of these products was the S-isomer (FIG. 15). These findings indicate that the observed reduction in plasma DHA and n-3 DPA derived SPM in DMARD non-responders was not due to a decrease in ALOX activity and/or substrate availability/conversion in peripheral blood cells from these patients. Together these observations demonstrate that 6 months after treatment initiation plasma SPM concentrations in DMARD responders were higher than those measured in DMARD non-responders. Given that enzyme activity was elevated in non-responders when compared with responders, this suggests that uncoupling of the SPM biosynthetic pathways may be responsible for the reductions in plasma SPM concentrations.

Example 5—SPM Mediate the Protective Actions of MTX in Experimental Inflammatory Arthritis Since SPM were elevated after treatment initiation in responders when compared with non-responders, and given that MTX is the anchor drug in the treatment of these patients, we next questioned whether MTX regulated SPM production. Incubation of human whole blood with MTX at a clinically relevant and comparable concentration (Edno, L., et al. "*Total and free methotrexate pharmacokinetics in rheumatoid arthritis patients*". Ther Drug Monit 18, 128-134 (1996), the contents of which are incorporated herein by reference) led to an increase in plasma SPM concentrations as demonstrated by rightward shift in the SPM cluster in the OPLS-DA analysis. This shift was linked with an upregulation of mediators from the DHA, n-3 DPA and EPA bioactive metabolomes including DHA-derived PDX and RvD1 as well as the EPA-derived RvE3 (FIG. 9A-C and Table 12).

In order to test whether findings made with human cells in vitro were also translatable to the in vivo scenario we next assessed whether MTX also upregulated SPM levels in mice. Administration of MTX to mice led to a dose-dependent shift in the peripheral blood SPM profile. Of note this shift was linked with an upregulation of several ALOX15-derived SPM including RvT1, RvT4 and RvD5$_{n-3\ DPA}$ (FIG. 9D-E and Table 13). We next tested whether the regulation of SPM was central to the joint protective actions of MTX in experimental inflammatory arthritis. For this purpose, we administered MTX to wild type (WT) mice and mice that lack ALOX15 (Alox15l and assessed joint disease activity. As anticipated, administration of MTX to WT mice led to a significant reduction in clinical scores, an improvement in weight loss and a decrease in paw edema (FIG. 10A-C). In these studies, we also found a decrease in the number of eosinophils, neutrophils, monocytes and macrophages that were recruited to the joint as well as a reduction in inflammatory eicosanoid concentrations (FIGS. 10D and 11). Of note the protective actions of MTX were lost in mice lacking the ALOX15 enzyme. In these mice, MTX no longer regulated disease activity, weight loss (FIG. 10A-C), leukocyte trafficking (FIG. 10D) as well as peripheral blood and circulating eicosanoid concentrations (FIG. 11). Therefore, these findings indicate that MTX upregulates SPM production and loss of these endogenous pathways reverses the joint protective actions of this DMARD.

TABLE 12

Methotrexate upregulates plasma SPM concentrations

| | Vehicle<br>Mean ± SEM | Methotrexate<br>Mean ± SEM |
|---|---|---|
| DHA bioactive metabolome | | |
| RvD1 | 1.63 ± 0.26 | 9.09 ± 1.13 |
| RvD2 | 0.43 ± 0.18 | 0.32 ± 0.13 |
| RvD3 | 0.28 ± 0.05 | 3.57 ± 1.38 |
| RvD4 | 0.49 ± 0.18 | 1.44 ± 0.59 |
| RvD5 | 0.65 ± 0.10 | 1.05 ± 0.22 |
| RvD6 | 0.17 ± 0.07 | 1.07 ± 0.21 |
| 17R-RvD1 | 2.64 ± 0.57 | 7.50 ± 1.97 |
| 17R-RvD3 | 0.49 ± 0.17 | 2.68 ± 0.67 |
| PD1 | 1.97 ± 0.31 | 2.11 ± 0.24 |
| PDx | 0.09 ± 0.04 | 1.55 ± 0.22 |
| 17R-PD1 | 0.31 ± 0.10 | 0.96 ± 0.39 |
| 22-OH-PD1 | 0.00 ± 0.00 | 7.86 ± 2.61 |
| MaR1 | 6.60 ± 0.65 | 24.53 ± 3.12 |
| MaR2 | 1.01 ± 0.41 | 0.00 ± 0.00 |
| 7S,14S-diHDHA | 0.18 ± 0.07 | 0.00 ± 0.00 |
| 4S,14S-diHDHA | 2.45 ± 0.61 | 2.82 ± 0.56 |
| 22-OH-MaR1 | 12.67 ± 2.20 | 18.44 ± 4.31 |
| 14-oxo-MaR1 | 0.00 ± 0.00 | 0.00 ± 0.00 |
| n-3 DPA bioactive metabolome | | |
| RvT1 | 5.10 ± 0.93 | 9.18 ± 2.50 |
| RvT2 | 0.19 ± 0.08 | 1.63 ± 0.35 |
| RvT3 | 0.17 ± 0.07 | 0.60 ± 0.24 |
| RvT4 | 0.26 ± 0.11 | 0.36 ± 0.15 |
| RvD1$_{n-3 DPA}$ | 13.69 ± 4.33 | 5.43 ± 1.10 |
| RvD2$_{n-3 DPA}$ | 0.70 ± 0.23 | 3.58 ± 1.16 |
| RvD5$_{n-3 DPA}$ | 0.79 ± 0.25 | 1.26 ± 0.24 |
| PD1$_{n-3 DPA}$ | 0.29 ± 0.08 | 0.34 ± 0.10 |
| PD2$_{n-3 DPA}$ | 0.19 ± 0.08 | 3.01 ± 1.23 |
| 10S,17S-diHDPA | 0.16 ± 0.05 | 0.55 ± 0.16 |
| MaR1$_{n-3 DPA}$ | 0.00 ± 0.00 | 1.09 ± 0.29 |
| MaR2$_{n-3 DPA}$ | 7.84 ± 1.30 | 7.97 ± 0.87 |
| &s,14S-diHDPA | 1.52 ± 0.28 | 2.04 ± 0.41 |
| EPA bioactive metabolome | | |
| RvE1 | 0.54 ± 0.22 | 1.15 ± 0.32 |
| RvE2 | 0.38 ± 0.15 | 3.82 ± 1.15 |
| RvE3 | 1.70 ± 0.22 | 4.49 ± 0.23 |
| AA bioactive metabolome | | |
| LXA$_4$ | 0.34 ± 0.10 | 0.55 ± 0.10 |
| LXB4 | 5.19 ± 0.95 | 13.42 ± 2.93 |
| 15R-LXA$_4$ | 3.62 ± 0.53 | 5.44 ± 1.47 |
| 15R-LXB$_4$ | 1.72 ± 0.36 | 2.13 ± 0.45 |
| 5S,15S-diHETE | 6.98 ± 0.64 | 5.32 ± 0.43 |
| 13,14-dehydro-15-oxo-LXA$_4$ | 5.11 ± 0.57 | 82.74 ± 32.78 |
| 15-oxo-LXA$_4$ | 3.09 ± 0.71 | 3.78 ± 0.56 |

Human whole blood was incubated with MTX (100 nM, 37° C., 45 min). Incubations were quenched and SPM were identified and quantified using LC-MS/MS-based lipid mediator profiling. Results are mean±SEM. n=6 volunteers per group.

TABLE 13

Methotrexate upregulates plasma SPM concentrations in mice

| | Vehicle<br>Mean ± SEM | Methotrexate<br>(1 µg/mouse)<br>Mean ± SEM | Methotrexate<br>(22 µg/mouse)<br>Mean ± SEM |
|---|---|---|---|
| DHA bioactive metabolome | | | |
| RvD1 | 3.85 ± 1.35 | 1.39 ± 0.59 | 0.14 ± 0.12 |
| RvD2 | 1.87 ± 0.92 | 2.60 ± 1.05 | 2.99 ± 0.66 |
| RvD3 | 1.47 ± 0.45 | 1.30 ± 0.56 | 0.18 ± 0.66 |
| RvD4 | 2.07 ± 0.19 | 3.70 ± 0.70* | 3.88 ± 0.55* |
| RvD5 | 0.79 ± 0.44 | 1.64 ± 0.67 | 0.00 ± 0.00 |
| RvD6 | 1.00 ± 0.49 | 1.72 ± 0.72 | 0.00 ± 0.00 |
| 17R-RvD1 | 3.39 ± 1.61 | 0.00 ± 0.00* | 0.26 ± 0.30 |
| 17R-RvD3 | 0.00 ± 0.00 | 4.26 ± 0.87* | 0.67 ± 0.65 |
| PD1 | 7.25 ± 1.65 | 10.13 ± 4.31 | 9.99 ± 2.47 |
| PDx | 23.81 ± 1.98 | 17.23 ± 1.32 | 10.36 ± 2.79 |
| 17R-PD1 | 0.58 ± 2.51 | 10.50 ± 4.91 | 1.41 ± 0.61 |
| 22-OH-PD1 | 0.00 ± 0.00 | 0.00 ± 0.00 | 0.00 ± 0.00 |
| MaR1 | 20.64 ± 7.26 | 71.74 ± 20.71 | 37.97 ± 11.63 |
| MaR2 | 1.16 ± 0.72 | 2.05 ± 0.39 | 1.28 ± 0.72 |
| 7S,14S-diHDHA | 0.00 ± 0.00 | 0.00 ± 0.00 | 22.10 ± 8.55 |
| 22-OH-MaR1 | 0.00 ± 0.00 | 0.00 ± 0.00 | 0.00 ± 0.00 |
| 14-oxo-MaR1 | 1.18 ± 0.57 | 3.44 ± 0.37* | 0.81 ± 0.41 |
| 4S,14S-diHDHA | 3.04 ± 0.38 | 18.38 ± 6.59* | 1.43 ± 0.64 |
| n-3 DPA bioactive metabolome | | | |
| RvT1 | 2.61 ± 1.28 | 10.18 ± 2.01* | 9.49 ± 5.15 |
| RvT2 | 0.00 ± 0.00 | 0.00 ± 0.00 | 0.00 ± 0.00 |
| RvT3 | 0.00 ± 0.28 | 0.63 ± 0.28 | 0.87 ± 0.48 |
| RvT4 | 0.00 ± 0.00 | 1.40 ± 0.64* | 2.07 ± 1.16 |
| RvD1$_{n-3 DPA}$ | 0.00 ± 0.00 | 0.67 ± 0.35 | 0.33 ± 0.48 |
| RvD2$_{n-3 DPA}$ | 4.52 ± 2.14 | 4.54 ± 1.98 | 3.72 ± 3.41 |
| RvD5$_{n-3 DPA}$ | 0.97 ± 0.47 | 4.02 ± 0.79* | 0.00 ± 0.00 |
| PD1$_{n-3 DPA}$ | 0.00 ± 0.00 | 0.00 ± 0.00 | 0.28 ± 0.24 |
| 10S,17S-diHDPA | 5.44 ± 3.53 | 2.41 ± 0.97 | 0.52 ± 0.45 |
| MaR1$_{n-3 DPA}$ | 0.89 ± 0.42 | 0.83 ± 0.34 | 0.00 ± 0.00 |
| 7S,14S-diHDPA | 1.01 ± 0.64 | 0.00 ± 0.00 | 0.64 ± 0.55 |
| EPA bioactive metabolome | | | |
| RvE1 | 0.00 ± 0.00 | 0.54 ± 0.25* | 0.00 ± 0.00 |
| RvE2 | 0.52 ± 0.34 | 1.70 ± 0.52* | 0.96 ± 0.22 |
| RvE3 | 2.46 ± 0.45 | 6.22 ± 1.39 | 0.77 ± 0.64 |
| AA bioactive metabolome | | | |
| LXA$_4$ | 2.64 ± 1.33 | 1.06 ± 0.20 | 0.56 ± 0.15 |
| LXB4 | 22.18 ± 3.96 | 16.93 ± 1.92 | 12.72 ± 1.68 |
| 15R-LXA$_4$ | 18.83 ± 4.88 | 6.41 ± 0.78 | 6.20 ± 1.44 |
| 15R-LXB$_4$ | 1.41 ± 0.80 | 3.90 ± 1.80 | 2.17 ± 0.89 |
| 5S,15S-diHETE | 0.91 ± 0.50 | 14.61 ± 6.53 | 12.65 ± 5.37 |
| 13,14-dehydro-15-oxo-LXA$_4$ | 0.83 ± 0.50 | 0.65 ± 0.21 | 0.20 ± 0.15 |
| 15-oxo-LXA$_4$ | 2.20 ± 0.60 | 3.53 ± 1.62 | 3.93 ± 1.01 |

Mice were administered the indicated doses of MTX or vehicle (saline) via intravenous injection. Blood was collected after 1 hour and SPM concentrations were determined using LC-MS/MS based lipid mediator profiling.
*p < 0.05 using t-test corrected using Benjamin Hochberg adjustment with an FDR of 0.1.

Example 6—Activation of p-300 and MAPK by MTX Increases SPM Production and Protects During Experimental Inflammatory Arthritis Distinct signalling pathways, including those downstream of CREB-binding protein and its homologue p300 (CBP/p300) as well as p38 mitogen-activated protein kinase (MAPK), are implicated in mediating the cellular actions of MTX in target cells, including leukocytes (Thornton, C. C., et al. "*Methotrexate-mediated activation of an AMPK-CREB-dependent pathway: a novel mechanism for vascular protection in chronic systemic inflammation*". *Ann Rheum Dis* 75, 439-448 (2016) and Wu, C. W., et al. "*Combined*

*treatment with vitamin C and methotrexate inhibits triple-negative breast cancer cell growth by increasing $H_2O_2$ accumulation and activating caspase-3 and p38 pathways".* Oncol Rep 37, 2177-2184 (2017), the contents of both of which are incorporated herein by reference). Given that these two pathways are also implicated in the regulation of ALOX15 expression (Shankaranarayanan, P., Chaitidis, P., Kuhn, H. & Nigam, S. *"Acetylation by histone acetyltransferase CREB-binding protein/p300 of STAT6 is required for transcriptional activation of the 15-lipoxygenase-1 gene". J Biol Chem* 276, 42753-42760 (2001), Xu, B., et al. "Interleukin-13 *induction of 15-lipoxygenase gene expression requires p38 mitogen-activated protein kinase-mediated serine 727 phosphorylation of Stat1 and Stat3." Mol Cell Biol* 23, 3918-3928 (2003) and Fredman, G., et al. *"An imbalance between specialized pro-resolving lipid mediators and pro-inflammatory leukotrienes promotes instability of atherosclerotic plaques". Nat Commun* 7, 12859 (2016) the contents of all of which are incorporated by reference) we next questioned whether they were involved in the observed increases in SPM production by MTX. For this purpose, we employed a pharmacological approach to assess whether inhibitors to these pathways blocked MTX-induced upregulation of SPM in human peripheral blood. Here we found that incubation of whole blood with inhibitors to both CBP/p300 (L002) and MAPK (SB202190) markedly shifted the plasma lipid mediator profile blocking the MTX-induced upregulation of SPM, decreasing the concentrations of several mediators including PD1, MaR2n-3 DPA and in the anti-arthritic RvD1 (Norling, L. V., et al. *"Proresolving and cartilage-protective actions of resolvin D1 in inflammatory arthritis".* JCI Insight 1, e85922 (2016), the contents of which are incorporated by reference) (FIG. 12A, B). We next tested whether inhibition of these pathways also reversed the anti-arthritic actions of MTX in experimental inflammatory arthritis. Here we found that administration of either L002 or SB202190 reversed the anti-arthritic actions of MTX, as measured by an increase in joint inflammation, an increase in joint damage, and an increase in weight loss, a marker of disease activity (FIG. 12C-E). Administration of these inhibitors also reversed the ability of MTX to regulate neutrophil trafficking to the inflamed joint, an observation that was linked with an increase in the joint concentrations of the potent leukocyte chemoattractant LTB4 (FIG. 12F, G). Thus, pharmacological inhibition of CBP/p300 or MAPK abrogates the beneficial effects of MTX on ALOX15 activity and the downstream beneficial effects on joint disease. These findings suggest that via the activation of CBP/p300 and MAPK, MTX regulates the activity of ALOX15 upregulating SPM production, dampening joint inflammation and joint damage during inflammatory arthritis.

Example 7—Summary of Suitable Sample Processing Method

Plasma samples will be collected placed in methanol containing deuterium labelled internal standards ($d_4$_LTB$_4$, da-5S-HETE, $d_4$-PGE$_2$, $d_5$-LXA$_4$ and $d_5$-RvD2, 500 pg each). These were then kept at $-20°$ C. for 45 minutes to allow for protein precipitation and subjected to solid phase extraction as per previous publication (Dalli et al 2018). Methyl formate fractions were then brought to dryness using a TurboVap LP (Biotage) and products suspended in water-methanol (50:50 vol:vol) for LC-MS-MS. A Shimadzu LC-20AD HPLC and a Shimadzu SIL-20AC autoinjector (Shimadzu, Kyoto, Japan), paired with a QTrap 5500 (AB-Sciex, Warrington, UK) were utilised and operated as described (Dalli et al 2018). To monitor each lipid mediator and respective pathways, a Multiple Reaction Monitoring (MRM) method was developed with diagnostic ion fragments and identification using recently published criteria (Dalli et al 2018), including matching retention time (RT) to synthetic and authentic materials and at least six diagnostic ions for each lipid mediator. Calibration curves were obtained for each using authentic compound mixtures and deuterium labeled lipid mediator at 0.78, 1.56, 3.12, 6.25, 12.5, 25, 50, 100, and 200 μg. Linear calibration curves were obtained for each lipid mediator, which gave r2 values of 0.98-0.99. All analyses were conducted blind.

Levels of the mediators levels for the following lipid mediator families:

Lipoxins, leukotrienes, prostaglandins and thromboxane from Arachidonic acid; E-series resolvins from eciosapentaenoic acid; resolvins, protectins and maresins from n-3 docosapentanoic acid and resolvins, protectins and maresins from docosahexaenoic acid as well as their pathway markers and further metabolites will be measured in plasma from these patients and compared to an established database compiled using deeply phenotyped patient samples from patients that were responsive and non-responsive to the treatments of interest.

Materials & Methods

The following materials and methods relate to all of the Examples above.

Liquid chromatography (LC)-grade solvents were purchased from Fisher Scientific (Pittsburgh, PA, USA); Poroshell 120 EC-C18 column (100 mm×4.6 mm×2.7 μm) was obtained from Agilent (Cheshire, UK); C18 SPE columns were from Biotage (Uppsala, SE); synthetic standards for LC-tandem mass spectrometry (MS-MS) quantitation and deuterated (d) internal standards (da-5S-HETE, d5-RvD2, $d_5$-LXA$_4$, $d_4$-PGE$_2$, and $d_4$-LTB$_4$) were purchased from Cambridge Bioscience (Cambridge, UK) or provided by Charles N. Serhan (Harvard Medical School, Boston, Massachusetts, USA; supported by NIH-funded P01GM095467); Methotrexate (MTX, Sigma); Dulbecco's Phosphate-Buffered Saline (DPBS, without calcium and magnesium, Sigma); Whole Blood Lysing Reagent Kit (Beckman Coulter, Inc.). L002 and SC202190 (Cayman Chemicals).

Pathobiology of Early Arthritis Cohort

Baseline and 6 months post treatment plasma samples were obtained from the Pathobiology of Early Arthritis Cohort (PEAC). The PEAC cohort study was approved by the King's College Hospital Research Ethics Committee (REC 05/Q0703/198). Following written informed consent, peripheral blood samples and synovial tissue were obtained from patients recruited at Barts Health NHS Trust into the Pathobiology of Early Arthritis Cohort (PEAC, http://www.peac-mrc.mds.qmul.ac.uk) undergoing ultrasound (US)-guided synovial biopsy of the most inflamed joint (knee, wrist or small joints of hands or feet)[5]. All patients were disease modifying anti-rheumatic drugs (DMARDs) and steroid-naïve, had symptoms duration less than 12 months and fulfilled the ACR/EULAR 2010 classification criteria for RA. RA individuals were categorised into three pathotypes based on histological classification of synovial tissue: Lympho-myeloid, Diffuse-Myeloid and pauci-immune Fibroid (for more details see Humby, F., et al. *"Synovial cellular and molecular signatures stratify clinical response to csDMARD therapy and predict radiographic progression in early rheumatoid arthritis patients." Ann*

*Rheum Dis* (2019), the contents of which are incorporated herein by reference). Patients were treated with methotrexate. Response status after 6 months of mixed DMARD therapy was determined by EULAR response criteria based on DAS28-ESR.

Chiral LC-MS/MS Analysis

For chiral lipidomic analysis, a Chiralpak AD-RH column (150 mm×2.1 mm×5 μm) was used with isocratic methanol/water/acetic acid 95:5:0.01 (v/v/v) at 0.15 ml/min. To monitor isobaric monohydroxy docosapentaenoic acid levels, a multiple reaction monitoring (MRM) method was developed using signature ion fragments for each molecule as in Dalli J, Chiang N, Serhan C N. Elucidation of novel 13-series resolvins that increase with atorvastatin and clear infections. Nat Med 21, 1071-1075 (2015).

Data

The data used for the machine learning models and network analyses consisted of the lipid mediator profiles of patients with RA who responded (n=30) or did not (n=24) to the treatment with DMARDs for the first PEAC-derived patient cohort. The lipid mediator profile included DHA-derived resolvins (RvD1, RvD2, RvD3, RvD4, RvD5, RvD6, 17-RvD1 and 17-RvD3), protectins (PD1, 17-PD1, 10S,17S-diHDAH and 22-OH-PD1), PCTRs (PCTR1, PCTR2 and PCTR3), maresins (MaR1, MaR2, 7S,14S-diHDHA, 4,14-diHDHA, 14-oxo-MaR1 and 22-OH-MaR1), MCTRs (MCTR1, MCTR2 and MCTR3), 13-series resolvins (RvT1, RvT2, RvT3 and RvT4), n-3 DPA-derived resolvins ($RvD1_{n-3\ DPA}$, $RvD2_{n-3\ DPA}$ and $RvD5_{n-3\ DPA}$), n-3-DPA derived protectins ($PD1_{n-3\ DPA}$ and 10S, 17S-diHDPA), n-3 DPA-derived maresins ($MaR1_{n-3\ DPA}$), E-series resolvins (RvE1, RvE2 and RvE3), leukotrienes ($LXA_4$, $LXB_4$, 5S,15S-diHETE, 20-OH-$LTB_4$, 20-COOH-$LTB_4$, 6-trans-$LTB_4$ and 12-epi-6-trans-$LTB_4$), cysteinyl leukotrienes ($LTC_4$, $LTD_4$ and $LTE_4$), prostaglandins ($PGD_2$, $PGE_2$, $PGF_{2a}$) and thromboxane ($TXB_2$). A Clinical Score model was obtained using the following clinical parameters: disease duration, erythrocyte sedimentation rate (ESR), rheumatoid factor (RF titre), tiredness visual analogue scale (VAS), pain VAS, patient global health VAS, physician global assessment VAS, swollen joints number, disease activity score-28 (DAS28) and 12 max US Synovial Thickness and US Power Doppler scores. A second patient cohort of 45 patients (37 responders and 8 non-responders) was obtained from the PEAC study and was used as the validation dataset for the lipid mediator profiling and Clinical Score models, and also as the training dataset for improved models based on specific biomarkers. Age, sex and clinical parameters not mentioned before were not considered for this first approximation of creating a model able to classify the response of RA patients to DMARD treatment.

Model Building

Data were preprocessed and analysed using R Software (version 3.5.1; https://www.r-project.org/) and RStudio environment (version 1.1.456; https://www.rstudio.com/).

From the exploratory analysis, two samples were removed for showing outlier concentrations of TXB2, which likely reflected coagulation during sample collection and an additional sample was removed due to lack of clinical records. Although no normalization was required since all the lipid mediator concentrations were calculated based on the same amount of standard, the concentrations were scaled by subtracting the mean and dividing by the standard deviation of each feature.

Two supervised machine learning methodologies were used to create the classifier models: classyfire (Chatzimichali, E. A. & Bessant, C. "*Novel application of heuristic*

*optimisation enables the creation and thorough evaluation of robust support vector machine ensembles for machine learning applications*". Metabolomics 12, 16 (2016), the contents of which are incorporated herein by reference) and randomForest (Breiman, L. *Classification and Regression Trees*, (Routledge, 2017), the contents of which are incorporated herein by reference). Classyfire uses Support Vector Machine (SVM) to separate groups by organizing the samples in two spaces divided by a hyperplane in a way that the distances between the samples in the same group are not too wide and the distance between the groups is as large as possible (Bennett, K. P. & Campbell, C. "Support vector machines." *ACM SIGKDD Explorations Newsletter* 2, 1-13 (2000), the contents of which are incorporated herein by reference). Besides that, it uses bootstrapping (new datasets created by iteratively resampling of the original data with replacement) to improve and validate the models. In this study, classyfire was implemented using the R Package "classyfire" (https://crans-project.org/src/contrib/Archive/classyfire/), with 70 bootstrap iterations and 70 individual classifiers in each ensemble. We also used the inbuilt automatic optimization step that includes minimization of the bootstrapping error 36 in the R Package "classyfire" to improve and validate the models (see FIG. 13 for representative outcomes).

Random forests operates by getting the consensus of weak decision tree classifiers (Han, T., Jiang, D., Zhao, Q., Wang, L. & Yin, K. "*Comparison of random forest, artificial neural networks and support vector machine for intelligent diagnosis of rotating machinery.*" Transactions of the Institute of Measurement and Control 40, 2681-2693 (2018), the contents of which are incorporated herein by reference). The decision trees are created using the features as vertices and classes as leaves; each tree is designed using a different set of randomly chosen features (Lötsch, J., et al. "*Machine-learning based lipid mediator serum concentration patterns allow identification of multiple sclerosis patients with high accuracy.*" Sci. Rep. 8, 14884 (2018), the contents of which are incorporated herein by reference). In this case, the R package "randomForest" (https://crans-project.org/package=randomForest) (which also uses bootstrapping as the validation method) was used with a parameters setting of 10,000 trees per run and the design of a small loop to define the best number of variables randomly sampled as candidates at each split. Increasing the number of ntrees beyond this value did not markedly improve the outcomes (see FIG. 13 for representative outcomes).

Model Testing

Receiver operating characteristic curves (ROC curves) were built to evaluate the prediction accuracy of the models when predicting between DMARDs responder and DMARDs non-responder in a test dataset. ROC curves are created by plotting the true positive rate against the false positive rate, showing the sensitivity and specificity of the model, when the discrimination threshold changes. The area under the curve (AUC) is calculated as the prediction performance of the models. ROC curves were created using the R package "pROC" (https://cran.r-project.org/web/packages/pROC/index.html). AUC values close to 1 (AUC>0.8) refer to good classifier models.

Receiver operating characteristic curves (ROC curves) were built to evaluate the prediction accuracy of the models when predicting between DMARDs responder and DMARDs non-responder in a test dataset. ROC curves are created by plotting the true positive rate against the false positive rate, showing the sensitivity and specificity of the model, when the discrimination threshold changes. The area under the curve (AUC) is calculated as the prediction performance of the models. ROC curves were created using the R package "pROC" (https://cran.r-project.org/web/packages/pROC/index.html). AUC values close to 1 (AUC>0.8) refer to good classifier models. Alongside ROC curves, other statistics such as the percentage of correctly classified samples (% accuracy score), specificity and sensitivity were also calculated.

Feature Selection and Model Improvement

As random forests showed the best validation scores during the testing step, the model improvement was based on the random forests methodology. The lipid mediators were separated in groups based on their precursors (DHA, n-3 DPA, EPA and AA) or the distinct clusters of mediators. Besides that, and using the "importance" function of randomForest, which organizes the model's features by relevance based on the decrease of the mean accuracy of the model when the specific feature is not present, different models were created using only the most relevant lipid mediators. The % accuracy score and MCC were calculated for all the models and, according to the results, the best models and the most relevant biomarkers for the classification of the DMARD-responder and DMARD-non-responder patients were selected.

Pathotypes Analyses

All the data (training and validation cohorts) was separated based on the specific pathotype shown for the patients: pauci-immune/fibroid (n=28), lympho-myeloid (n=27) and diffuse-myeloid (n=31). This was made with the purpose of seeking better classification models and seeing if specific lipid mediators were responsible for the different manifestation of the disease. The models were build using randomForest and different statistic scores were calculated for the validation of each model.

Network Analyses

Statistical differences between the normalised concentrations (expressed as the fold change) of the lipid mediators from the DMARD-non-responder and DMARD-responder groups were determined using a student t-test followed by a multiple comparison correction using Benjamini-Hochberg procedure. Based on these differences, lipid mediator biosynthesis networks were constructed using Cytoscape 3.7.1. The different pathways were illustrated using different colours and line shapes, while up or down regulated mediators were denoted with diamond or triangle shapes, respectively, and on changes of the node's size. Bolded mediators represent statistical differences between the two groups. The comparison between DMARD-non-responders and DMARD-responders were made with pre and post-treatment data.

Targeted Lipid Mediator Profiling

Plasma was obtained from peripheral blood of healthy volunteers, patients and mouse following centrifugation at 1500×g for 10 min at room temperature. Paws were collected and immediately transferred to liquid nitrogen prior to homogenization in 1 ml ice cold MeOH and homogenized using a glass dounce. All samples for LC-MS/MS-based profiling were extracted using solid-phase extraction columns as in Walker, M. E., Souza, P. R., Colas, R. A. & Dalli, J. "13-*Series resolvins mediate the leukocyte-platelet actions of atorvastatin and pravastatin in inflammatory arthritis.*" *FASEB J* 31, 3636-3648 (2017), the contents of which are incorporated herein by reference. Prior to sample extraction, deuterated internal standards, representing each region in the chromatographic analysis (500 pg each) were added to facilitate quantification. Samples were kept at −20° C. for a minimum of 45 min to allow protein precipitation.

Supernatants were subjected to solid phase extraction, methyl formate fraction collected, brought to dryness and suspended in phase (methanol/water, 1:1, vol/vol) for injection on a Shimadzu LC-20AD HPLC and a Shimadzu SIL-20AC autoinjector, paired with a QTrap 5500 or QTrap 6500 plus (Sciex). An Agilent Poroshell 120 EC-C18 column (100 mm×4.6 mm×2.7 μm) was kept at 50° C. and mediators eluted using a mobile phase consisting of methanol/water/acetic acid of 20:80:0.01 (vol/vol/vol) that was ramped to 50:50:0.01 (vol/vol/vol) over 0.5 min and then to 80:20:0.01 (vol/vol/vol) from 2 min to 11 min, maintained till 14.5 min and then rapidly ramped to 98:2:0.01 (vol/vol/vol) for the next 0.1 min. This was subsequently maintained at 98:2:0.01 (vol/vol/vol) for 5.4 min, and the flow rate was maintained at 0.5 ml/min. QTrap 5500 or QTrap 6500 plus were operated using a multiple reaction monitoring method as in Walker, M. E., Souza, P. R., Colas, R. A. & Dalli, J. "13-*Series resolvins mediate the leukocyte-platelet actions of atorvastatin and pravastatin in inflammatory arthritis.*" *FASEB J* 31, 3636-3648 (2017), the contents of which are incorporated herein by reference. Each lipid mediator was identified using established criteria including matching retention time to synthetic or authentic standards and at least 6 diagnostic ions (Walker, M. E., Souza, P. R., Colas, R. A. & Dalli, J. "13-*Series resolvins mediate the leukocyte-platelet actions of atorvastatin and pravastatin in inflammatory arthritis.*" *FASEB J* 31, 3636-3648 (2017), the contents of which are incorporated herein by reference). Calibration curves were obtained for each mediator using lipid mediator mixtures at 0.78, 1.56, 3.12, 6.25, 12.5, 25, 50, 100, and 200 μg that gave linear calibration curves with an $r^2$ values of 0.98-0.99.

Healthy Volunteer's Blood Collection

Venous peripheral blood was collected at indicated intervals in sodium citrate (3.2%) from fasting volunteers that declared not taking NSAIDS for at least 14 days, caffeine and alcohol for at least 24 h and fatty fish for 48 h. Volunteers gave written consent in accordance with a Queen Mary Research Ethics Committee (QMREC 2014:61) and the Helsinki declaration.

Human Whole Blood Incubations

In select experiments, whole blood was incubated with L002 (2 μM) or SB202190 (5 μM) or vehicle (0.1% DMSO) for 45 min (37° C.). Blood was then incubated with MTX (100 nM) for 45 min (37° C.). Plasma was then separated by centrifugation at 1,500×g for 10 min for lipid mediators profiling.

Animals

Male C57BL/6 mice and Alox15$^{-/-}$ (11-week-old) were procured from Charles River Laboratories (Kent, United Kingdom). Experiments strictly adhered to United Kingdom Home Office regulations (Guidance on the Operation of Animals, Scientific Procedures Act) and Laboratory Animal Science Association Guidelines (Guiding Principles on Good Practice for Animal Welfare and Ethical Review Bodies). All animals were provided with standard laboratory diet and water ad libitum and kept on a 12-h light/dark cycle.

Inflammatory Arthritis

Male C57BL/6 mice and Alox15$^{-/-}$ (11-week-old) were administered K/BxN serum (100 μl, i.p.) on day 0 and day 2 to initiate inflammatory arthritis. Mice were then given MTX (25 mg/kg each), or vehicle (DPBS$^{-/-}$ that contained 1% DMSO) via intraperitoneal injection on days 3, 5, and 7. Clinical scores were monitored daily by using a 26-point arthritic scoring system. Swelling and redness of mouse ankles/wrists, pads, and digits were inspected daily. Blood and paws were collected on day 8.

In select experiments, male C57BL/6 mice (11-week-old) were given L002 (20 mg/kg each) or SB202190 (20 mg/kg each) before MTX injections. Clinical scores were monitored daily by using a 26-point arthritic scoring system. Swelling and redness of mouse ankles/wrists, pads, and digits were inspected daily. Blood and paws were collected on day 8 after arthritis onset.

Enzyme Transcript Expression

RNA was extracted from whole blood samples in RNALater solution using the Ambion Ribo-Pure Blood kit (ThermoFisher Scientific). Total RNA-Sequencing (RNA-seq) was performed on an Illumina HiSeq2500 platform. Raw data were quality-controlled using FastQC, trimmed or removed with Cutadapt. Transcript abundance was derived from paired sample FASTQ files over GENCODE v24/GRCh38 transcripts using Kallisto v0.43.0. Normalization of the raw data and differential gene expression analysis between DMARD-responder and DMARD-non-responder were performed using the quasi-likelihood method of the Bioconductor R package "edgeR" (https://bioconductor.org/packages/release/bioc/html/edgeR.html). Results are expressed as the log counts per million of each gene. RNA-Seq data are uploaded to ArrayExpress and are accessible via accession E-MTAB-6141.

Flow Cytometry

Paws were harvested and leukocytes were isolated as previously described (Norling, L. V., et al. "*Proresolving and cartilage-protective actions of resolvin D1 in inflammatory arthritis.*" *JCI Insight* 1, e85922 (2016), the contents of which are incorporated herein by reference). In brief, paws were incubated in RPMI-1640 that contained 0.5 µg/ml collagenase D and 40 µg/ml DNaseI at 37° C. for 30 min with vigorous agitation. Isolated cells were passed through a 70-µM strainer and suspended in RPMI-1640 that contained 2 U/ml penicillin, 100 mg/ml streptomycin, and 10% fetal bovine serum, then centrifuged at 400 g for 10 min. Isolated cells were suspended in DPBS$^{-/-}$ that contained 0.02% bovine serum albumin and 1% Fc-blocking IgG (v/v) and were incubated with 0.1% live/dead stain for 20 min on ice. Cells were washed using DPBS$^{-/-}$ and incubated with the following antibodies: PE CD64 (FcγRI, clone X54-5/7.1, host mouse, Biolegend), Alexa Fluor 700 Ly-6G (clone 1A, host rat, Biolegend), Brilliant Violet 785 Ly-6C (clone HK1.4, host rat, Biolegend), APC/Cyanine7 CD45 (clone 30-F11, host rat, Biolegend), Alexa Fluor 488 CD11 b (clone M1/70, host rat, Biolegend), APC Siglec F (clone ES22-10D8, host rat, Miltenyi Biotec), Brilliant Violet 711 CD115 (CSF-1R) (clone AFS98, host rat, Biolegend) and Brilliant Violet 510 CD43 (clone 1G10, host mouse, BD Biosciences) for 45 min on ice. These were then washed and fixed using 1% paraformaldehyde. CountBright Absolute Counting Beads were used for leukocyte enumeration. Staining was evaluated using LSRFortessa cell analyzer and analyzed using FlowJo software.

Histology

Paws were placed in 10% formaldehyde (v/v; in water that contained 0.65% Na$_2$HPO$_4$ and 0.4% NaH$_2$PO$_4$) for 48 h. These were then placed in 10% EDTA in DPBS for 2 wk. When decalcified, paws were embedded in wax as previously described (Walker, M. E., Souza, P. R., Colas, R. A. & Dalli, J. "13-*Series resolvins mediate the leukocyte-platelet actions of atorvastatin and pravastatin in inflammatory arthritis.*" *FASEB J* 31, 3636-3648 (2017), the contents of which are incorporated herein by reference). Four-micron sections were obtained and hematoxylin and eosin staining was carried out by the Barts Cancer Institute Pathology Core as described in Walker, M. E., Souza, P. R., Colas, R. A. &

62

Dalli, J. "13-*Series resolvins mediate the leukocyte-platelet actions of atorvastatin and pravastatin in inflammatory arthritis.*" *FASEB J* 31, 3636-3648 (2017), the contents of which are incorporated herein by reference.

Statistical Analysis

We performed all statistical analyses and data derivation using R (R Development Core Team. *R: A language and environment for statistical computing.* (2016), the contents of which are incorporated herein by reference), MetaboAnalyst 4.0 (Chong, J., Yamamoto, M. & Xia, J. MetaboAnalystR 2.0: "*From Raw Spectra to Biological Insights.*" *Metabolites* 9 (2019), the contents of which are incorporated herein by reference), Prism 8 and Microsoft Excel. Results presented in the figures are expressed as means and those displayed in the tables are displayed as mean±sem. Differences between groups were determined using one-sample T test (normalized data) or Mann Whitney test (2 groups) or one-way ANOVA (more than 2 groups). Sample sizes for each experiment were determined on the variability observed in prior experiments. Partial least squares-discrimination analysis (PLS-DA) and Orthogonal Partial least squares-discrimination analysis (OPLS-DA) were performed using MetaboAnalyst 4.0 Chong, J., Yamamoto, M. & Xia, J. MetaboAnalystR 2.0: "*From Raw Spectra to Biological Insights.*" *Metabolites* 9 (2019), the contents of which are incorporated herein by reference) or SIMCA 14.1 software (Umetrics, Umea, Sweden) after mean centering and unit variance scaling of lipid mediator concentrations. PLS-DA is based on a linear multivariate model that identifies variables that contribute to class separation of observations (e.g. treatment response) on the basis of their variables (lipid mediator concentrations). During classification, observations were projected onto their respective class model. The score plot illustrates the systematic clusters among the observations (closer plots presenting higher similarity in the data matrix).

REFERENCES

Colas R A, Shinohara M, Dalli J, Chiang N and Serhan C N. *Am J Physiol Cell Physiol.* 2014; 307:C39-54

Dalli, J. & Serhan, C. N. *Blood* 120, e60-72 (2012)

Gao, Y., et al. *J Immunol* 195, 3086-3099 (2015)

Serhan, C. N. & Levy, B. D. *Clin Invest* 128, 2657-2669 (2018),

Dalli, J., Colas, R. A., Walker, M. E. & Serhan, C. N. Methods Mol Biol 1730, 59-72 (2018)

Chong, J., Yamamoto, M. & Xia, J. MetaboAnalystR 2.0: *Metabolites* 9 (2019)

Dalli, J., Chiang, N. & Serhan, C. N. *Nat Med* 21, 1071-1075 (2015)

Humby, F., et al. *Ann Rheum Dis* (2019)

Fredman, G., et al. *Proc Natl Acad Sci USA* 111, 14530-14535 (2014

Arnardottir, H. H., et al. Resolvin *J Immunol* 197, 2362-2368 (2016)

Chiang, N., Dalli, J., Colas, R. A. & Serhan, C. N. *J Exp Med* 212, 1203-1217 (2015)

Dalli, J., Ramon, S., Norris, P. C., Colas, R. A. & Serhan, C. N. *FASEB J* 29, 2120-2136 (2015)

Barden, A. E., et al. *Prostaglandins Leukot Essent Fatty Acids* 107, 24-29 (2016)

Xu, Z. Z., et al. *Nat Med* 16, 592-597, 591p following 597 (2010) Radmark, O., Werz, O., Steinhilber, D. & Samuelsson, B. *Biochim Biophys Acta* 1851, 331-339 (2015)

Edno, L., et al. *Ther Drug Monit* 18, 128-134 (1996)

Thornton, C. C., et al. *Ann Rheum Dis* 75, 439-448 (2016).

Wu, C. W., et al. *Oncol Rep* 37, 2177-2184 (2017)

Shankaranarayanan, P., Chaitidis, P., Kuhn, H. & Nigam, S. *J Biol Chem* 276, 42753-42760 (2001)

Xu, B., et al. *Mol Cell Biol* 23, 3918-3928 (2003)

Fredman, G., et al. *Nat Commun* 7, 12859 (2016)

Norling, L. V., et al. *JCI Insight* 1, e85922 (2016)

Chatzimichali, E. A. & Bessant, C. *Metabolomics* 12, 16 (2016)

Breiman, L. *Classification and Regression Trees*, (Routledge, 2017)

Bennett, K. P. & Campbell, C. *ACM SIGKDD Explorations Newsletter* 2, 1-13 (2000)

Han, T., Jiang, D., Zhao, Q., Wang, L. & Yin, K. *Transactions of the Institute of Measurement and Control* 40, 2681-2693 (2018)

Lötsch, J., et al. *Sci. Rep.* 8, 14884 (2018)

Chicco, D. *BioData Min* 10, 35 (2017)

Walker, M. E., Souza, P. R., Colas, R. A. & Dalli, J. *FASEB J* 31, 3636-3648 (2017)

Norling, L. V., et al. *JCI Insight* 1, e85922 (2016)

R Development Core Team. *R: A language and environment for statistical computing.* (2016)

Chin et al. 2012. *Lab on a Chip.* 2012; 12:2118-2134.

Chan C D, Laksanasopin T, Cheung Y K, Steinmiller D et al. *Nature Medicine.* 2011; 17(8):1015-1019.

The invention claimed is:

1. A method treating an inflammatory condition comprising:
  (i) measuring the level of at least one specialized pro-resolving mediator (SPM) in a disease-modifying anti-rheumatic drug (DMARD) naïve patient sample from a patient having the inflammatory condition and classifying the patient as a predicted DMARD responder or a predicted DMARD non-responder; and
  (ii) administering to the patient:
    (a) a non-biological DMARD if the patient is a predicted DMARD responder; or
    (b) a biological DMARD if the patient is a predicted DMARD non-responder.

2. The method of claim 1, comprising measuring the levels of at least two SPM and inputting the levels of the at least two SPM into a trained machine learning algorithm, the trained machine learning algorithm being arranged to:
  (i) compare the levels of the at least two SPM from the sample with the levels of the same at least two SPM in a database, and
  (ii) output whether the patient is a DMARD responder or a DMARD non-responder.

3. The method of claim 2 wherein the trained machine learning algorithm is trained based on training data, the training data comprising:
  first data including lipid mediator profiles for a plurality of patients; and
  second data identifying whether each of the plurality of patients is a DMARD responder or a DMARD non-responder.

4. The method according to claim 1, wherein the inflammatory condition is rheumatoid arthritis.

5. The method according to claim 1, wherein the patient is classified as a predicted DMARD non-responder when the level of the at least one SPM is increased compared to a control.

6. The method according to claim 1, further comprising measuring the level of at least one pro-inflammatory eicosanoid, and wherein an increase in the level of at least one pro-inflammatory eicosanoid compared to a control predicts that the patient is a DMARD non-responder.

7. The method of claim 6, wherein the pro-inflammatory eicosanoid is $PGD_2$ and/or $PGE_2$.

8. The method of claim 1, wherein the at least one SPM is a DHA metabolite, n-3 DPA metabolite, AA metabolite and/or an EPA metabolite.

9. The method of claim 1, wherein the at least one SPM is RvT3; RvT4; RvE2; RvD1; $MaR1_{n-3\ DPA}$; RvT4; 14-oxo-MaR1; 17R-RvD3; 15R-$LXB_4$; RvD3; RvD4; $TxB_2$; $LTB_4$; 20-COOH-$LTB_4$; $LTE_4$; 10S, 17S,diHDHA (PDX); 17R-PD1; 15R-$LXA_4$; $PGE_2$; $PGD_2$; 10S, 17S-diHDPA; 5S, 12S-diHETE; 4S, 14S-diHDHA; and/or 5S, 15S-diHETE.

10. The method of claim 1, wherein the at least one SPM is RvD4, $MaR1_{n-3\ DPA}$, 10S, 17S-diHDPA and/or 15R-$LXA_4$.

11. The method of claim 1, wherein the at least one SPM is:
  (a) involved in coordinating the host response during ongoing inflammation; and/or
  (b) a mediator linked with pain modulation.

12. The method of claim 1, further comprising measuring one or more markers of ALOX5 activity; one or more markers of ALOX12 activity and/or one or more markers of ALOX15 activity.

13. The method of claim 12, wherein:
  (a) the one or more markers of ALOX5 activity are selected from the group consisting of 5-HETE, 5HEPE, 7-HDPA and 7-HDHA;
  (b) the one or more markers of ALOX12 activity are selected from the group consisting of 14-HDPA and 14-HDHA; and/or
  (c) the one or more markers of ALOX15 activity are selected from the group consisting of 17-HDPA, 17-HDHA, 15-HEPE and 15-HETE.

14. The method of claim 1, comprising measuring the levels of at least two SPM and wherein a multivariate analysis is used to detect an increase in the levels of the at least two SPM compared to controls.

15. The method of claim 1, comprising measuring the levels of at least two SPM and wherein a trained machine learning model is used to detect an increase in the levels of the at least two SPM compared to controls.

16. The method of claim 1, wherein the sample is a plasma sample or a whole blood sample.

17. The method of claim 1, wherein the level of the at least one SPM is measured using liquid chromatography tandem mass spectrometry (LC-MS/MS).

18. The method of claim 1, wherein the level of the at least one SPM is measured using an immunoassay.

19. The method of claim 1, wherein the at least one SPM is at least four SPM wherein the at least four SPM comprise RvD4, 10S, 17S-diHDPA, 15R-$LXA_4$ and $MaR1_{n-3\ DPA}$.

20. The method of claim 1, wherein the at least one SPM is RvD4, 5S, 12S-diHETE, 4S, 14S-diHDHA, $MaR1_{n-3\ DPA}$, 10S, 17S-diHDPA and/or 15R-$LXA_4$.

21. The method of claim 1, wherein the at least one SPM is at least six SPM wherein the at least six SPM comprise (i) RvD4; (ii) 5S, 12S-diHETE; (iii) 4S, 14S-diHDHA; (iv) $MaR1_{n-3\ DPA}$; (v) 10S, 17S-diHDPA; and (vi) 15R-$LXA_4$.

22. The method of claim 1, wherein the DMARD is a non-biological DMARD selected from the group consisting of methotrexate, aspiring, hydroxychloroquine, leflunomide, sulfasalazine, gold salts, azathioprine, and cyclosporine.

* * * * *